United States Patent
Bahjat et al.

(10) Patent No.: US 10,925,945 B2
(45) Date of Patent: Feb. 23, 2021

(54) BACTERIAL VACCINES DEFICIENT IN THE 2-C-METHYL-D-ERYTHRITOL-4-PHOSPHATE PATHWAY AND METHODS OF PREPARATION AND USE THEREOF

(71) Applicant: PROVIDENCE HEALTH & SERVICES-OREGON, Portland, OR (US)

(72) Inventors: Keith Bahjat, Portland, OR (US); Yoshinobu Koguchi, Portland, OR (US); Alejandro F. Alice, Portland, OR (US)

(73) Assignee: PROVIDENCE HEALTH & SERVICES-OREGON, Portland, OR (US)

( * ) Notice: Subject to any disclaimer, the term of this patent is extended or adjusted under 35 U.S.C. 154(b) by 0 days.

(21) Appl. No.: 15/519,114

(22) PCT Filed: Oct. 13, 2015

(86) PCT No.: PCT/US2015/055350
§ 371 (c)(1),
(2) Date: Apr. 13, 2017

(87) PCT Pub. No.: WO2016/061115
PCT Pub. Date: Apr. 21, 2016

(65) Prior Publication Data
US 2017/0216420 A1   Aug. 3, 2017

Related U.S. Application Data

(60) Provisional application No. 62/063,351, filed on Oct. 13, 2014.

(51) Int. Cl.
*A61K 39/00* (2006.01)
*C12N 15/74* (2006.01)

(52) U.S. Cl.
CPC .......... *A61K 39/0011* (2013.01); *C12N 15/74* (2013.01); *A61K 2039/522* (2013.01); *A61K 2039/523* (2013.01); *A61K 2039/572* (2013.01); *A61K 2039/6031* (2013.01); *A61K 2039/70* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,767,063 A | 6/1998 | Lee et al. | |
| 5,830,702 A | 11/1998 | Portnoy et al. | |
| 5,888,530 A | 3/1999 | Netti et al. | |
| 6,051,237 A | 4/2000 | Paterson | |
| 6,090,611 A | 7/2000 | Covacci et al. | |
| 6,099,848 A | 8/2000 | Frankel et al. | |
| 6,379,943 B1 | 4/2002 | Graham et al. | |
| 7,842,289 B2 | 11/2010 | Dubensky et al. | |
| 2002/0150588 A1 | 10/2002 | Allison et al. | |
| 2004/0013690 A1 | 1/2004 | Portnoy et al. | |
| 2005/0048081 A1 | 3/2005 | Frankel et al. | |
| 2005/0281783 A1 | 12/2005 | Kinch et al. | |
| 2009/0196887 A1* | 8/2009 | Morita .................. | A61K 39/04 424/235.1 |
| 2011/0223187 A1* | 9/2011 | Shahabi .............. | A61K 39/0011 424/192.1 |
| 2012/0100170 A1* | 4/2012 | Lauer ..................... | A61K 39/29 424/189.1 |

FOREIGN PATENT DOCUMENTS

| | | | | |
|---|---|---|---|---|
| WO | 9614087 A1 | 5/1996 | | |
| WO | 9925376 A1 | 5/1999 | | |
| WO | 2004006837 A2 | 1/2004 | | |
| WO | 2007103225 A2 | 9/2007 | | |
| WO | WO-2007103225 A2 * | 9/2007 | ......... | A61K 39/0011 |
| WO | 2007117371 A2 | 10/2007 | | |
| WO | 2008/131730 A2 | 10/2009 | | |
| WO | 2009143085 A1 | 11/2009 | | |

(Continued)

OTHER PUBLICATIONS

Yan et al. Infection and Immunity Aug. 2008;76(8);3439-50.*
Kanda et al. The Journal of Virology, Nov. 2007, vol. 81, No. 22, p. 12375-12381.*
Toussaint et al. Expert Rev. Vaccines 12(10), 1139-1154, 2013.*
Frencher et al. J Leukoc Biol Dec. 2014; 96(6):957-67. Epub Aug. 11, 2014.*
Nakatsura et al., Glypican-3, overexpressed specifically in human hepatocellular carcinoma, is a novel tumor marker. Biochem Biophys Res Commun. Jun. 20, 2003;306(1):16-25.

(Continued)

*Primary Examiner* — Oluwatosin A Ogunbiyi
(74) *Attorney, Agent, or Firm* — Acuity Law Group, PC; Michael A. Whittaker

(57) ABSTRACT

The present invention relates to the preparation and use in primates of whole organismvaccines in which the MEP pathway is disrupted such that synthesis of HMBPP by the bacterial cells is substantially blocked. The data provided demonstrates that, when bacteria or other vaccine vectors that comprise an active MEP pathway are used in vaccine methods, the γδ T cell response dominates, potentially clearing the vaccine strain via γδ T cell-mediated killing of vector infected antigen presenting cells and reducing its utility as a stimulator of a productive adaptive immune response, specifically priming or boosting of $CD4^+$ and $CD8^+$ αβ T cell responses, specific for listerial-encoded antigens. By disrupting the MEP pathway, activation and expansion of γδ T cells is limited in the recipient primate, resulting in resulting in an increase in the magnitude and duration of inflammation and in the magnitude and duration of antigen presentation by the cellular vaccine.

24 Claims, 7 Drawing Sheets
Specification includes a Sequence Listing.

(56) References Cited

FOREIGN PATENT DOCUMENTS

| WO | 2012068360 A1 | 5/2012 |
|---|---|---|
| WO | 2014106123 A1 | 7/2014 |

OTHER PUBLICATIONS

Nakatsura et al., Identification of Glypican-3 as a Novel Tumor Marker for Melanoma. Clin Cancer Res. Oct. 1, 2004;10(19):6612-6621.

Neumann et al., Identification of an HLA-DR-restricted peptide epitope with a promiscuous binding pattern derived from the cancer testis antigen HOM-MEL-40/SSX2. Int J Cancer. Nov. 20, 2004;112(4):661-668.

Nicoletto et al., BRCA-1 and BRCA-2 mutations as prognostic factors in clinical practice and genetic counselling. Cancer Treat Rev. Oct. 2001;27(5):295-304.

Nunes-Duby et al., Similarities and differences among 105 members of the Int family of site-specific recombinases. Nucleic Acids Res. Jan. 15, 1998;26(2):391-406.

Oberste et al., Evidence for Frequent Recombination within Species Human Enterovirus B Based on Complete Genomic Sequences of All Thirty-Seven Serotypes. J Virol. Jan. 2004;78(2):855-867.

Oberthuer et al., The Tumor-Associated Antigen PRAME Is Universally Expressed in High-Stage Neuroblastoma and Associated with Poor Outcome. Clin Cancer Res. Jul. 1, 2004;10(13):4307-4313.

Oliveira-Ferreira and Daniel-Ribeiro, Protective CD8+ T Cell Responses against the Pre-erythrocytic Stages of Malaria Parasites: an Overview. Mem Inst Oswaldo Cruz. Feb. 2001;96(2):221-227.

O'Riordan et al., Listeria intracellular growth and virulence require host-derived lipoic acid. Science. Oct. 17, 2003;302(5644):462-464.

Orvell et al., Antigenic relationships between six genotypes of the small hydrophobic protein gene of mumps virus. J Gen Virol. Oct. 2002;83(Pt 10):2489-2496.

Otte et al., MAGE—A Gene Expression Pattern in Primary Breast Cancer Cancer Res. Sep. 15, 2001;61 (18):6682-6687.

Oyston and Quarry, Tularemia vaccine: past, present and future. Antonie Van Leeuwenhoek. May 2005;87(4):277-281.

Padilla et al., Imaging of the varicella zoster virion in the viral highways: Comparison with herpes simplex viruses 1 and 2, cytomegalovirus, pseudorabies virus, and human herpes viruses 6 and 7. J Med Virol. 2003;70 Suppl 1:S103-S110.

Patel et al., Development of a simple restriction fragment length polymorphism assay for subtyping of coxsackie B viruses. J Virol Methods. Sep. 15, 2004;120(2):167-172.

Peh et al., Frequent presence of subtype a virus in Epstein-Barr virus-associated malignancies. Pathology. Oct. 2002;34(5):446-450.

Pisarev et al., Full-length dominant-negative survivin for cancer immunotherapy. Clin Cancer Res. Dec. 15, 2003;9(17):6523-6533.

Porsch-Ozcurumez et al., Comparison of Enzyme-Linked Immunosorbent Assay, Western Blotting, Microagglutination, Indirect Immunofluorescence Assay, and Flow Cytometry for Serological Diagnosis of Tularemia. Clin Diagn Lab Immunol. Nov. 2004;11(6):1008-1015.

Ramsay et al., DNA vaccination against virus infection and enhancement of antiviral immunity following consecutive immunization with DNA and viral vectors. Immunol Cell Biol. Aug. 1997;75(4):382-388.

Renkvist et al., A listing of human tumor antigens recognized by T cells. Cancer Immunol Immunother. Mar. 2001;50(1):3-15.

Reynolds et al., HLA-Independent Heterogeneity of CD8+ T Cell Responses to MAGE-3, Melan-A/MART-1, gp100, Tyrosinase, MC1R, and TRP-2 in Vaccine-Treated Melanoma Patients. J Immunol. Dec. 15, 1998;161(12):6970-6976.

Rezig et al., Molecular Characterization of Coxsackievirus B5 Isolates. J Med Virol. Feb. 2004;72(2):268-274.

Ries et al., Investigation of the expression of melanoma antigen-encoding genes (MAGE-A1 to -A6) in oral squamous cell carcinomas to determine potential targets for gene-based cancer immunotherapy. Int J Oncol. Mar. 2005;26(3):817-824.

Ripio et al., A Gly145Ser substitution in the transcriptional activator PrfA causes constitutive overexpression of virulence factors in Listeria monocytogenes. J Bacteriol. Mar. 1997;179(5):1533-1540.

Roden and Wu, Preventative and therapeutic vaccines for cervical cancer. Expert Rev Vaccines. Aug. 2003;2(4):495-516.

Roner et al., Identification of signals required for the insertion of heterologous genome segments into the reovirus genome. Proc Natl Acad Sci U S A. Dec. 19, 1995;92(26):12362-12366.

Salazar-Onfray et al., Synthetic peptides derived from the melanocyte-stimulating hormone receptor MC1R can stimulate HLA-A2-restricted cytotoxic T lymphocytes that recognize naturally processed peptides on human melanoma mils. Cancer Res. Oct. 1, 1997;57(19):4348-4355.

Santin et al., The serine protease stratum comeum chymotryptic enzyme (kallikrein 7) is highly overexpressed in squamous cervical cancer cells. Gynecol Oncol. Aug. 2004;94(2):283-288.

Sarcevic et al., Expression of Cancer/Testis Tumor Associated Antigens in Cervical Squamous Cell Carcinoma. Oncology. 2003;64(4):443-449.

Sarobe et al., Carcinoembryonic Antigen as a Target to Induce Anti-Tumor Immune Responses. Curr Cancer Drug Targets. Aug. 2004;4(5):443-454.

Sasaki et al., SAGE mRNA expression in advanced-stage lung cancers. Eur J Surg Oncol. Dec. 2003;29(10):900-903.

Sasatomi et al., Expression of tumor rejection antigens in colorectal carcinomas. Cancer. Mar. 15, 2002;94(6):1636-1641.

Scanlan et al., Antigens recognized by autologous antibody in patients with renal-cell carcinoma. Int J Cancer. Nov. 12, 1999;83(4):456-464.

Scanlan et al., Cancer-related serological recognition of human colon cancer: identification of potential diagnostic and immunotherapeutic targets. Cancer Res. Jul. 15, 2002;62(14):4041-4047.

Scanlan et al., Expression of cancer-testis antigens in lung cancer: definition of bromodomain testis-specific gene (BRDT) as a new CT gene, CT9. Cancer Lett. Mar. 31, 2000;150(2):155-164.

Scanlan et al., Humoral immunity to human breast cancer: antigen definition and quantitative analysis of mRNA expression. Cancer Immun. Mar. 30, 2001;1:4.

Scanlan et al., The cancer/testis genes: review, standardization, and commentary. Cancer Immun. Jan. 23, 2004;4:1.

Scarcella et al., Expression of MAGE and GAGE in high-grade brain tumors: a potential target for specific immunotherapy and diagnostic markers. Clin Cancer Res. Feb. 1999;5(2):335-341.

Schmittgen et al., Expression of prostate specific membrane antigen and three alternatively spliced variants of PSMA in prostate cancer patients. Int J Cancer Nov. 1, 2003;107(2):323-329.

Schwartz et al., Novel targeted and immunotherapeutic strategies in chronic myeloid leukemia. Semin Hematol. Jan. 2003;40(1):87-96.

Sepehr et al., Distinct pattern of TP53 mutations in squamous cell carcinoma of the esophagus in Iran. Oncogene. Nov. 1, 2001;20(50):7368-7374.

Sepulveda-Amor et al., A randomized trial demonstrating successful boosting responses following simultaneous aerosols of measles and rubella (MR) vaccines in school age children. Vaccine. Jun. 21, 2002;20(21-22):2790-2795.

Shen et al., Recombinant Listeria monocytogenes as a live vaccine vehicle for the induction of protective anti-viral cell-mediated immunity. Proc Natl Acad Sci U S A. Apr. 25, 1995;92(9):3987-3991.

Shetron-Rama et al., Isolation of Listeria monocytogenes mutants with high-level in vitro expression of host cytosol-induced gene products. Mol Microbiol. Jun. 2003;48(6):1537-1551.

Shigemasa et al., Expression of the protease inhibitor antileukoprotease and the serine protease stratum corneum chymotryptic enzyme (SCCE) is coordinated in ovarian tumors. Int J Gynecol Cancer. Nov.-Dec. 2001;11(6):454-461.

Shirakawa et al., A Cox-2 Promoter-Based Replication-Selective Adenoviral Vector to Target the Cox-2-Expressing Human Bladder Cancer Cells. Clin Cancer Res. Jul. 1, 2004;10(13):4342-4348.

(56) References Cited

OTHER PUBLICATIONS

Shirasawa et al., Receptor for advanced glycation end-products is a marker of type I lung alveolar cells. Genes Cells. Feb. 2004;9(2):165-174.
Shivapurkar et al., Presence of Simian Virus 40 DNA Sequences in Human Lymphoid and Hematopoietic Malignancies and Their Relationship to Aberrant Promoter Methylation of Multiple Genes. Cancer Res. Jun. 1, 2004;64(11):3757-3760.
Siegel et al., Induction of antitumour immunity using survivin peptide-pulsed dendritic cells in a murine lymphoma model. Br J Haematol. Sep. 2003;122(6):911-914.
Simon et al., Cervical response to vaccination against HPV16 E7 in case of severe dysplasia. Eur J Obstet Gynecol Reprod Biol. Aug. 15, 2003;109(2):219-223.
Sjolander et al., Serological divergence of Dobrava and Saaremaa hantaviruses: evidence for two distinct serotypes. Epidemiol Infect. Feb. 2002;128(1):99-103.
Skoble et al., Three Regions within Ada Promote Arp2/3 Complex-Mediated Actin Nucleation and Listeria monocytogenes Motility. J Cell Biol. Aug. 7, 2000;150(3):527-538.
Slager et al., Identification of Multiple HLA-DR-Restricted Epitopes of the Tumor-Associated Antigen CAMEL by CD4+ Th1/Th2 Lymphocytes. J Immunol. Apr. 15, 2004;172(8):5095-5102.
Slager et al., Induction of CAMEL/NY-ESO-ORF2-specific CD8+ T cells upon stimulation with dendritic cells infected with a modified Ad5 vector expressing a chimeric Ad5/35 fiber Cancer Gene Ther. Mar. 2004;11(3):227-236.
Small et al., Immunotherapy of Hormone-Refractory Prostate Cancer With Antigen-Loaded Dendritic Cells. J Clin Oncol. Dec. 1, 2000;18(23):3894-3903.
Smith and Thorpe, Diversity in the serine recombinases. Mol Microbiol. Apr. 2002;44(2):299-307.
Smith et al., Measurement of Cell-Mediated Immunity With a Varicella-Zoster Virus-specific Interferon-g ELISPOT Assay: Responses in an Elderly Population Receiving a Booster Immunization. J Med Virol. 2003;70 Suppl 1:S38-S41.
Smith et al., Neutralization of HIV-1 Subtypes: Implications for Vaccine Formulations. J Med Virol. Nov. 1998;56(3):264-268.
Smits et al., Phylogenetic and Evolutionary Relationships among Torovirus Field Variants: Evidence for Multiple Intertypic Recombination Events. J Virol. 2003 Sep;77(17):9567-9577.
Stams et al., Expression Levels of TEL, AML1, and the Fusion Products TEL-AML1 and AML1-TEL versus Drug Sensitivity and Clinical Outcome in t(12;21)-Positive Pediatric Acute Lymphoblastic Leukemia. Clin Cancer Res. Apr. 15, 2005;11(8):2974-2980.
Steffens et al., Immunohistochemical analysis of tumor antigen saturation following injection of monoclonal antibody G250. Anticancer Res. Mar.-Apr. 1999;19(2A):1197-1200.
Stirnadel et al., Assessment of different sources of variation in the antibody responses to specific malaria antigens in children in Papua New Guinea. Int J Epidemiol. Jun. 2000;29(3):579-586.
Stolier et al., Initial experience with surgical treatment planning in the newly diagnosed breast cancer patient at high risk for BRCA-1 or BRCA-2 mutation. Breast J. Nov.-Dec. 2004;10(6):475-480.
Studahl et al., Herpesvirus DNA Detection in Cerebral Spinal Fluid: Differences in Clinical Presentation between Alpha-, Beta-, and Gamma-Herpesviruses. Scand J Infect Dis. 2000;32(3):237-248.
Suzuki et al., Identification of Natural Antigenic Peptides of a Human Gastric Signet Ring Cell Carcinoma Recognized by HLA-A31-Restricted Cytotoxic T Lymphocytes. J Immunol. Sep. 1, 1999;163(5):2783-2791.
Takahashi et al., 707-AP Peptide Recognized by Human Antibody Induces Human Leukocyte Antigen A2-Restricted Cytotoxic T Lymphocyte Killing of Melanoma. Clin Cancer Res. Aug. 1997;3(8):1363-1370.
Tamura et al., Identification of Cyclophilin B-derived Peptides Capable of Inducing Histocompatibility Leukocyte Antigen-A2-restricted and Tumor-specific Cytotoxic T Lymphocytes. Jpn J Cancer Res. Jul. 2001;92(7):762-767.
Tanaka et al., Expression of Tumor-Rejection Antigens in Gynecologic Cancers. Jpn J Cancer Res. Nov. 2000;91(11):1177-1184.
Tannapfel et al., BRAF Gene Mutations Are Rare Events in Gastroenteropancreatic Neuroendocrine Tumors. Am J Clin Pathol. Feb. 2005;123(2):256-260.
Treurnicht et al., HHV-8 subtypes in South Africa: identification of a case suggesting a novel B variant. J Med Virol Feb. 2002;66(2):235-240.
Trimble et al., Comparison of the CD8+ T cell responses and antitumor effects generated by DNA vaccine administered through gene gun, biojector, and syringe. Vaccine. Sep. 8, 2003;21(25-26):4036-4042.
Trincado et al., Human Cytomegalovirus Strains Associated With Congenital and Perinatal Infections. J Med Virol. Aug. 2000;61(4):481-487.
Tsang et al., Phenotypic Stability of a Cytotoxic T-Cell Line Directed Against an Immunodominant Epitope of Human Carcinoembryonic Antigen. Clin Cancer Res. Dec. 1997;3(12 Pt 1):2439-2449.
Tsao and Sober, Melanoma Treatment Update. Dermatol Clin. Apr. 20005;23(2):323-333.
Tsuruma et al., Phase I clinical study of anti-apoptosis protein, survivin-derived peptide vaccine therapy for patients with advanced or recurrent colorectal cancer. J Transl Med. Jun. 13, 2004;2(1):19 (11 pages).
Vallejo et al., Nucleotide Sequence and Restriction Fragment-Length Polymorphism Analysis of Human T-Cell Lymphotropic Virus Type II (HTLV-II) in Southern Europe: Evidence for the HTLV-IIa and HTLV-IIb Subtypes. J Acquir Immune Defic Syndr Hum Retrovirol. Dec. 1, 1996;13(4)384-391.
Van Den Eynde et al., A New Antigen Recognized by Cytolytic T Lymphocytes on a Human Kidney Tumor Results From Reverse Strand Transcription. J Exp Med. Dec. 20, 1999;190(12):1793-1800.
Vandamme et al., African Origin of Human T-Lymphotropic Virus Type 2 (HTLV-2) Supported by a Potential New HTLV-2d Subtype in Congolese Bambuti Efe Pygmies. J Virol. May 1998;72(5):4327-4340.
Vazquez-Boland et al., Nucleotide sequence of the lecithinase operon of Listeria monocytogenes and possible role of lecithinase in cell-to-cell spread. Infect Immun. Jan. 1992;60(1):219-230.
Vilas Boas et al., Cytomegalovirus Glycoprotein B Genotypes and Central Nervous System Disease in AIDS Patients. J Med Virol. Nov. 2003;71(3):404-407.
Vilchez and Butel, Emergent Human Pathogen Simian Virus 40 and Its Role in Cancer. Clin Microbiol Rev. Jul. 2004;17(3):495-508.
Virok et al., Chlamydial Infection Induces Pathobiotype-Specific Protein Tyrosine Phosphorylation in Epithelial Cells. Infect Immun. Apr. 2005;73(4):1939-1946.
Von Lindern et al., The Translocation (6;9), Associated with a Specific Subtype of Acute Myeloid Leukemia, Results in the Fusion of Two Genes, dek and can, and the Expression of a Chimeric, Leukemia-Specific dek-can mRNA. Mol Cell Biol. Apr. 1992;12(4):1687-1697.
Wada et al., Intraperitoneal injection of in vitro expanded Vγ9Vδ2 T cells together with zoledronate for the treatment of malignant ascites due to gastric cancer. Cancer Med. Apr. 2014;3(2):362-375.
Waltregny et al., Screening of histone deacetylases (HDAC) expression in human prostate cancer reveals distinct class I HDAC profiles between epithelial and stromal cells. Eur J Histochem. Jul.-Sep. 2004;48(3):273-290.
Wang et al., Alterations of APC, c-met, and p53 Genes in Tumor Tissue and Serum of Patients with Gastric Cancers. J Surg Res. Aug. 2004;120(2):242-248.
Wang et al., Cloning Genes Encoding MHC Class II-Restricted Antigens: Mutated CDC27 as a Tumor Antigen. Science. May 21, 1999;284(5418):1351-1354.
Wang et al., Identification of a Novel Major Histocompatibility Complex Class II-restricted Tumor Antigen Resulting from a Chromosomal Rearrangement Recognized by CD4+ T Cells. J Exp Med. May 17, 1999;189(10):1659-1668.
Weaver et al., Genetic determinants of Venezuelan equine encephalitis emergence. Arch Virol Suppl. 2004; (18):43-64.

(56) References Cited

OTHER PUBLICATIONS

Weaver et al., Venezuelan Equine Encephalitis. Annu Rev Entomol. 2004;49:141-174.
Weiskirch and Paterson, Listeria monocytogenes: a potent vaccine vector for neoplastic and infectious disease. Immunol Rev. Aug. 1997;158:159-169.
Wells et al., Swine Influenza Virus Infections Transmission. From Ill Pigs to Humans at a Wisconsin Agricultural Fair and Subsequent Probable Person-to-Person Transmission. JAMA. Jan. 23-30, 1991;265(4):478-481.
Wentworth et al., An Influenza A (HINI) Virus, Closely Related to Swine Influenza Virus, Responsible for a Fatal Case of Human Influenza. J Virol. Apr. 1994;68(4):2051-2058.
Wong and Freitag, A Novel Mutation within the Central Listeria monocytogenes Regulator PrfA That Results in Constitutive Expression of Virulence Gene Products. J Bacteriol. Sep. 2004;186(18):6265-6276.
Woycechowsky and Raines, Native Disulfide Bond Formation in Proteins. Curr Opin Chem Biol. Oct. 2000;4(5):533-539.
Zaremba et al., Identification of an Enhancer Agonist Cytotoxic T Lymphocyte Peptide from Human Carcinoembryonic Antigen. Cancer Res. Oct. 15, 1997;57(20):4570-4577.
Zeier et al., New Ecological Aspects of Hantavirus Infection: A Change of a Paradigm and a Challenge of Prevention—A Review. Virus Genes. Mar. 2005;30(2):157-180.
Zimmerman et al., Expression of annexin II in conventional renal cell carcinoma is correlated with Fuhrman grade and clinical outcome. Virchows Arch. Oct. 2004;445(4):368-374.
Ziyaeyan et al., The Seroprevalence of Parvovirus BI9 Infection among To-Be-Married Girls, Pregnant Women, and Their Neonates in Shiraz, Iran. Jpn J Infect Dis. Apr. 2005;58(2):95-97.
International Preliminary Report on Patentability issued in PCT/US2015/055350 dated Apr. 27, 2017.
Abutaily et al., Cadherins, catenins and APC in pleural malignant mesothelioma. J Pathol. Nov. 2003;201(3):355-362.
Aguilar et al., Endemic Venezuelan Equine Encephalitis in Northern Peru. Emerg Infect Dis. May 2004;10(5):880-888.
Ahn et al., All CVB Serotypes and Clinical Isolates Induce Irreversible Cytopathic Effects in Primary Cardiomyocytes. J Med Virol. Feb. 2005;75(2):290-294.
Altwein and Luboldt, Prognostic Factors for Carcinoma of the Prostate. Urol Int. 1999;63(1):62-71.
Alvarez-Lafuente et al., Human parvovirus B19, varicella zoster virus, and human herpes virus 6 in temporal artery biopsy specimens of patients with giant cell arteritis: analysis with quantitative real time polymerase chain reaction. Ann Rheum Dis. May 2005;64(5):780-782.
Andersen and thor Straten, Survivin—a universal tumor antigen. Histol Histopathol. Apr. 2002;17(2):669-675.
Argani et al., Discovery of New Markers of Cancer through Serial Analysis of Gene Expression Prostate Stem Cell Antigen Is Overexpressed in Pancreatic Adenocarcinoma. Cancer Res. Jun. 1, 2001;61(11):4320-4324.
Arora et al., Identification of Differentially Expressed Genes in Oral Squamous Cell Carcinoma. Mol Carcinog. Feb. 2005;42(2):97-108.
Arslan et al., A new approach to sequence comparison: normalized sequence alignment. Bioinformatics. Apr. 2001;17(4):327-337.
Attoui et al., Comparative sequence analysis of American, European and Asian isolates of viruses in the genus Coltivirus. J Gen Virol. Oct. 1998;79 ( Pt 10)2481-2489.
Auerbuch et al., Development of a Competitive Index Assay to Evaluate the Virulence of Listeria monocytogenes actAMutants during Primary and Secondary Infection of Mice. Infect Immun. Sep. 2001;69(9):5953-5957.
Barbanti-Brodano et al., Simian virus 40 infection in humans and association with human diseases: results and hypotheses. Virology. Jan. 5, 2004;318(1):1-9.
Barthold et al., Infectivity, disease patterns, and serologic profiles of reovirus serotypes 1, 2, and 3 in infant and weanling mice. Lab Anim Sci. Oct. 1993;43(5):425-430.

Baurain et al., High Frequency of Autologous Anti-Melanoma CTL Directed Against an Antigen Generated by a Point Mutation in a New Helicase Gene. J Immunol. Jun. 1, 2000;164(11):6057-6066.
Begley et al., Analysis of the Isoprenoid Biosynthesis Pathways in Listeria monocytogenes Reveals a Role for the Alternative 2-C-Methyl-D-Erythritol 4-Phosphate Pathway in Murine Infection. Infect Immun. Nov. 2008;76(11):5392-5401.
Bevanger et al., Competitive Enzyme Immunoassay for Antibodies to a 43,000-Molecular-Weight Francisella ularensis Outer Membrane Protein for the Diagnosis of Tularemia. J Clin Microbiol. May 1989;27(5):922-926.
Bhigjee et al., Sequence of the env gene of some KwaZulu-Natal, South African strains of HTLV type I. AIDS Res Hum Retroviruses. Sep. 1, 1999;15(13):1229-1233.
Biagini et al., Simultaneous measurement of specific serum IgG responses to five select agents. Anal Bioanal Chem. Jun. 2005;382(4):1027-1034.
Bishop and Hinrichs, Adoptive transfer of immunity to Listeria monocytogenes. The influence of in vitro stimulation on lymphocyte subset requirements. J Immunol. Sep. 15, 1987;139(6):2005-2009.
Bondurant et al., Definition of an Immunogenic RegionWithin the OvarianTumor Antigen Stratum Comeum Chymotryptic Enzyme. Clin Cancer Res. May 1, 2005;11(9):3446-3454.
Brezniceanu et al., HMGB1 inhibits cell death in yeast and mammalian cells and is abundantly expressed in human breast carcinoma. Faseb J. Jul. 2003;17(10):1295-1297.
Brian and Baric, Coronavirus Genome Structure and Replication. Curr Top Microbiol Immunol. 2005;287:1-30.
Brinkmann et al., Novel Genes in the PAGE and GAGE Family of Tumor Antigens Found by Homology Walking in the dbEST Database. Cancer Res. Apr. 1, 1999;59(7):1445-1448.
Brockstedt et al., Killed but metabolically active microbes: a new vaccine paradigm for eliciting effector T-cell esponses and protective immunity. Nat Med. Aug. 2005;11(8):853-860.
Brockstedt et al., Listeria-based cancer vaccines that segregate immunogenicity from toxicity. Proc Natl Acad Sci J S A. Sep. 21, 2004;101(38):13832-13837—incl supporting information.
Bronte et al., Genetic Vaccination with "Self" Tyrosinase-related Protein 2 Causes Melanoma Eradication but not Vitiligo. Cancer Res. Jan. 15, 2000;60(2):253-258.
Brown et al., Complete Genomic Sequencing Shows that Polioviruses and Members of Human Enterovirus Species C Are Closely Related in the Noncapsid Coding Region. J Virol. Aug. 2003;77(16):8973-8984.
Brown, Variants of B19. Dev Biol (Basel). 2004;118:71-77.
Capdepont et al., New Insights in HTLV-I Phylogeny by Sequencing and Analyzing the Entire Envelope Gene. AIDS Res Hum Retroviruses. Jan. 2005;21(1):28-42.
Capurro et al., Glypican-3: A Novel Serum and Histochemical Marker for Hepatocellular Carcinoma. Gastroenterology. Jul. 2003;125(1):89-97.
Carbone et al., New developments about the association of SV40 with human mesothelioma. Oncogene. Aug. 11, 2003;22(33):5173-5180.
Chan et al., in Situ Hybridization Study of PSP94 (Prostatic Secretory Protein of 94 Amino Acids) Expression in Human Prostates. Prostate. Oct. 1, 1999;41(2):99-109.
Chang et al., A Phase I Trial of Tumor Lysate-Pulsed Dendritic Cells in the Treatment of Advanced Cancer. Clin Cancer Res. Apr. 2002;8(4):1021-1032.
Chen et al., Immunodominant CD41 responses identified in a patient vaccinated with full-length NY-ESO-1 formulated with ISCOMATRIX adjuvant. Proc Natl Acad Sci USA. Jun. 22, 2004;101(25):9363-9368.
Chern et al., Glycoprotein B Subtyping of Cytomegalovirus (CMV) in the Vitreous of Patients with AIDS and CMV Retinitis. J Infect Dis. Oct. 1998;178(4):1149-1153.
Chiari et al., Two Antigens Recognized by Autologous Cytolytic T Lymphocytes on a Melanoma Result from a Single Point Mutation in an Essential Housekeeping Gene. Cancer Res. Nov. 15, 1999;59(22):5785-5792.

(56) References Cited

OTHER PUBLICATIONS

Christiansen et al., Polarity of Prostate Specific Membrane Antigen, Prostate Stem Cell Antigen, and Prostate Specific Antigen in Prostate Tissue and in a Cultured Epithelial Cell Line. Prostate. Apr. 1, 2003;55(1):9-19.

Clements et al., Adenomatous Polyposis Coli/ß-Catenin Interaction and Downstream Targets: Altered Gene Expression in Gastrointestinal Tumors. Clin Colorectal Cancer. Aug. 2003;3(2):113-120.

Clifton et al., A chlamydial type III translocated protein is tyrosine-phosphorylated at the site of entry and associated with recruitment of actin. Proc Natl Acad Sci USA. Jul. 6, 2004;101(27):10166-10171.

Clinton et al., A Comparative Study of Four Serological Tumor Markers for the Detection of Breast Cancer. Biomed Sci Instrum. 2003;39:408-414.

Cobaleda et al., A primitive hematopoietic cell is the target for the leukemic transformation in human Philadelphia-positive acute lymphoblastic leukemia. Blood. Feb. 1, 2000;95(3):1007-1013.

Codrington et al., Analysis of ETV6/AML1 abnormalities in acute lymphoblastic leukaemia: incidence, alternative spliced forms and minimal residual disease value. Br J Haematol. Dec. 2000;111(4):1071-1079.

Creighton et al., Mechanisms and catalysts of disulfide bond formation in proteins. Trends Biotechnol. Jan. 1995;13(1):18-23.

Dalerba et al., MAGE, BAGE and GAGE gene expression in human rhabdomyosarcomas. Int J Cancer. Jul. 1, 2001;93(1):85-90.

Damasus-Awatai and Freeman-Wang, Human papilloma virus and cervical screening. Curr Opin Obstet Gynecol. Dec. 2003;15(6):473-477.

Das et al., Evaluation of a Western Equine Encephalitis recombinant E1 protein for protective immunity and diagnostics. Antiviral Res. Nov. 2004;64(2):85-92.

Davies et al., Characterisation of a recombinant Fv fragment of anti-MUC1 antibody HMFG1. Cancer Lett. Jul. 29, 1994;82(2):179-184.

De Backer et al., Characterization of the GAGE Genes That Are Expressed in Various Human Cancers and in Normal Testis. Cancer Res. Jul. 1, 1999;59(13):3157-3165.

De Villiers et al., Classification of papillomaviruses. Virology. Jun. 20, 2004;324(1):17-24.

Demidenko and Blagosklonny, Flavopiridol Induces p53 via Initial Inhibition of Mdm2 and P21 and, Independently of p53, Sensitizes Apoptosis-Reluctant Cells to Tumor Necrosis Factor. Cancer Res. May 15, 2004;64(10):3653-3660.

Disis and Cheever, HER-2/Neu Protein: A Target for Antigen-Specific Immunotherapy of Human Cancer. Adv Cancer Res. 1997;71:343-371.

Disis et al., Humoral Epitope-Spreading Following Immunization with a HER-2/neu Peptide Based Vaccine in Cancer Patients. J Clin Immunol. Sep. 2004;24(5):571-578.

Dosaka-Akita et al., Expression of N-Acetylglucosaminyltransferase V Is Associated with Prognosis and Histology n. Non-Small Cell Lung Cancers. Clin Cancer Res. Mar. 1, 2004;10(5):1773-1779.

Duxbury et al., CEACAM6 as a novel target for indirect type 1 immunotoxin-based therapy in pancreatic adenocarcinoma. Biochem Biophys Res Commun. May 7, 2004;317(3):837-843.

Elgh et al., Serological Diagnosis of Hantavirus Infections by an Enzyme-Linked Immunosorbent Assay Based on Detection of Immunoglobulin G and M Responses to Recombinant Nucleocapsid Proteins of Five Viral Serotypes. J Clin Microbiol. May 1997;35(5):1122-1130.

Engels et al., Serologic Evidence for Exposure to Simian Virus 40 in North American Zoo Workers. J Infect Dis. Dec. 15, 2004;190(12)2065-2069.

Enjoji et al., RCAS1, a Useful Serum Marker to Predict the Recurrence of Cancer: Two Cases of Cholangiocarcinoma and Pancreatic Cancer. Dig Dis Sci. Oct. 2004;49(10):1654-1656.

Ericson et al., Expression of Cyclin-Dependent Kinase 6, but not Cyclin-Dependent Kinase 4, Alters Morphology of Cultured Mouse Astrocytes. Mol Cancer Res. Jul. 2003;1(9):654-664.

Estrada-Franco et al., Venezuelan Equine Encephalitis Virus, Southern Mexico. Emerg Infect Dis. Dec. 2004;10(12):2113-2121.

Fang et al., Expression of Dnmt1, demethylase, MeCP2 and methylation of tumor-related genes in human gastric cancer. World J Gastroenterol. Dec. 1, 2004;10(23):3394-3398.

Faure et al., Inducible Hsp70 as Target of Anticancer Immunotherapy: Identification of HLA-A*0201-Restricted Epitopes. Int J Cancer. Mar. 1, 2004;108(6):863-870.

Fleishhauer et al., The DAM Gene Family Encodes a New Group of Tumor-specific Antigens Recognized by Human Leukocyte Antigen AI-restricted Cytotoxic T Lymphocytes. Cancer Res. Jul. 15, 1998;58(14):2969-2972.

Fong et al., Altered peptide ligand vaccination with Flt3 ligand expanded dendritic cells for tumor immunotherapy. Proc Natl Acad Sci U S A. Jul. 17, 2001;98(15):8809-8814.

Fuessel et al., Multiple tumor marker analyses (PSA, hK2, PSCA, trp-p8) in primary prostate cancers using quantitative RT-PCR. Int J Oncol. Jul. 2003;23(1):221-228.

Gaillard et al., Entry of L. monocytogenes into Cells Is Mediated by Internalin, a Repeat Protein Reminiscent of Surface Antigens from Gram-Positive Cocci. Cell. Jun. 28, 1991;65(7):1127-1141.

Gambus et al., Epitope mapping of a mouse monoclonal anti-MUC2 antibody suggests the existence of an immunodominant region in the COOH terminus of the MUC2 tandem-repeat sequence. Int J Cancer. Jan. 3, 1995;60(1):146-148.

Geisbert and Jahrling, Differentiation of filoviruses by electron microscopy. Virus Res. Dec. 1995;39(2-3):129-150.

Ghazizadeh et al., Role of cdk4, p16INK4, and Rb Expression in the Prognosis of Bronchioloalveolar Carcinomas. Respiration. Jan.-Feb. 2005;72(1):68-73.

Gherardi et al., Towards a new generation of vaccines: the cytokine IL-12 as an adjuvant to enhance cellular mmune responses to pathogens during prime-booster vaccination regimens. Histol Histopathol. Apr. 2001;16(2):655-667.

Gilliam et al., A phase II study of G17DT in gastric carcinoma. Eur J Surg Oncol. Jun. 2004;30(5):536-543.

Gonzalez et al., A comparative sequence analysis to revise the current taxonomy of the family Coronaviridae. Arch Virol. Nov. 2003;148(11):2207-2235.

Good et al., Development and regulation of cell-mediated immune responses to the blood stages of malaria: implications for vaccine research. Annu Rev Immunol. 2005;23:69-99.

Good et al., The immunological challenge to developing a vaccine to the blood stages of malaria parasites. Immunol Rev. Oct. 2004:201254-267.

Greiner et al., Vaccine-based Therapy Directed against Carcinoembryonic Antigen Demonstrates Antitumor Activity on Spontaneous Intestinal Tumors in the Absence of Autoimmunity. Cancer Res. Dec. 1, 2002;62(23):6944-6951.

Grimm et al., Mouse alpha-fetoprotein-specific DNA-based immunotherapy of hepatocellular carcinoma leads to tumor regression in mice. Gastroenterology. Oct. 2000;119(4):1104-1112.

Groh et al., Efficient cross-priming of tumor antigen-specific T cells by dendritic cells sensitized with diverse anti-MICA opsonized tumor cells. Proc Natl Acad Sci USA. May 320 2005;102(18):6461-6466.

Groth and Calos, Phage integrases: biology and applications. J Mol Biol. Jan. 16, 2004;335(3):667-678.

Gueguen et al., An Antigen Recognized by Autologous CTLs on a Human Bladder Carcinoma. J Immunol. Jun. 15, 1998;160(12):6188-6194.

Gulmann et al., Adenomatous Polyposis Coli Gene, beta-Catenin, and E-Cadherin Expression in Proximal and Distal Gastric Cancers and Precursor Lesions. Appl Immunohistochem Mol Morphol. Sep. 2003;11(3):230-237.

Gunn et al., Two Listeria monocytogenes Vaccine Vectors That Express Different Molecular Forms of Human Papilloma Virus-16 (HPV-16) E7 Induce Qualitatively Different T Cell Immunity That Correlates with Their Ability to Induce Regression of Established Tumors Immortalized by HPV-16. J Immunol. Dec. 1, 2001;167(11):6471-6479.

(56) References Cited

OTHER PUBLICATIONS

Gupta et al., Refolding, purification, and crystallization of apical membrane antigen 1 from Plasmodium falciparum. Protein Expr Purif. May 2005;41(1):186-198.

Haddad et al., Novel antigen identification method for discovery of protective malaria antigens by rapid testing of DNA vaccines encoding exons from the parasite genome. Infect Immun. Mar. 2004;72(3):1594-1602.

Hakansson et al., Establishment and phenotypic characterization of human U937 cells with inducible P210 BCR/ABL expression reveals upregulation of CEACAM1 (CD66a). (2004) Leukemia 18:538-547.

Harris et al., The Biological and Therapeutic Importance of Gastrin Gene Expression in Pancreatic Adenocarcinomas. Cancer Res. Aug. 15, 2004;64(16):5624-5631.

Hashido et al., Evaluation of an Enzyme-Linked Immunosorbent Assay Based on Binding Inhibition for Type-Specific Qantification of Poliovirus Neutralization-Relevant Antibodies. Microbiol Immunol. 1999;43(1):73-77.

Hassan et al., Mesothelin: A New Target for Immunotherapy. Clin Cancer Res. Jun. 15, 2004;10(12 Pt 1):3937-3942.

Havlasova et al., Mapping of immunoreactive antigens of Francisella tularensis live vaccine strain. Proteomics. Jul. 2002;2(7):857-867.

Havlasova et al., Proteomic analysis of anti-Francisella tularensis LVS antibody response in murine model of tularemia. Proteomics. May 2005;5(8):2090-2103.

He et al., Complexes of Poliovirus Serotypes with Their Common Cellular Receptor, CD155. J Virol. Apr. 2003;77(8):4827-4835.

Hirose et al., Incidence of Diffuse Large B-Cell Lymphoma of Germinal Center B-Cell Origin in Whole Diffuse Large B-Cell Lymphoma: Tissue Fluorescence In Situ Hybridization Using t(14;18) Compared with Immunohistochemistry. Int J Hematol. Jan. 2005;81(1):48-57.

Hoffman et al., Strategy for development of a pre-erythrocytic Plasmodium falciparum DNA vaccine for human use. Vaccine. Jun. 1997;15(8):842-845.

Hoke, History of U.S. Military Contributions to the Study of Viral Encephalitis. Mil Med. Apr. 2005;170(4 Suppl):92-105.

Howard et al., Differentiation of Listeria monocytogenes, Listeria innocua, Listeria ivanovii, and Listeria seeligeri by pulsed-field gel electrophoresis. Appl Environ Microbiol. Feb. 1992;58(2):709-712.

Hussain and Paterson, What is needed for effective antitumor immunotherapy? Lessons learned using Listeria monocytogenes as a live vector for HPV-associated tumors. Cancer Immunol Immunother. Jun. 2005;54(6):577-586.

Hutchinson et al., Multiplex Analysis of Cytokines in the Blood of Cynomolgus Macaques Naturally Infected With Ebola Virus (Reston Serotype). J Med Virol. Nov. 2001;65(3):561-566.

Iacobuzio-Donahue et al., Highly Expressed Genes in Pancreatic Ductal Adenocarcinomas: A Comprehensive Characterization and Comparison of the Transcription Profiles Obtained from Three Major Technologies. Cancer Res. Dec. 15, 2003;63(24):8614-8622.

Iqbal et al., BCL2 Translocation Defines a Unique Tumor Subset within the Germinal Center B-Cell-Like Diffuse Large B-Cell Lymphoma. Am J Pathol. Jul. 2004;165(1):159-166.

Isherwood et al., Vaccination strategies for Francisella tularensis. Adv Drug Deliv Rev. Jun. 17, 2005;57(9)1403-1414.

Ito et al., Prostate Carcinoma Detection and Increased Prostate-Specific Antigen Levels after 4 Years in Dutch and Japanese Males Who Had No Evidence of Disease at Initial Screening. Cancer. Jan. 15, 2005;103(2)242-250.

Jainkittivong and Langlais, Herpes B virus infection. Oral Surg Oral Med Oral Pathol Oral Radiol Endod. Apr. 1998;85(4):399-403.

Frencher et al., "HMBPP-deficient Listeria mutant immunization alters pulmonary/systemic responses, effector functions, and memory polarization of Vγ2Vδ2 T cells", J Leukoc Biol. Dec. 2014;96(6):957-67. doi: 10.1189/ilb.6HI1213-632R. Epub Aug. 11, 2014.

Ryan-Payseur et al., "Multieffector-functional immune responses of HMBPP-specific Vγ2Vδ2 T cells in nonhuman primates inoculated with Listeria monocytogenes ΔactA prfA*", J Immunol. Aug. 1, 2012;189(3):1285-93. doi: 10.A049/immunol.1200641. Epub Jun. 27, 2012.

Workalemahu et al., "Metabolic engineering of Salmonella vaccine bacteria to boost human Vγ2Vδ2 T cell immunity", J Immunol. Jul. 15, 2014;193(2):708-21. doi: 10.4049/jimmunol.1302746. Epub Jun 18, 2014.

International Search Report and Written Opinion issued in PCT/US2015/055350 dated Jan. 12, 2016 (10 pages).

Jamieson et al., Human Torovirus: A New Nosocomial Gastrointestinal Pathogen. J Infect Dis. Nov. 1998;178(5):1263-1269.

Jansen and Shaw, Human Papillomavirus Vaccines and Prevention of Cervical Cancer. Annu Rev Med. 2004;55:319-331.

Johnson et al., Natural Atypical Listeria innocua Strains with Listeria monocytogenes Pathogenicity Island 1 Genes. Appl Environ Microbiol. Jul. 2004;70(7):4256-4266.

Jones and Portnoy, Characterization of Listeria monocytogenes pathogenesis in a strain expressing perfringolysin O in place of listeriolysin O. Infect Immun. Dec. 1994;62(12):5608-5613.

Jung et al., Strategies Against Human Papillomavirus Infection and Cervical Cancer. J Microbiol. Dec. 2004;42(4):255-266.

Jungck et al., E-cadherin expression is homogeneously reduced in adenoma from patients with familial adenomatous polyposis: an immunohistochemical study of E-cadherin, beta-catenin and cyclooxygenase-2 expression. Int J Colorectal Dis. Sep. 2004;19(5):438-445.

Kann and Goldstein, Performance Evaluation of a New Algorithm for the Detection of Remote Homologs With Sequence Comparison. Proteins. Aug. 1, 2002;48(2):367-376.

Kaufman et al., Parvovirus B19 does not bind to membrane-associated globoside in vitro. Virology. Feb. 5, 2005;332(1):189-198.

Kedl et al., Comparative Sequence Analysis of the Reovirus S4 Genes from 13 Serotype 1 and Serotype 3 Field Isolates. J Virol. Jan. 1995;69(1):552-559.

Kim et al., Comparison of HPV DNA vaccines employing intracellular targeting strategies. Gene Ther. Jun. 2004;11(12)1011-1018.

Krzych et al., T lymphocytes from volunteers immunized with irradiated Plasmodium falciparum sporozoites recognize liver and blood stage malaria antigens. J Immunol. Oct. 15, 1995;155(8):4072-4077.

Kubuschok et al., Expression of cancer testis antigens in pancreatic carcinoma cell lines, pancreatic adenocarcinoma and chronic pancreatitis. Int J Cancer. Apr. 20, 2004;109(4):568-575.

Kumamuru et al., T-cell receptor Vbeta gene usage by T cells reactive with the tumor-rejection antigen SART-1 in oral squamous cell carcinoma. Int J Cancer. Feb. 20, 2004;108(5):686-695.

Kyte and Doolittle, A Simple Method for Displaying the Hydropathic Character of a Protein. J Mol Biol. May 5, 1982;157(1)105-132.

Laheru and Jaffee, Immunotherapy for pancreatic cancer—science driving clinical progress. Nat Rev Cancer. Jun. 2005;5(6):459-467.

Lalic-Multhaler et al., In vitro transcription of PrfA-dependent and -independent genes of Listeria monocytogenes. Mol Microbiol. Oct. 2001;42(1):111-120.

Lauer et al., Constitutive Activation of the PrfA Regulon Enhances the Potency of Vaccines Based on Live-Attenuated and Killed but Metabolically Active Listeria monocytogenes Strains. Infect Immun. Aug. 2008;76(8)3742-3753.

Lauer et al., Construction, Characterization, and Use of Two Listeria monocytogenes Site-Specific Phage Integration Vectors. J Bacteriol. Aug. 2002;184(15):4177-4186.

Le et al., A Live-Attenuated Listeria Vaccine (ANZ-100) and a Live-Attenuated Listeria Vaccine Expressing Mesothelin (CRS-207) for Advanced Cancers: Phase I Studies of Safety and Immune Induction. Clin Cancer Res. Feb. 1, 2012;18(3):858-868.

Lee et al., Immunomic analysis of human sarcoma. Proc Natl Acad Sci USA. Mar. 4, 2003;100(5):2651-2656.

Leroux-Roels et al., Prevention of Hepatitis B Infections: Vaccination and its Limitations. Acta Clin Belg. Jul.-Aug. 2001;56(4):209-219.

Li et al., Advanced Glycation End Products Induce Tubular Epithelial-Myofibroblast Transition through the RAGE-ERK1/2 MAP Kinase Signaling Pathway. Am J Pathol. Apr. 2004;164(4):1389-1397.

(56) References Cited

OTHER PUBLICATIONS

Li et al., Expression Profile of Cancer-Testis Genes in 121 Human Colorectal Cancer Tissue and Adjacent Normal Tissue. Clin Cancer Res. Mar. 1, 2005;11(5):1809-1814.
Liang et al., Microvessel density, cyclo-oxygenase 2 expression, K-ras mutation and p53 overexpression in colonic cancer Br J Surg. Mar. 2004;91(3):355-361.
Liau et al., Tumor Immunity within the Central Nervous System Stimulated by Recombinant Listeria monocytogenes Vaccination. Cancer Res. Apr. 15, 2002;62(8):2287-2293.
Lim et al., Molecular and phenotypic spectrum of de novo Philadelphia positive acute leukemia. Int J Mol Med. Dec. 1999;4(6):665-667.
Lin et al , Melanoma-Associated Antigens in Esophageal Adenocarcinoma Identification of Novel MAGE-A10 Splice Variants. Clin Cancer Res. Sep. 1, 2004;10(17):5708-5716.
Lingnau et al., Expression of the Listeria monocytogenes EGD inIA and inIB genes, whose products mediate bacterial entry into tissue culture cell lines, by PrfA-dependent and -independent mechanisms. Infect Immun. Oct. 1995;63(10):3896-3903.
Lucas et al., MAGE-B5, MAGE-B6, MAGE-C2, and MAGE-C3: four new members of the MAGE family with tumor-specific expression. Int J Cancer. Jul. 1, 2000;87(1):55-60.
Luo et al., In vitro transcription of the Listeria monocytogenes virulence genes inIC and mpl reveals overlapping PrfA-dependent and -independent promoters that are differentially activated by GTP. Mol Microbiol. Apr. 2004;52(1):39-52.
Machlenkin et al., Human CTL Epitopes Prostatic Acid Phosphatase-3 and Six-Transmembrane Epithelial Antigen of Prostate-3 as Candidates for Prostate Cancer Immunotherapy. Cancer Res. Jul. 15, 2005;65(14):6435-6442.
Mandruzzato et al., A CASP-8 Mutation Recognized by Cytolytic T Lymphocytes on a Human Head and Neck Carcinoma. J Exp Med. Aug. 29, 1997;186(5):785-793.
Marth, Booster Policy for Adults. Biologicals. Jun. 1997;25(2):199-203.
Matsumoto et al., Expression of the SART-1 antigens in uterine cancers. Jpn J Cancer Res. Dec. 1998;89(12):1292-1295.
Matsushita et al., Preferentially Expressed Antigen of Melanoma (PRAME) in the Development of Diagnostic and Therapeutic Methods for Hematological Malignancies. Leuk Lymphoma. Mar. 2003;44(3):439-444.
Mayo et al., Mdm-2 Phosphorylation by DNA-dependent Protein Kinase Prevents Interaction with p53. Cancer Res. Nov. 15, 1997;57(22):5013-5016.
McCool et al., Roles of calreticulin and calnexin during mucin synthesis in LS180 and HT29/A1 human colonic adenocarcinoma cells. Biochem J. Aug. 1, 1999;341 ( Pt 3):593-600.
McCune et al., Active specific immunotherapy with tumor cells and Corynebacterium parvum: A phase I study. Cancer. May 1979;43(5):1619-1623.
Millon et al., Detection of Prostate-Specific Antigen- or Prostate-Specific Membrane Antigen-Positive Circulating Cells in Prostatic Cancer Patients: Clinical Implications. Eur Urol. Oct. 1999;36(4):278-285.

Molijn et al., Molecular diagnosis of human papillomavirus (HPV) infections. J Clin Virol. Mar. 2005;32 Suppl 1: S43-51.
Moreau-Aubry et al., A Processed Pseudogene Codes for a New Antigen Recognized by a Cd8+ T Cell Clone on Melanoma. J Exp Med. May 1, 2000;191(9):1617-1624.
Morse et al., A Phase I Study of Active Immunotherapy with Carcinoembryonic Antigen Peptide (CAP-1)-pulsed, Autologous Human Cultured Dendritic Cells in Patients with Metastatic Malignancies Expressing Carcinoembryonic Antigen. Clin Cancer Res. Jun. 1999;5(6):1331-1338.
Mueller and Freitag, Pleiotropic Enhancement of Bacterial Pathogenesis Resulting from the Constitutive Activation of the Listeria monocytogenes Regulatory Factor PrfA. Infect Immun. Apr. 2005;73(4):1917-1926.
Mukhopadhyay et al., A structural perspective of the flavivirus life cycle. Nat Rev Microbiol. Jan. 2005;3(1):13-22.
Mulders et al., Tumor antigens and markers in renal cell carcinoma. Urol Clin North Am. Aug. 2003;30(3):455-465.
Muller et al., MeCP2 and MBD2 expression in human neoplastic and non-neoplastic breast tissue and its association with oestrogen receptor status. Br J Cancer. Nov. 17, 2003;89(10):1934-1939.
Muminova et al., Characterization of human mesothelin transcripts in ovarian and pancreatic cancer. BMC Cancer. May 12, 2004;4:19.
Munsen and Rodbard, Ligand: A Versatile Computerized Approach for Characterization of Ligand-Binding Systems. Anal Biochem. Sep. 1, 1980;107(1):220-239.
Nair et al., Induction of cytotoxic T cell responses and tumor immunity against unrelated tumors using telomerase reverse transcriptase RNA transfected dendritic cells. Nat Med. Sep. 2000;6(9):1011-1017.
Nakatsura et al., Cellular and humoral immune responses to a human pancreatic cancer antigen, coactosin-like protein, originally defined by the SEREX method. Eur J Immunol. Mar. 2002;32(3):826-836.
Workalemahu et al., "Metabolic Engineering of Salmonella Vaccine Bacteria to Boost Human V?2V?2 T Cell Immunity" J. Immunol. Jul. 15, 2014; 193(2): 708-721. doi:10.4049/jimmunol.1302746.
Maniar et al., "Human gammadelta T lymphocytes induce robust NK cell-mediated antitumor cytotoxicity through CD137 engagement", Blood. Sep. 9, 2010;116(10)1726-33. doi: 10.1182/blood-2009-07-234211.
Vantourout et al., "Six-of-the-best: unique contributions of γδ T cells to immunology", Nat Rev Immunol. Feb. 2013;13(2):88-100. doi: 10.1038/nri3384.
Khan et al., "Expanded Human Blood-Derived γδT Cells Display Potent Antigen-Presentation Functions", Front Immunol. Jul. 23, 2014;5:344. doi: 10.3389/fimmu.2014.00344.
Petrasca and Doherty, "Human Vδ2(+) γδ T Cells Differentially Induce Maturation, Cytokine Production, and Alloreactive T Cell Stimulation by Dendritic Cells and B Cells", Front Immunol. Dec. 19, 2014;5:650. doi: 10.3389/fimmu.2014.00650.
Hoeres et al., "Improving the Efficiency of Vγ9Vδ2 T-Cell Immunotherapy in Cancer", Front Immunol. Apr. 19, 2018;9:800. doi: 10.3389/fimmu.2018.00800.
Gogoi and Chiplunkar, "Targeting gamma delta T cells for cancer immunotherapy: bench to bedside", Indian J Med Res. Nov. 2013;138(5):755-61.

* cited by examiner

SEQUENCE LISTING

<160> NUMBER OF SEQ ID NOS: 42

<210> SEQ ID NO 1
<211> LENGTH: 25
<212> TYPE: PRT
<213> ORGANISM: Artificial Sequence
<220> FEATURE:
<223> OTHER INFORMATION: Synthetic:  LLO signal sequence

<400> SEQUENCE: 1

Met Lys Lys Ile Met Leu Val Phe Ile Thr Leu Ile Leu Val Ser Leu
1               5                   10                  15

Pro Ile Ala Gln Gln Thr Glu Ala Lys
            20                  25

<210> SEQ ID NO 2
<211> LENGTH: 441
<212> TYPE: PRT

<213> ORGANISM: Artificial Sequence
<220> FEATURE:
<223> OTHER INFORMATION: Synthetic: LLO-N441 sequence

<400> SEQUENCE: 2

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
                100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
```

-continued

```
                385                 390                 395                 400
Lys Asn Asn Ser Glu Tyr Ile Glu Thr Thr Ser Lys Ala Tyr Thr Asp
                    405                 410                 415
Gly Lys Ile Asn Ile Asp His Ser Gly Tyr Val Ala Gln Phe Asn
                420                 425                 430
Ile Ser Trp Asp Glu Val Asn Tyr Asp
                435                 440

<210> SEQ ID NO 3
<211> LENGTH: 100
<212> TYPE: PRT
<213> ORGANISM: Artificial Sequence
<220> FEATURE:
<223> OTHER INFORMATION: Synthetic: ActA-N100

<400> SEQUENCE: 3

Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Glu Lys Thr
            35                  40                  45

Glu Glu Gln Pro Ser Glu Val Asn Thr Gly Pro Arg Tyr Glu Thr Ala
        50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly
            100

<210> SEQ ID NO 4
<211> LENGTH: 100
<212> TYPE: PRT
<213> ORGANISM: Artificial Sequence
<220> FEATURE:
<223> OTHER INFORMATION: Synthetic: ActA-N100

<400> SEQUENCE: 4

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Glu Lys Thr
            35                  40                  45

Glu Glu Gln Pro Ser Glu Val Asn Thr Gly Pro Arg Tyr Glu Thr Ala
        50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly
            100

<210> SEQ ID NO 5
<211> LENGTH: 102
<212> TYPE: PRT
<213> ORGANISM: Artificial Sequence
<220> FEATURE:
```

<223> OTHER INFORMATION: Synthetic: ActA-N100 extended by two residues
      added by inclusion of BamH1

<400> SEQUENCE: 5

```
Val Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly Gly Ser
            100
```

<210> SEQ ID NO 6
<211> LENGTH: 102
<212> TYPE: PRT
<213> ORGANISM: Artificial Sequence
<220> FEATURE:
<223> OTHER INFORMATION: Synthetic: ActA-N100 extended by two residues
      added by inclusion of BamH1

<400> SEQUENCE: 6

```
Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly Gly Ser
            100
```

<210> SEQ ID NO 7
<211> LENGTH: 29
<212> TYPE: DNA
<213> ORGANISM: Artificial Sequence
<220> FEATURE:
<223> OTHER INFORMATION: Synthetic primer: DXS1

<400> SEQUENCE: 7
ggtcgacgat tactcacgct tgatggggc                                      29

<210> SEQ ID NO 8
<211> LENGTH: 30
<212> TYPE: DNA
<213> ORGANISM: Artificial Sequence
<220> FEATURE:
<223> OTHER INFORMATION: Synthetic primer: DXS2

<400> SEQUENCE: 8
ggatccttcc ttctccacct gtaataggtg                                    30

<210> SEQ ID NO 9
<211> LENGTH: 48
<212> TYPE: DNA
<213> ORGANISM: Artificial Sequence
<220> FEATURE:
<223> OTHER INFORMATION: Synthetic primer: DXS3

<400> SEQUENCE: 9
tcatagtctc ttcgccctta acttaagatc caaataaaaa caactcac                48

<210> SEQ ID NO 10
<211> LENGTH: 48
<212> TYPE: DNA
<213> ORGANISM: Artificial Sequence
<220> FEATURE:
<223> OTHER INFORMATION: Synthetic primer: DXS4

<400> SEQUENCE: 10
gtgagttgtt tttatttgga tcttaagtta agggcgaaga gactatga                48

<210> SEQ ID NO 11
<211> LENGTH: 25
<212> TYPE: DNA
<213> ORGANISM: Artificial Sequence
<220> FEATURE:
<223> OTHER INFORMATION: Synthetic primer: DXSINT-FOR

<400> SEQUENCE: 11
gcgagtgtgt tagaatttat agaag                                         25

<210> SEQ ID NO 12
<211> LENGTH: 24
<212> TYPE: DNA
<213> ORGANISM: Artificial Sequence
<220> FEATURE:
<223> OTHER INFORMATION: Synthetic primer: DXSINT-REV

<400> SEQUENCE: 12
cccaaataaa tttatctttt ggac                                          24

<210> SEQ ID NO 13
<211> LENGTH: 31
<212> TYPE: DNA
<213> ORGANISM: Artificial Sequence
<220> FEATURE:
<223> OTHER INFORMATION: Synthetic primer: DXR1

<400> SEQUENCE: 13
ggtcgacttg caactattgc attatatgaa g                                  31

<210> SEQ ID NO 14
<211> LENGTH: 30
<212> TYPE: DNA
<213> ORGANISM: Artificial Sequence
<220> FEATURE:
<223> OTHER INFORMATION: Synthetic primer: DXR2

<400> SEQUENCE: 14
ggatcccatt gatggaaaga acttcatccc                                    30

<210> SEQ ID NO 15
<211> LENGTH: 48
<212> TYPE: DNA

```
<213> ORGANISM: Artificial Sequence
<220> FEATURE:
<223> OTHER INFORMATION: Synthetic primer: DXR3

<400> SEQUENCE: 15
ctataaaagt gtctttacat acgcacctag caaaataatt tttttcat                48

<210> SEQ ID NO 16
<211> LENGTH: 48
<212> TYPE: DNA
<213> ORGANISM: Artificial Sequence
<220> FEATURE:
<223> OTHER INFORMATION: Synthetic primer: DXR4

<400> SEQUENCE: 16
atgaaaaaaa ttattttgct aggtgcgtat gtaaagacac ttttatag                48

<210> SEQ ID NO 17
<211> LENGTH: 24
<212> TYPE: DNA
<213> ORGANISM: Artificial Sequence
<220> FEATURE:
<223> OTHER INFORMATION: Synthetic primer: DXRINT-FOR

<400> SEQUENCE: 17
aaataggtgg aacaatgccg acag                                          24

<210> SEQ ID NO 18
<211> LENGTH: 24
<212> TYPE: DNA
<213> ORGANISM: Artificial Sequence
<220> FEATURE:
<223> OTHER INFORMATION: Synthetic primer: DXRINT-REV

<400> SEQUENCE: 18
gcttctaagg taacacgatc tctc                                          24

<210> SEQ ID NO 19
<211> LENGTH: 31
<212> TYPE: DNA
<213> ORGANISM: Artificial Sequence
<220> FEATURE:
<223> OTHER INFORMATION: Synthetic primer: YGBP1

<400> SEQUENCE: 19
ggtcgacgta tcggaattag tcgtcgtaac g                                  31

<210> SEQ ID NO 20
<211> LENGTH: 30
<212> TYPE: DNA
<213> ORGANISM: Artificial Sequence
<220> FEATURE:
<223> OTHER INFORMATION: Synthetic primer: YGBP2

<400> SEQUENCE: 20
ggatccacat ccacgccttc atcccagtcc                                    30

<210> SEQ ID NO 21
<211> LENGTH: 48
<212> TYPE: DNA
<213> ORGANISM: Artificial Sequence
<220> FEATURE:
<223> OTHER INFORMATION: Synthetic primer: YGBP3

<400> SEQUENCE: 21
ctaatcattt gctatccctc caagaaccaa ctcataattc atgctcat                48
```

```
<210> SEQ ID NO 22
<211> LENGTH: 48
<212> TYPE: DNA
<213> ORGANISM: Artificial Sequence
<220> FEATURE:
<223> OTHER INFORMATION: Synthetic primer: YGBP4

<400> SEQUENCE: 22
atgagcatga attatgagtt ggttcttgga gggatagcaa atgattag                48

<210> SEQ ID NO 23
<211> LENGTH: 25
<212> TYPE: DNA
<213> ORGANISM: Artificial Sequence
<220> FEATURE:
<223> OTHER INFORMATION: Synthetic primer: YGBPINT-FOR

<400> SEQUENCE: 23
ctgcctattt tacgaaaagc gcatc                                         25

<210> SEQ ID NO 24
<211> LENGTH: 23
<212> TYPE: DNA
<213> ORGANISM: Artificial Sequence
<220> FEATURE:
<223> OTHER INFORMATION: Synthetic primer: YGBPINT-REV

<400> SEQUENCE: 24
attcttttac atgctttctt tcc                                           23

<210> SEQ ID NO 25
<211> LENGTH: 29
<212> TYPE: DNA
<213> ORGANISM: Artificial Sequence
<220> FEATURE:
<223> OTHER INFORMATION: Synthetic primer: YGBB1

<400> SEQUENCE: 25
ggtcgacatg agcatgaatt atgagttgg                                     29

<210> SEQ ID NO 26
<211> LENGTH: 30
<212> TYPE: DNA
<213> ORGANISM: Artificial Sequence
<220> FEATURE:
<223> OTHER INFORMATION: Synthetic primer: YGBB2

<400> SEQUENCE: 26
ggatcccata tcgttgaaag taatcgtttc                                    30

<210> SEQ ID NO 27
<211> LENGTH: 48
<212> TYPE: DNA
<213> ORGANISM: Artificial Sequence
<220> FEATURE:
<223> OTHER INFORMATION: Synthetic primer: YGBB3

<400> SEQUENCE: 27
caagtaagac aacggctaga cttgataacc ttggccaatt ctaatcat                48

<210> SEQ ID NO 28
<211> LENGTH: 48
<212> TYPE: DNA
<213> ORGANISM: Artificial Sequence
<220> FEATURE:
```

<223> OTHER INFORMATION: Synthetic primer: YGBB4

<400> SEQUENCE: 28
atgattagaa ttggccaagg ttatcaagtc tagccgttgt cttacttg          48

<210> SEQ ID NO 29
<211> LENGTH: 23
<212> TYPE: DNA
<213> ORGANISM: Artificial Sequence
<220> FEATURE:
<223> OTHER INFORMATION: Synthetic primer: YGBBINT-FOR

<400> SEQUENCE: 29
gctgaaaagc aaaaatggc gcc          23

<210> SEQ ID NO 30
<211> LENGTH: 25
<212> TYPE: DNA
<213> ORGANISM: Artificial Sequence
<220> FEATURE:
<223> OTHER INFORMATION: Synthetic primer: YGBBINT-REV

<400> SEQUENCE: 30
tgaccaatat caccagcacc aattg          25

<210> SEQ ID NO 31
<211> LENGTH: 31
<212> TYPE: DNA
<213> ORGANISM: Artificial Sequence
<220> FEATURE:
<223> OTHER INFORMATION: Synthetic primer: YCHB1

<400> SEQUENCE: 31
ggtcgacgct caaagaagaa aaacgctttg g          31

<210> SEQ ID NO 32
<211> LENGTH: 30
<212> TYPE: DNA
<213> ORGANISM: Artificial Sequence
<220> FEATURE:
<223> OTHER INFORMATION: Synthetic primer: YCHB2

<400> SEQUENCE: 32
ggatccggcc taaatatgct tgtagttctc          30

<210> SEQ ID NO 33
<211> LENGTH: 48
<212> TYPE: DNA
<213> ORGANISM: Artificial Sequence
<220> FEATURE:
<223> OTHER INFORMATION: Synthetic primer: YCHB3

<400> SEQUENCE: 33
gtatcgttct cgccttcact ccattggtgc tgtaatgctt attttcat          48

<210> SEQ ID NO 34
<211> LENGTH: 48
<212> TYPE: DNA
<213> ORGANISM: Artificial Sequence
<220> FEATURE:
<223> OTHER INFORMATION: Synthetic primer: YCHB4

<400> SEQUENCE: 34
atgaaaataa gcattacagc accaatggag tgaaggcgag aacgatac          48

<210> SEQ ID NO 35
<211> LENGTH: 23
<212> TYPE: DNA
<213> ORGANISM: Artificial Sequence
<220> FEATURE:
<223> OTHER INFORMATION: Synthetic primer: YCHBINT-FOR

<400> SEQUENCE: 35
gttagcgttt ggtgctgagg cgg                                    23

<210> SEQ ID NO 36
<211> LENGTH: 24
<212> TYPE: DNA
<213> ORGANISM: Artificial Sequence
<220> FEATURE:
<223> OTHER INFORMATION: Synthetic primer: YCHB INT-REV

<400> SEQUENCE: 36
acgatcttct ggaataaagt gcgc                                   24

<210> SEQ ID NO 37
<211> LENGTH: 32
<212> TYPE: DNA
<213> ORGANISM: Artificial Sequence
<220> FEATURE:
<223> OTHER INFORMATION: Synthetic primer: GcpE1

<400> SEQUENCE: 37
ggtcgaccct atctcgattg atcaagatga ac                          32

<210> SEQ ID NO 38
<211> LENGTH: 30
<212> TYPE: DNA
<213> ORGANISM: Artificial Sequence
<220> FEATURE:
<223> OTHER INFORMATION: Synthetic primer: GcpE2

<400> SEQUENCE: 38
ggatccgcta gttcaggtgt cataactcgc                             30

<210> SEQ ID NO 39
<211> LENGTH: 48
<212> TYPE: DNA
<213> ORGANISM: Artificial Sequence
<220> FEATURE:
<223> OTHER INFORMATION: Synthetic primer: GcpE3

<400> SEQUENCE: 39
cgattatcta aggctttcca aatcttggac tgggcgagtg ttttcgcg         48

<210> SEQ ID NO 40
<211> LENGTH: 48
<212> TYPE: DNA
<213> ORGANISM: Artificial Sequence
<220> FEATURE:
<223> OTHER INFORMATION: Synthetic primer: GcpE4

<400> SEQUENCE: 40
cgcgaaaaca ctcgcccagt ccaagatttg gaaagcctta gataatcg         48

<210> SEQ ID NO 41
<211> LENGTH: 24
<212> TYPE: DNA
<213> ORGANISM: Artificial Sequence
<220> FEATURE:
<223> OTHER INFORMATION: Synthetic primer: GcpE-int-Rev

```
<400> SEQUENCE: 41
gcaagtaggg caggagataa gcat                                              24

<210> SEQ ID NO 42
<211> LENGTH: 23
<212> TYPE: DNA
<213> ORGANISM: Artificial Sequence
<220> FEATURE:
<223> OTHER INFORMATION: Synthetic primer:  GcpE-int-For

<400> SEQUENCE: 42
attcaccgat tagaagaagc tgg                                               23
```

BACTERIAL VACCINES DEFICIENT IN THE 2-C-METHYL-D-ERYTHRITOL-4-PHOSPHATE PATHWAY AND METHODS OF PREPARATION AND USE THEREOF

CROSS-REFERENCE TO RELATED APPLICATIONS

The present invention is filed under 35 U.S.C. § 371 as the U.S. national phase of International Patent Application No. PCT/US2015/055350, filed Oct. 13, 2015, which designated the United States and claims priority to U.S. Provisional Application No. 62/063,351, filed Oct. 13, 2014, each of which is hereby incorporated in its entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Apr. 13, 2017, is named PROV_001_US_SeqListing.txt and is 16 kilobytes in size

BACKGROUND OF THE INVENTION

The following discussion of the background of the invention is merely provided to aid the reader in understanding the invention and is not admitted to describe or constitute prior art to the present invention.

Pathogenic organisms are, by definition, capable of causing disease in an infected host. For clinical use of such organisms, attenuated vaccine strains are often created which exhibit reduced or eliminated virulence, but which still retain sufficient viability to stimulate a desired immune response against the pathogen or heterologous antigen(s) of interest. Attenuated vector platforms have been demonstrated to elicit protective responses specific for encoded heterologous antigens in a number of experimental models, including infectious and malignant diseases. Although most attenuated vaccine vectors are viral, bacterial vaccine vector platforms have been developed for both prophylactic and therapeutic applications. Attenuated strains of many otherwise pathogenic bacteria are now available and the ease of manipulation for generating recombinant strains provides a means for using bacteria as efficacious delivery vehicles for a number of foreign proteins such as antigens associated with infectious diseases and cancer. Bacterial vaccine strains have been developed from eubacterial species including *Listeria, Escherichia, Salmonella, Shigella, Lactobacillus*, and *Yersinia*.

Isoprenoids are essentially involved in the metabolism of all organisms as in electron transfer, photosynthesis, membrane stability, and cell signaling. In animals, fungi, archaebacteria, and certain eubacteria, biosynthesis of isopentenyl diphosphate (IPP) and its isomer dimethylallyl diphosphate (DMAPP), the precursors of all isoprenoids, proceeds exclusively via the mevalonate pathway. In contrast, in many eubacteria, IPP and DMAPP are synthesized via an alternative pathway, referred to herein as the 2-C-methyl-D-erythritol-4-phosphate (MEP) pathway. The pathway is initiated by the formation of 1-deoxy-D-xylulose-5-phosphate (DOXP) through condensation of pyruvate and D-glyceraldehyde-3-phosphate by DOXP synthase (Dxs). DOXP is then converted into MEP by DOXP reductoisomerase (Dxr, EC 1.1.1.267). The enzymes encoded by the genes ygbP (ispD, EC 2.7.7.60), ychB (ispE, EC 2.7.1.148), and ygbB (ispF, EC 4.6.1.12) mediate the formation of 2-C-methyl-D-erythritol-2,4-cyclodiphosphate (MEcPP) via three additional reaction steps. The terminal steps of the MEP pathway involve the bacterial encoded gcpE and lytB gene products.

*Listeria monocytogenes* possesses the genetic capacity to produce the complete set of enzymes involved in both the mevalonate pathway and the alternative MEP pathway. In *Listeria* mutant strains in which both pathways are defective are auxotrophic and have been reported to require exogenous mevalonate for growth. In contrast, murine studies revealed that mutants lacking the MEP pathway were impaired in virulence relative to the parent strain during intraperitoneal infection, while mutants lacking the classical mevalonate pathway were not impaired in virulence potential. Begley et al., Infect Immun. 76: 5392-401, 2008 (doi: 10.1128/IAI.01376-07).

These studies in mice, however, do not reflect the situation when a bacterium harboring a disrupted MEP pathway is administered to a primate. Primate γδ T cells recognize the HMBPP phospho-antigen derived from various bacteria and provoke adaptive immunity in various ways. They reportedly expand during bacterial infections resulting in tuberculosis, *salmonellosis*, tularemia, brucellosis, listeriosis, and ehrlichiosis. Activated and expanded Vγ2Vδ2+ T cells specifically recognize HMBPP in a TCR-dependent, MHC-, and CD1-unrestricted manner, and then mediate resistance to bacteria. γδ T cells are also increased in non-bacterial conditions such as acute *Plasmodium falciparum* malaria and acute infection with *Trypanosoma cruzi*. In contrast, mice lack a counterpart of human Vγ9Vδ2 T cells and thus cannot respond to IPP. In addition, Vγ9Vδ2 T-cells are highly desirable in cancer therapy because these cells can secrete cytokines and exert potent cytotoxicity against a wide range of cancer cells. Thus, disruption of the MEP pathway would not appear to be a suitable strategy for purposes of bacterially-based cancer vaccines. Wada et al., Cancer Med. 3: 362-75, 2014.

There remains a need in the art to provide bacterial vaccine strains with advantageous therapeutic profiles for use treatment or prevention of diseases.

BRIEF SUMMARY OF THE INVENTION

The present invention relates to the preparation and use in primates of whole organismvaccines in which the MEP pathway is disrupted such that synthesis of HMBPP by the bacterial cells is substantially blocked. Unexpectedly, the data provided below demonstrate that, when bacteria or other vaccine vectors that comprise an active MEP pathway are used in vaccine methods, the γδ T cell response dominates, potentially clearing the vaccine strain via γδ T cell-mediated killing of vector infected antigen presenting cells and reducing its utility as a stimulator of a productive adaptive immune response, specifically priming or boosting of $CD4^+$ and $CD8^+$ αβ T cell responses, specific for listerial-encoded antigens. By disrupting the MEP pathway, activation and expansion of γδ T cells is limited in the recipient primate, resulting in resulting in an increase in the magnitude and duration of inflammation and in the magnitude and duration of antigen presentation by the cellular vaccine.

The present invention relates, in various aspects, to methods of providing a bacterium or other cellular vaccine strain such as *Plasmodium falciparum* or *Trypanosoma cruzi* to delete one or more genes in the bacterial genome which are essential for HMBPP production by the cellular vaccine strain (e.g., bacteria), cells produced by such methods, and methods by which such cells are used as vaccine strains.

As described hereinafter, the cells of the present invention are provided by disrupting one or more genes which encode a protein selected from the group consisting of DOXP synthase, DOXP reductase, CDP-ME synthase, CDP-ME kinase, MEcPP synthase, and HMB-PP synthase. Such disruption may be produced by knockout of an entire gene, by disruption of control elements such as promoters, by introduction of a stop codon, by introduction of missense mutations resulting in a non-functional protein, by partial gene deletion resulting in a non-functional protein, by insertion of group II introns, etc. This list is not meant to be limiting.

The cells selected for modification in this manner most preferably comprises an active mevalonate pathway. In those cells lacking an active mevalonate pathway in a wild type state, enzymes which comprise the mevalonate pathway may be added by recomninant means, or exogenous mevalonate may be provided during growth in vitro in order to produce sufficient bacteria for use as a vaccine.

Preferred cells for modification according to the present invention are bacterial genuses selected from the group consisting of *Listeria, Neisseria, Mycobacterium, Francisella, Bacillus, Salmonella, Shigella, Yersinia, Brucella, Streptococci, Legionella, Rickettsia*, and *Chlamydia*. This list is not meant to be limiting. Most preferably, the bacterium is a facultative intracellular bacterium such as *Listeria, Salmonella, Shigella, Francisella, Mycobacterium, Legionella, Burkholderia* and *Brucella*. Most preferably, the bacterium is *Listeria monocytogenes*. Other cells which may be modified are any cells which are desirable for use as a cellular vaccine and which comprise a pathway for HMBPP production, such as *Plasmodium falciparum* or *Trypanosoma cruzi*.

The phrase "substantially blocked HMBPP production" as used herein refers to a bacterium or other cell in which HMBPP production no more that 10% of that of a corresponding cell which is otherwise identical, but which lacks the disruption in the MEP pathway. For convenience, such a cell which lacks the recombinantly introduced gene disruption(s) are referred to herein as a "wild type" cell. Most preferably, HMBPP production is no more than 5%, and most preferably no more than 1%, as compared to a bacterium or other cell which is otherwise identical, but which lacks the disruption in the MEP pathway.

The term "host organism" as used herein refers to an organism in which the bacterium of interest has been administered. As noted, a host organism is a primate species, most preferably a human.

In certain embodiments, the bacterium is utilized as an expression platform for expressing one or more genes which are heterologous to the bacterium, for example for purposes of generating an immune response to the heterologous proteins expressed from those genes. In these embodiments, the bacterium can comprise within the bacterial genome an exogenous nucleic acid sequence encoding a heterologous polypeptide(s), wherein the exogenous nucleic acid sequence is operably connected to regulatory sequences which induce expression of the heterologous polypeptide by the bacterium. Thus, in a related aspect, the invention provides a method for stimulating an immune response to an antigen in a primate comprising administering an effective amount of a bacterium as described herein to the primate, wherein the bacterium is configured to express one or more exogenous nucleic acid sequences encoding an antigen heterologous to the bacterium. Such a bacterium is referred to herein as a "vaccine."

The vaccine compositions described herein can be administered to a primate host, either alone or in combination with a pharmaceutically acceptable excipient, in an amount sufficient to induce an appropriate immune response, e.g., to prevent or treat a malignancy, a pathogenic infection, or other clinical condition. Preferred conditions are selected to induce a T cell response in a subject to the heterologous antigens expressed by the cellular vaccine. Such conditions may comprise administering the vaccine platform intravenously to a subject; however, administration may be oral, intravenous, subcutaneous, dermal, intradermal, intramuscular, mucosal, parenteral, intraorgan, intralesional, intranasal, inhalation, intraocular, intravascular, intranodal, by scarification, rectal, intraperitoneal, or any one or combination of a variety of well-known routes of administration.

In certain preferred embodiments, after the subject has been administered an effective dose of a cellular vaccine containing the immunogenic polypeptides to prime the immune response, a second vaccine is administered. This is referred to in the art as a "prime-boost" regimen. In such a regimen, the compositions and methods of the present invention may be used as the "prime" delivery, as the "boost" delivery, or as both a "prime" and a "boost." Examples of such regimens are described hereinafter.

In certain embodiments, the heterologous polypeptide(s) may be expressed as a fusion protein comprising an in frame secretory signal sequence, thereby resulting in their secretion as soluble polypeptide(s) by the cells. Numerous exemplary signal sequences are known in the art for use in various expression systems, including bacterial expression systems. In the case where the bacterium is *Listeria monocytogenes*, it is preferred that the secretory signal sequence is a *Listeria monocytogenes* signal sequence, most preferably the ActA signal sequence. Additional ActA or other linker amino acids may also be expressed fused to the immunogenic polypeptide(s). In certain embodiments, the N-terminal signal peptide/secretion chaperone fusion partner is derived from ActA or LLO. Other signal sequences that may find use in the present invention are described in U.S. Pat. No. 7,842,289, and include major merozoite surface antigen (MSP-1) from *Plasmodium*, Usp45 signal peptide from *Lactococcus lactis*, Protective Antigen signal peptide from *Bacillus anthracis*, secA2 signal peptide from *Listeria monocytogenes* and Tat signal peptide from *B. subtilis*. This list is not meant to be limiting.

In certain embodiments, the N-terminal signal peptide/secretion chaperone fusion partner is optionally truncated relative to the native length of the parent protein (e.g., ActA or LLO). By way of example, ActA may be truncated to delete the C-terminal membrane-binding domain, and in certain embodiments even further, to decrease the number of non-antigenic residues in the fusion protein. Similarly, LLO may be truncated prior to about residue 484 in order to abrogate cholesterol binding, and in certain embodiments even further, to again decrease the number of non-antigenic residues in the fusion protein. In preferred embodiments, one or more immunogenic polypeptide(s) are expressed as fusion protein(s) comprising an in frame ActA-N100 sequence (e.g., selected from the group consisting of SEQ ID NO: 37, 38 and 39) or an amino acid sequence having at least 90% sequence identity to said ActA-N100 sequence. Such a fusion protein is preferably expressed from a nucleic acid sequence operably linked to a *Listeria monocytogenes* ActA promoter. Such signal sequences may also be modified as described in WO 2014106123, which is hereby incorporated by reference.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

Figure 1:
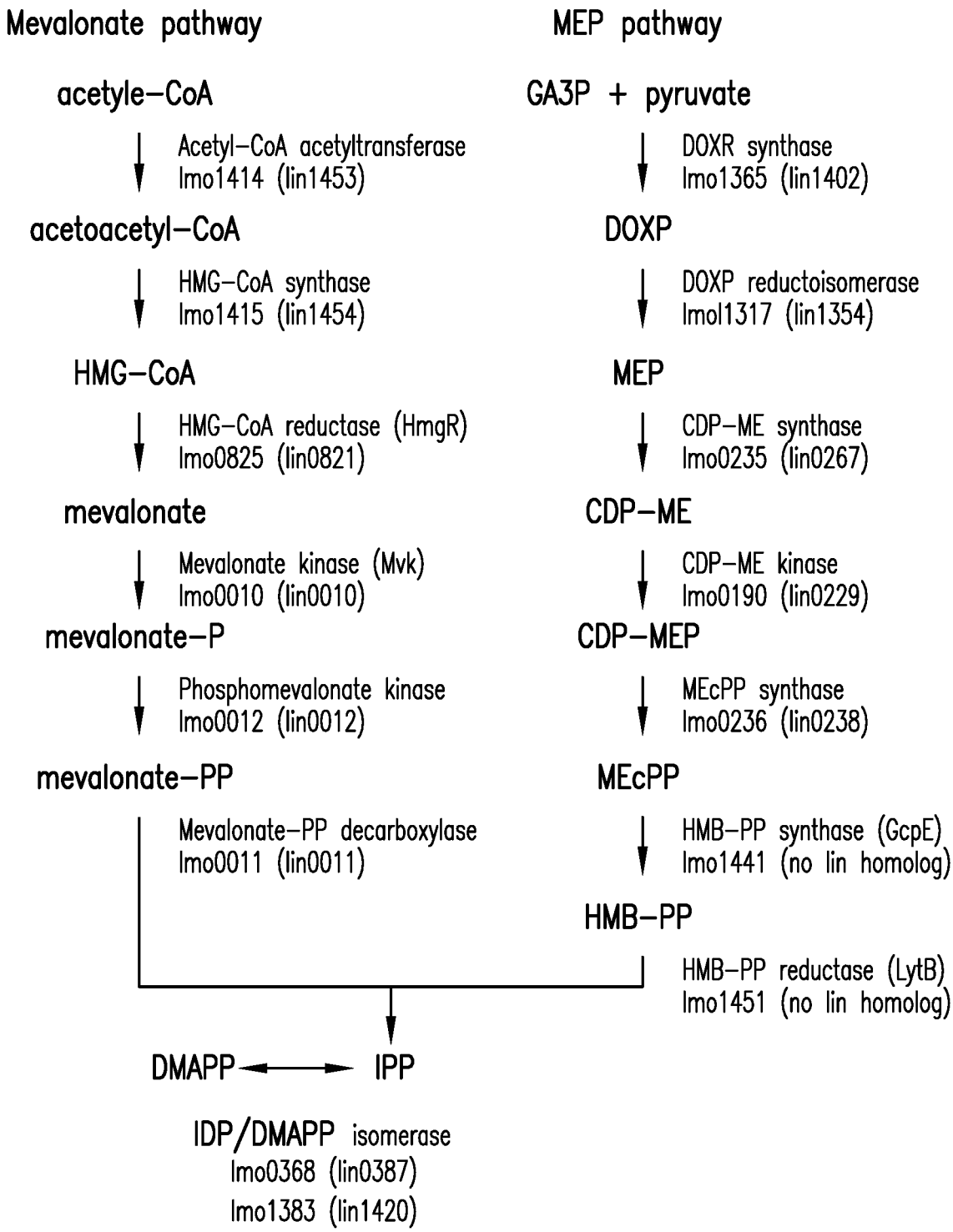
FIG. 1. A schematic representation of the mevalonate and MEP pathways in *Listeria*.
Figure 2:
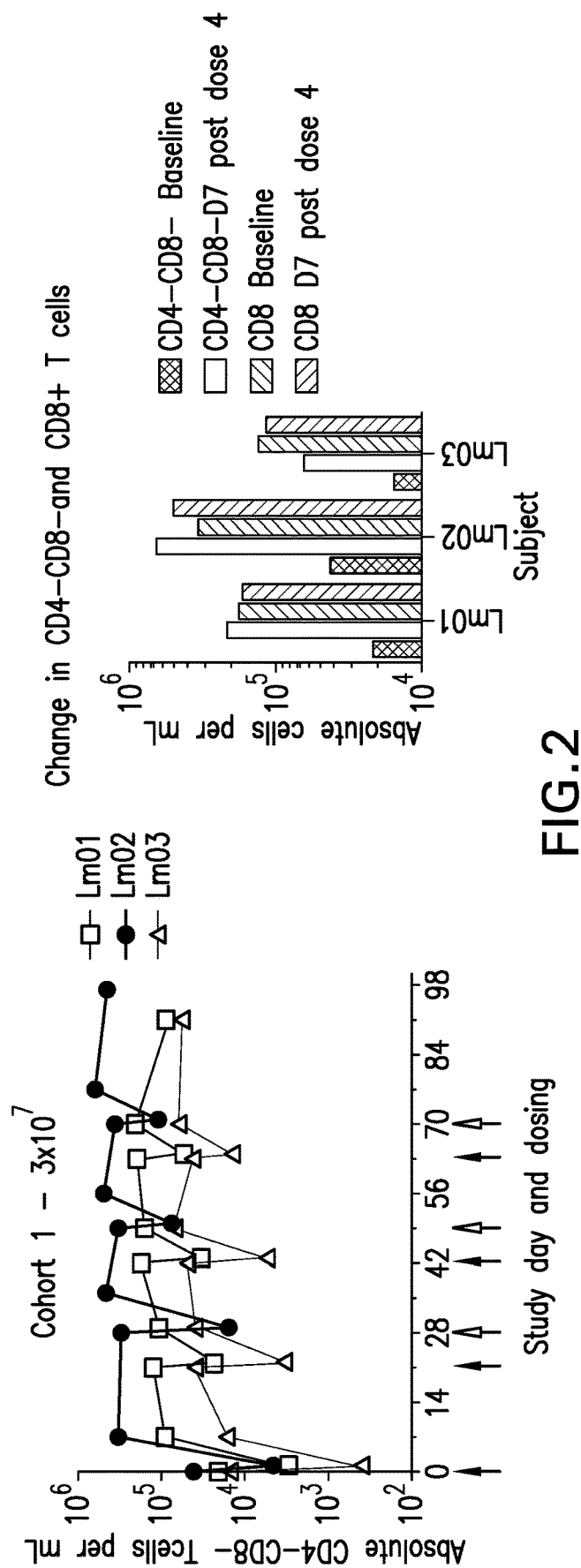
FIG. 2 depicts changes in CD4-CD8- and CD8+ T-cells in individuals administered live-attenuated ΔactA/ΔinlB *Listeria monocytogenes* expressing EGFRvIII and NY-ESO-1 (ADU-623).
Figure 3:
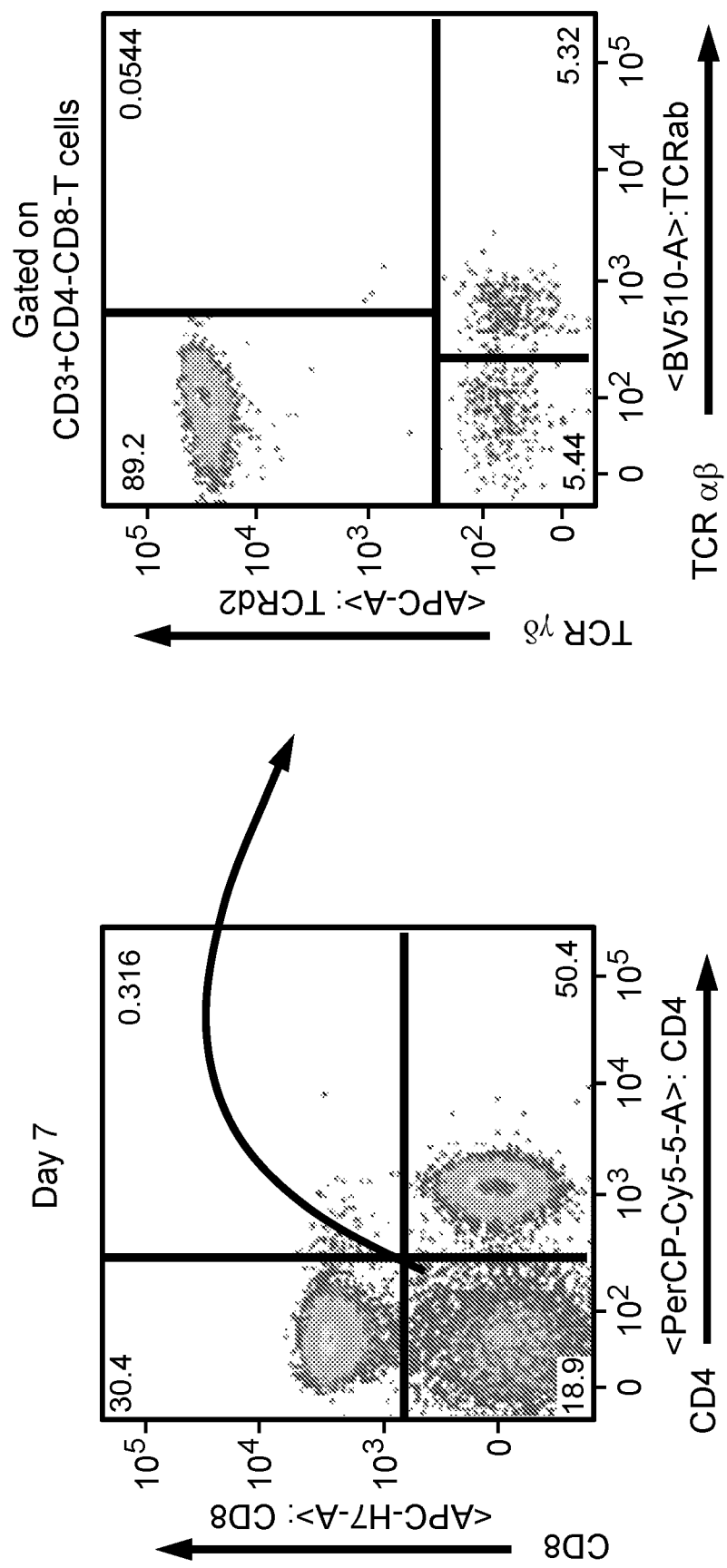
FIG. 3 depicts T-cell subpopulations observed at day 7 following initial administration of ADU-623.
Figure 4:
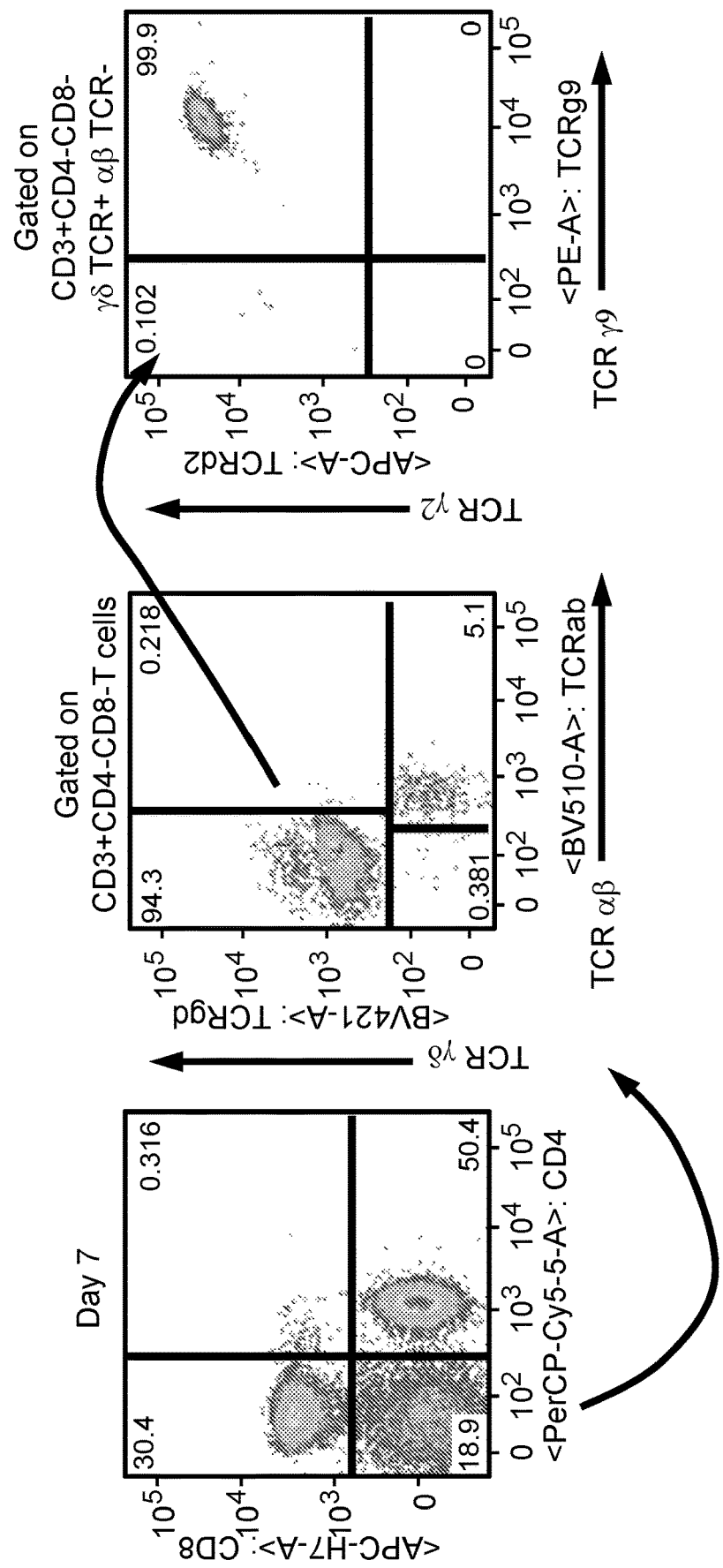
FIG. 4 depicts T-cell subpopulations observed at day 7 following initial administration of ADU-623.
Figure 5:
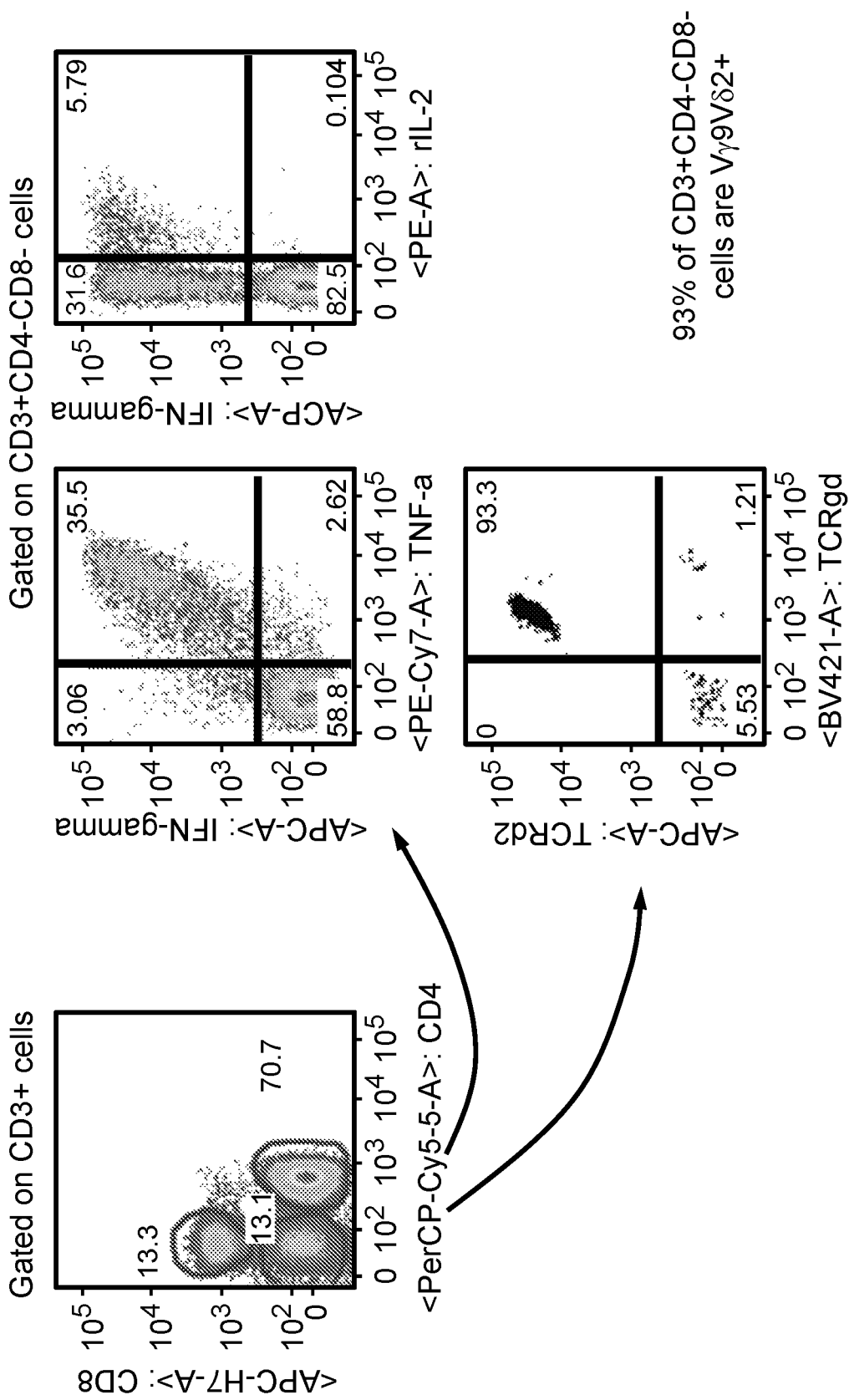
FIG. 5 depicts in vitro restimulation of T-cell subpopulations observed at day 7 following initial administration of ADU-623 using HMB-PP.
Figure 6:
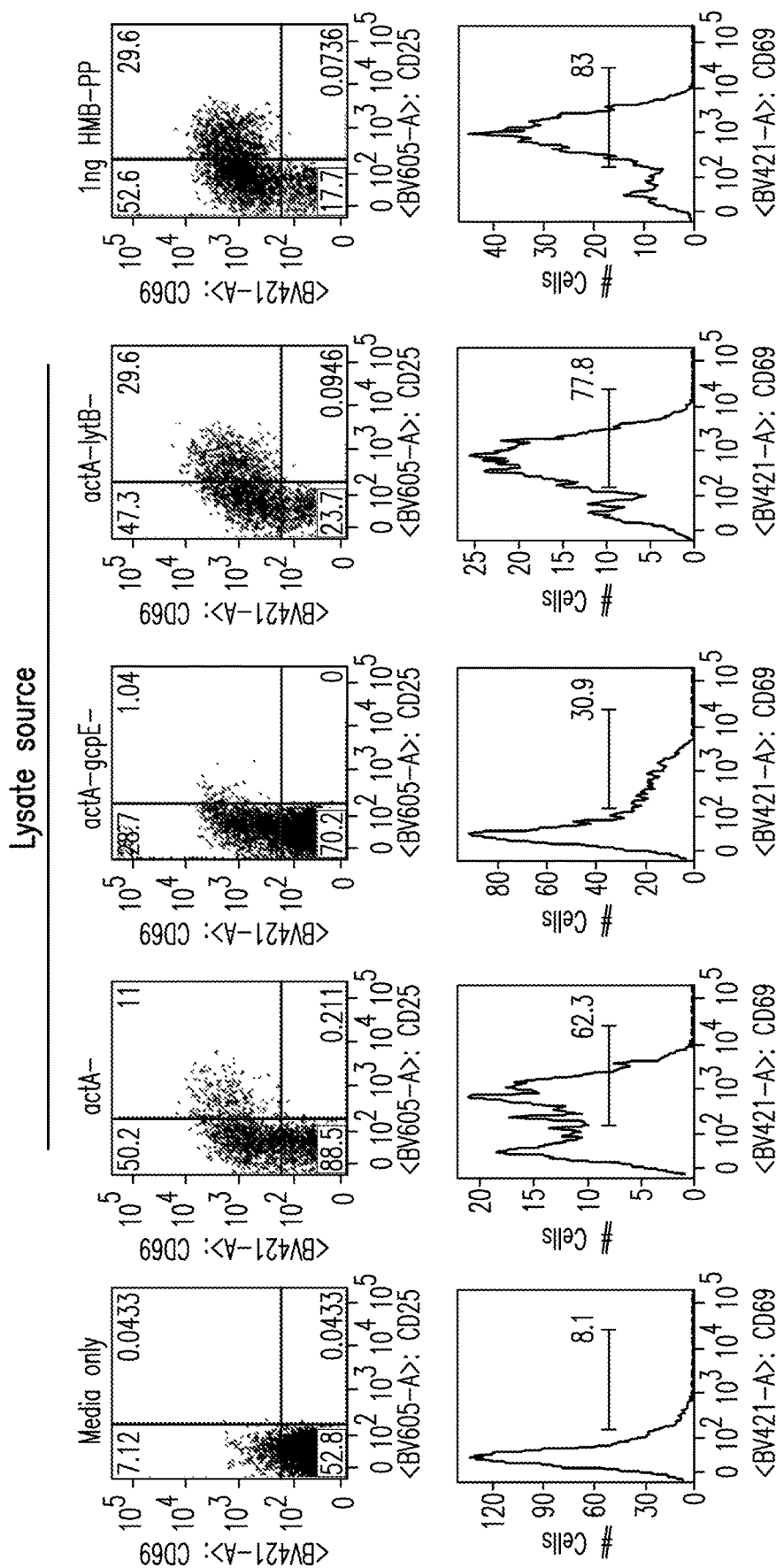
FIG. 6 depicts the stimulation of human gamma delta T cells using various *Listeria* strain lysates with HMB-PP restimulation as a positive control.

The present invention relates to the preparation and use in primates of bacterial vaccines in which the MEP pathway is disrupted such that synthesis of HMBPP by the bacterial cells is substantially blocked. The present invention can provide bacterial vaccine strains with advantageous therapeutic profiles for use treatment or prevention of diseases. While described hereinafter in detail with regard to *Listeria monocytogenes*, the skilled artisan will understand that the methods and compositions described herein are generally applicable to bacterial species, and in particular to facultative intracellular bacterial species.

*Listeria monocytogenes* (Lm) is a facultative intracellular bacterium characterized by its ability to induce a profound innate immune response through activation of multiple sensors, including TLRs, NODs and STING, leading to a robust and highly functional CD4 and CD8 T cell immunity specific for vaccine-encoded Ags. Lm is a food-borne bacterium with increased pathogenicity among immune compromised individuals, including patients with cancer or other viral-induced immune deficiencies, pregnant women, the elderly and infants. Live-attenuated recombinant Lm vaccine platforms engineered to encode a designated antigen(s) relevant to a selected targeted pathogenic agent or malignancy have formed the basis for several human clinical trials.

T cells are subdivided into two major populations distinguished by their surface expression of αβ and γδ T cell receptors (TCR). Both αβ and γδ T cells arise from common multipotent double negative (DN) precursors in the thymus, which can be further separated into four DN subsets based on CD44 and CD25 expression. The T cells undergo extensive DNA rearrangements at the β, γ and δ TCR loci aiming to express functional TCR chains and make a selection between two developmental programs during the DN3 stage, thus generating two distinct characteristics and functions of T cell subsets. Cells with the αβ TCR generally express CD4 or CD8 lineage markers and mostly fall into helper or cytotoxiceffector and memory subsets. Genetically defined live-attenuated Lm ΔactAΔinlB, which is deleted of two virulence genes and is attenuated >3 logs in the mouse listeriosis model, retains its immunologic potency and has been shown to induce robust CD4 and CD8 T cell immunity in both mouse models of human disease as well as in humans, and has been shown to be safe and well-tolerated in clinical settings among patients with various solid tumor malignancies.

There are several other approaches to attenuate wild-type *Listeria monocytogenes* that may also be adopted for use in humans to prevent or treat infections and diverse malignancies. Non-limiting examples of said approaches include, for example, deletion or mutation of ActA (Lm ΔactA), or deletion of the Lm master transcription regulator PrfA (Lm ΔprfA) required for activation of expression of virulence genes required for intracellular growth, and complementing the deletion by expression of PrfA from an extra-bacterial chromosomal plasmid element. Heterologous antigen expression cassettes can also be incorporated into this plasmid element, in addition to the PrfA-encoding sequences. It will be apparent to those skilled in the art that the various methods of attenuations provided here as non-limiting examples can be combined.

In contrast to the CD4 and CD8 T cell lineages seen in these clinical trials, γδ T cells, and in particular Vγ9/Vδ2 T cells, are unique to humans and primates and represent a normal constituent of the leukocyte population in peripheral blood (0.5-5%). This T cell population expands dramatically in many acute infections and may exceed all other lymphocytes within a few days, e.g. in tuberculosis, *salmonellosis*, ehrlichiosis, brucellosis, tularemia, listeriosis, toxoplasmosis, and malaria. Vγ9/Vδ2 T cells recognize the small microbial compound (E)-4-hydroxy-3-methyl-but-2-enyl pyrophosphate (HMB-PP), a natural intermediate of the non-mevalonate pathway of isopentenyl pyrophosphate (IPP) biosynthesis.[11] HMB-PP is an essential metabolite in most pathogenic bacteria including *Mycobacterium tuberculosis* and malaria parasites, but is absent from the human host. Bacterial species that lack the non-mevalonate pathway and synthesize IPP via the classical mevalonate pathway instead, such as *Streptococcus, Staphylococcus*, and *Borrelia*, are unable to produce HMB-PP and do not specifically activate Vγ9/Vδ2 T cells.

As demonstrated below, γδ T cells unexpectedly dominate the T cell response observed in certain clinical trials of Listerial vaccines. γδ T cells exhibit varying degrees of cytolytic activity to various kinds of malignancies, and exhibit broad cytotoxic activity against a wide variety of tumor cells, in which they utilize death receptor/ligand (e.g. Fas/Fas-ligand)-dependent and perforin/granzyme- or granulysin-dependent pathways. For this reason, γδ T cells have been proposed as a useful tool for cancer immunotherapy. However, in the context of bacterial vaccine platforms, this γδ T cell response has a negative effect by causing the vaccine platform to be cleared from the host, thereby limiting its effectiveness as a vaccine.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

1. Definitions

Abbreviations used to indicate a mutation in a gene, or a mutation in a bacterium comprising the gene, are as follows. By way of example, the abbreviation "*L. monocytogenes* ΔactA" means that part, or all, of the actA gene was deleted. The delta symbol (Δ) means deletion. An abbreviation including a superscripted minus sign (*Listeria* ActA$^-$) means that the actA gene was mutated, e.g., by way of a deletion, point mutation, or frameshift mutation, but not limited to these types of mutations.

"Administration" as it applies to a human, primate, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) can encompass GM-CSF, a mutein or derivative of GM-CSF, a peptide mimetic of GM-CSF, a small molecule that mimics the biological function of GM-CSF, or an antibody that stimulates GM-CSF receptor.

An "antagonist," as it relates to a ligand and receptor, comprises a molecule, combination of molecules, or a complex, that inhibits, counteracts, downregulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

As used herein, an "analog" or "derivative" with reference to a peptide, polypeptide or protein refers to another peptide, polypeptide or protein that possesses a similar or identical function as the original peptide, polypeptide or protein, but does not necessarily comprise a similar or identical amino acid sequence or structure of the original peptide, polypeptide or protein. An analog preferably satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the original amino acid sequence (b) a proteinaceous agent encoded by a nucleotide sequence that hybridizes under stringent conditions to a nucleotide sequence encoding the original amino acid sequence; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding the original amino acid sequence.

"Antigen presenting cells" (APCs) are cells of the immune system used for presenting antigen to T cells. APCs include dendritic cells, monocytes, macrophages, marginal zone Kupffer cells, microglia, Langerhans cells, T cells, and B cells. Dendritic cells occur in at least two lineages. The first lineage encompasses pre-DC1, myeloid DC1, and mature DC1. The second lineage encompasses CD34$^+$ CD45RA$^-$ early progenitor multipotent cells, CD34$^+$ CD45RA$^+$ cells, CD34$^+$CD45RA$^+$CD4$^+$ IL-3Rα$^+$ pro-DC2 cells, CD4$^+$CD11c$^-$ plasmacytoid pre-DC2 cells, lymphoid human DC2 plasmacytoid-derived DC2s, and mature DC2s.

"Attenuation" and "attenuated" encompasses a bacterium, virus, parasite, infectious organism, prion, tumor cell, gene in the infectious organism, and the like, that is modified to reduce toxicity to a host. The host can be a human or animal host, or an organ, tissue, or cell. The bacterium, to give a non-limiting example, can be attenuated to reduce binding to a host cell, to reduce spread from one host cell to another host cell, to reduce extracellular growth, or to reduce intracellular growth in a host cell. Attenuation can be assessed by measuring, e.g., an indicum or indicia of toxicity, the LD$_{50}$, the rate of clearance from an organ, or the competitive index (see, e.g., Auerbuch, et al. (2001) Infect. Immunity 69:5953-5957). Generally, an attenuation results an increase in the LD$_{50}$ and/or an increase in the rate of clearance by at least 25%; more generally by at least 50%; most generally by at least 100% (2-fold); normally by at least 5-fold; more normally by at least 10-fold; most normally by at least 50-fold; often by at least 100-fold; more often by at least 500-fold; and most often by at least 1000-fold; usually by at least 5000-fold; more usually by at least 10,000-fold; and most usually by at least 50,000-fold; and most often by at least 100,000-fold.

"Attenuated gene" encompasses a gene that mediates toxicity, pathology, or virulence, to a host, growth within the host, or survival within the host, where the gene is mutated in a way that mitigates, reduces, or eliminates the toxicity, pathology, or virulence. The reduction or elimination can be assessed by comparing the virulence or toxicity mediated by the mutated gene with that mediated by the non-mutated (or parent) gene. "Mutated gene" encompasses deletions, point mutations, and frameshift mutations in regulatory regions of the gene, coding regions of the gene, non-coding regions of the gene, or any combination thereof.

"Conservatively modified variants" applies to both amino acid and nucleic acid sequences. With respect to particular nucleic acid sequences, a conservatively modified variant refers to nucleic acids encoding identical amino acid sequences, or amino acid sequences that have one or more conservative substitutions. An example of a conservative substitution is the exchange of an amino acid in one of the following groups for another amino acid of the same group (U.S. Pat. No. 5,767,063 issued to Lee, et al.; Kyte and Doolittle (1982) J. Mol. Biol. 157:105-132).
(1) Hydrophobic: Norleucine, Ile, Val, Leu, Phe, Cys, Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro;
(6) Aromatic: Trp, Tyr, Phe; and
(7) Small amino acids: Gly, Ala, Ser.

"Effective amount" encompasses, without limitation, an amount that can ameliorate, reverse, mitigate, prevent, or diagnose a symptom or sign of a medical condition or disorder. Unless dictated otherwise, explicitly or by context, an "effective amount" is not limited to a minimal amount sufficient to ameliorate a condition.

An "extracellular fluid" encompasses, e.g., serum, plasma, blood, interstitial fluid, cerebrospinal fluid, secreted fluids, lymph, bile, sweat, fecal matter, and urine. An "extracelluar fluid" can comprise a colloid or a suspension, e.g., whole blood or coagulated blood.

The term "fragments" in the context of polypeptides include a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a larger polypeptide.

"Gene" refers to a nucleic acid sequence encoding an oligopeptide or polypeptide. The oligopeptide or polypeptide can be biologically active, antigenically active, biologically inactive, or antigenically inactive, and the like. The term gene encompasses, e.g., the sum of the open reading frames (ORFs) encoding a specific oligopeptide or polypeptide; the sum of the ORFs plus the nucleic acids encoding introns; the sum of the ORFs and the operably linked promoter(s); the sum of the ORFS and the operably linked promoter(s) and any introns; the sum of the ORFS and the operably linked promoter(s), intron(s), and promoter(s), and other regulatory elements, such as enhancer(s). In certain embodiments, "gene" encompasses any sequences required in cis for regulating expression of the gene. The term gene can also refer to a nucleic acid that encodes a peptide encompassing an antigen or an antigenically active fragment of a peptide, oligopeptide, polypeptide, or protein. The term gene does not necessarily imply that the encoded peptide or protein has any biological activity, or even that the peptide or protein is antigenically active. A nucleic acid sequence encoding a non-expressable sequence is generally considered a pseudogene. The term gene also encompasses nucleic acid sequences encoding a ribonucleic acid such as rRNA, tRNA, or a ribozyme.

"Growth" of a bacterium such as *Listeria* encompasses, without limitation, functions of bacterial physiology and genes relating to colonization, replication, increase in protein content, and/or increase in lipid content. Unless specified otherwise explicitly or by context, growth of a *Listeria* encompasses growth of the bacterium outside a host cell, and also growth inside a host cell, and, possibly, intracellular spread to neighboring cells. Growth related genes include, without implying any limitation, those that mediate energy production (e.g., glycolysis, Krebs cycle, cytochromes), anabolism and/or catabolism of amino acids, sugars, lipids, minerals, purines, and pyrimidines, nutrient transport, transcription, translation, and/or replication. In some embodiments, "growth" of a *Listeria* bacterium refers to intracellular growth of the *Listeria* bacterium, that is, growth inside a host cell such as a mammalian cell. While intracellular growth of a *Listeria* bacterium can be measured by light microscopy or colony forming unit (CFU) assays, growth is not to be limited by any technique of measurement. Biochemical parameters such as the quantity of a Listerial antigen, Listerial nucleic acid sequence, or lipid specific to the *Listeria* bacterium, can be used to assess growth. In some embodiments, a gene that mediates growth is one that specifically mediates intracellular growth. In some embodiments, a gene that specifically mediates intracellular growth encompasses, but is not limited to, a gene where inactivation of the gene reduces the rate of intracellular growth but does not detectably, substantially, or appreciably, reduce the rate of extracellular growth (e.g., growth in broth), or a gene where inactivation of the gene reduces the rate of intracellular growth to a greater extent than it reduces the rate of extracellular growth. To provide a non-limiting example, in some embodiments, a gene where inactivation reduces the rate of intracellular growth to a greater extent than extracellular growth encompasses the situation where inactivation reduces intracellular growth to less than 50% the normal or maximal value, but reduces extracellular growth to only 1-5%, 5-10%, or 10-15% the maximal value. The invention, in certain aspects, encompasses a *Listeria* attenuated in intracellular growth but not attenuated in extracellular growth, a *Listeria* not attenuated in intracellular growth and not attenuated in extracellular growth, as well as a *Listeria* not attenuated in intracellular growth but attenuated in extracellular growth.

A composition that is "labeled" is detectable, either directly or indirectly, by spectroscopic, photochemical, biochemical, immunochemical, isotopic, or chemical methods. For example, useful labels include $^{32}P$, $^{33}P$, $^{35}S$, $^{14}C$, $^{3}H$, $^{125}I$ stable isotopes, epitope tags, fluorescent dyes, electron-dense reagents, substrates, or enzymes, e.g., as used in enzyme-linked immunoassays, or fluorettes (see, e.g., Rozinov and Nolan (1998) Chem. Biol. 5:713-728).

"Ligand" refers to a small molecule, peptide, polypeptide, or membrane associated or membrane-bound molecule, that is an agonist or antagonist of a receptor. "Ligand" also encompasses a binding agent that is not an agonist or antagonist, and has no agonist or antagonist properties. By convention, where a ligand is membrane-bound on a first cell, the receptor usually occurs on a second cell. The second cell may have the same identity (the same name), or it may have a different identity (a different name), as the first cell. A ligand or receptor may be entirely intracellular, that is, it may reside in the cytosol, nucleus, or in some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

"Nucleic acid" refers to deoxyribonucleotides or ribonucleotides and polymers thereof in either single stranded, double-stranded form, or multi-stranded form. Non-limiting examples of a nucleic acid are a, e.g., cDNA, mRNA, oligonucleotide, and polynucleotide. A particular nucleic acid sequence can also implicitly encompasses "allelic variants" and "splice variants."

"Operably linked" in the context of a promoter and a nucleic acid encoding a mRNA means that the promoter can be used to initiate transcription of that nucleic acid.

The terms "percent sequence identity" and "% sequence identity" refer to the percentage of sequence similarity found by a comparison or alignment of two or more amino acid or nucleic acid sequences. Percent identity can be determined by a direct comparison of the sequence information between two molecules by aligning the sequences, counting the exact number of matches between the two aligned sequences, dividing by the length of the shorter sequence, and multiplying the result by 100. An algorithm for calculating percent identity is the Smith-Waterman homology search algorithm (see, e.g., Kann and Goldstein (2002) Proteins 48:367-376; Arslan, et al. (2001) Bioinformatics 17:327-337).

By "purified" and "isolated" is meant, when referring to a polypeptide, that the polypeptide is present in the substantial absence of the other biological macromolecules with which it is associated in nature. The term "purified" as used herein means that an identified polypeptide often accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the polypeptides present. The weights of water, buffers, salts, detergents, reductants, protease inhibitors, stabilizers (including an added protein such as albumin), and excipients, and molecules having a molecular weight of less than 1000, are generally not used in the determination of polypeptide purity. See, e.g., discussion of purity in U.S. Pat. No. 6,090,611 issued to Covacci, et al.

"Peptide" refers to a short sequence of amino acids, where the amino acids are connected to each other by peptide bonds. A peptide may occur free or bound to another moiety, such as a macromolecule, lipid, oligo- or polysaccharide, and/or a polypeptide. Where a peptide is incorporated into a polypeptide chain, the term "peptide" may still be used to refer specifically to the short sequence of amino acids. A "peptide" may be connected to another moiety by way of a peptide bond or some other type of linkage. A peptide is at least two amino acids in length and generally less than about 25 amino acids in length, where the maximal length is a function of custom or context. The terms "peptide" and "oligopeptide" may be used interchangeably.

"Protein" generally refers to the sequence of amino acids comprising a polypeptide chain. Protein may also refer to a three dimensional structure of the polypeptide. "Denatured protein" refers to a partially denatured polypeptide, having some residual three dimensional structure or, alternatively, to an essentially random three dimensional structure, i.e., totally denatured. The invention encompasses reagents of, and methods using, polypeptide variants, e.g., involving glycosylation, phosphorylation, sulfation, disulfide bond formation, deamidation, isomerization, cleavage points in signal or leader sequence processing, covalent and non-covalently bound cofactors, oxidized variants, and the like. The formation of disulfide linked proteins is described (see, e.g., Woycechowsky and Raines (2000) Curr. Opin. Chem. Biol. 4:533-539; Creighton, et al. (1995) Trends Biotechnol. 13:18-23).

"Recombinant" when used with reference, e.g., to a nucleic acid, cell, animal, virus, plasmid, vector, or the like, indicates modification by the introduction of an exogenous, non-native nucleic acid, alteration of a native nucleic acid, or by derivation in whole or in part from a recombinant nucleic acid, cell, virus, plasmid, or vector. Recombinant protein refers to a protein derived, e.g., from a recombinant nucleic acid, virus, plasmid, vector, or the like. "Recombinant bacterium" encompasses a bacterium where the genome is engineered by recombinant methods, e.g., by way of a mutation, deletion, insertion, and/or a rearrangement. "Recombinant bacterium" also encompasses a bacterium modified to include a recombinant extra-genomic nucleic acid, e.g., a plasmid or a second chromosome, or a bacterium where an existing extra-genomic nucleic acid is altered.

"Sample" refers to a sample from a human, animal, placebo, or research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

A "selectable marker" encompasses a nucleic acid that allows one to select for or against a cell that contains the selectable marker. Examples of selectable markers include, without limitation, e.g.: (1) A nucleic acid encoding a product providing resistance to an otherwise toxic compound (e.g., an antibiotic), or encoding susceptibility to an otherwise harmless compound (e.g., sucrose); (2) A nucleic acid encoding a product that is otherwise lacking in the recipient cell (e.g., tRNA genes, auxotrophic markers); (3) A nucleic acid encoding a product that suppresses an activity of a gene product; (4) A nucleic acid that encodes a product that can be readily identified (e.g., phenotypic markers such as beta-galactosidase, green fluorescent protein (GFP), cell surface proteins, an epitope tag, a FLAG tag); (5) A nucleic acid that can be identified by hybridization techniques, for example, PCR or molecular beacons.

"Specifically" or "selectively" binds, when referring to a ligand/receptor, nucleic acid/complementary nucleic acid, antibody/antigen, or other binding pair (e.g., a cytokine to a cytokine receptor) indicates a binding reaction which is determinative of the presence of the protein in a heterogeneous population of proteins and other biologics. Thus, under designated conditions, a specified ligand binds to a particular receptor and does not bind in a significant amount to other proteins present in the sample. Specific binding can also mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with any other binding compound.

In a typical embodiment an antibody will have an affinity that is greater than about $10^9$ liters/mol, as determined, e.g., by Scatchard analysis (Munsen, et al. (1980) Analyt. Biochem. 107:220-239). It is recognized by the skilled artisan that some binding compounds can specifically bind to more than one target, e.g., an antibody specifically binds to its antigen, to lectins by way of the antibody's oligosaccharide, and/or to an Fc receptor by way of the antibody's Fc region.

"Spread" of a bacterium encompasses "cell to cell spread," that is, transmission of the bacterium from a first host cell to a second host cell, as mediated, for example, by a vesicle. Functions relating to spread include, but are not limited to, e.g., formation of an actin tail, formation of a pseudopod-like extension, and formation of a double-membraned vacuole.

The term "subject" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology.

The "target site" of a recombinase is the nucleic acid sequence or region that is recognized, bound, and/or acted upon by the recombinase (see, e.g., U.S. Pat. No. 6,379,943 issued to Graham, et al.; Smith and Thorpe (2002) Mol. Microbiol. 44:299-307; Groth and Calos (2004) J. Mol. Biol. 335:667-678; Nunes-Duby, et al. (1998) Nucleic Acids Res. 26:391-406).

"Therapeutically effective amount" is defined as an amount of a reagent or pharmaceutical composition that is sufficient to induce a desired immune response specific for encoded heterologous antigens, show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual (see, e.g., U.S. Pat. No. 5,888,530 issued to Netti, et al.).

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, and/or prolonging survival.

"Vaccine" encompasses preventative vaccines. Vaccine also encompasses therapeutic vaccines, e.g., a vaccine administered to a mammal that comprises a condition or disorder associated with the antigen or epitope provided by the vaccine. A number of bacterial species have been developed for use as vaccines and can be used in the present invention, including, but not limited to, *Shigella flexneri, Escherichia coli, Listeria monocytogenes, Yersinia enterocolitica, Salmonella typhimurium, Salmonella typhi* or *mycobacterium* species. This list is not meant to be limiting. See, e.g., WO04/006837; WO07/103225; and WO07/117371, each of which is hereby incorporated by reference in its entirety, including all tables, figures, and claims. The bacterial vector used in the vaccine composition may be a facultative, intracellular bacterial vector. The bacterium may be used to deliver a polypeptide described herein to antigen-presenting cells in the host organism. As described herein, *L. monocytogenes* provides a preferred vaccine platform for expression of the antigens of the present invention.

2. Functional Deletion of Genes of the MEP Pathway

Preferred genes to target for functional deletion include those that encode a protein selected from the group consisting of DOXP synthase, DOXP reductoisomerase, CDP-ME synthase, CDP-ME kinase, MEcPP synthase, and HMB-PP synthase. A description of the MEP pathway, containing a listing of the corresponding *Listeria* genes, including entry number in the Pasteur *L. monocytogenes* and *L. innocua* ListiList database, is provided in FIG. 1.

The term "functional deletion" as used herein with respect to a particular enzymatic activity refers to a level of enzymatic activity that is 10% or less of that measured in a comparable wild type bacterial cell of the same species. The mutations described herein for functional deletion of one or more genes in the MEP pathway may be any mutation, such as one or more nucleic acid deletions, insertions or substitutions. The mutations may be any deletion, insertion or substitution of the loci or genes that results in a reduction or absence of expression from the loci or genes, or a reduction or absence of activity of a polypeptide encoded by the loci or genes. The mutations may be in the coding or non-coding regions of the loci or genes. Such reduced enzymatic activities can be the result of lower enzyme concentration, lower specific activity of an enzyme, or a combination thereof.

Many different methods can be used to make bacteria having reduced enzymatic activity. For example, several methods for disrupting gene functions are well-known in the art and may be used in the practice of the invention. Such methods include, but are not limited to, gene replacement by homologous recombination, antisense technologies, and RNA interference. To delete or inactivate a target gene, for example, a method involving homologous recombination may be used. That is, a cyclic recombinant plasmid obtained by cloning a DNA fragment containing a part of the target gene in an appropriate plasmid can be transfected into the cells of a parent microorganism, so that the target gene on the genome of the parent microorganism is split by homologous recombination in some region of the target gene, thereby inactivating the target gene. Alternatively, it is also possible to substitute a target gene on the genome with a deleted or inactivated gene fragment, by constructing a target gene inactivated through mutation such as base substitution or base insertion, or a linear DNA fragment containing the upstream and downstream regions of the target gene but not containing the target gene, and introducing the resultant sequences into the cells of a parent microorganism, to thereby cause double crossover homologous recombination at two sites exterior to the mutation site within the target gene on the genome of the parent microorganism, or on the upstream side and downstream side of the target gene.

Alternatively, one or more enzymes within the MEP pathway may be targeted chemically in order to functionally delete the enzymatic activity of interest. By way of example, fosmidomycin is an antibiotic that specifically inhibits DOXP reductoisomerase.

3. Heterologous Antigen Expression

The ability of L. monocytogenes to serve as a vaccine vector has been reviewed in Wesikirch, et al., Immunol. Rev. 158:159-169 (1997). A number of desirable features of the natural biology of L. monocytogenes make it an attractive platform for application to a therapeutic vaccine. The central rationale is that the intracellular lifecycle of L. monocytogenes enables effective stimulation of CD4+ and CD8+ T cell immunity. Multiple pathogen associated molecular pattern (PAMP) receptors including TLRs (TLR2, TLR5, TLR9) nucleotide-binding oligomerization domains (NOD), and Stimulator of Interferon Genes (STING) are triggered in response to interaction with L. monocytogenes macromolecules upon infection, resulting in the pan-activation of innate immune effectors and release of Th-1 polarizing cytokines, exerting a profound impact on the development of a CD4+ and CD8+ T cell response against the expressed antigens.

Strains of L. monocytogenes have recently been developed as effective intracellular delivery vehicles of heterologous proteins providing delivery of antigens to the immune system to induce an immune response to clinical conditions that do not permit injection of the disease-causing agent, such as cancer and HIV. See, e.g., U.S. Pat. No. 6,051,237; Gunn et al., J. Immunol., 167:6471-6479 (2001); Liau, et al., Cancer Research, 62: 2287-2293 (2002); Le, et. al., Clinical Cancer Research 18: 1-11 (2011); U.S. Pat. No. 6,099,848; WO 99/25376; WO 96/14087; and U.S. Pat. No. 5,830,702), each of which is hereby incorporated by reference in its entirety, including all tables, figures, and claims. A recombinant L. monocytogenes vaccine expressing an lymphocytic choriomeningitis virus (LCMV) antigen has also been shown to induce protective cell-mediated immunity to the antigen (Shen et al., Proc. Natl. Acad. Sci. USA, 92: 3987-3991 (1995).

In certain embodiments, the L. monocytogenes used in the vaccine compositions of the present invention is RIID strain which further comprises an attenuating mutation in actA and/or inlB, and preferably a deletion of all or a portion of actA and inlB (referred to herein as "Lm ΔactA/ΔinlB"), and contains recombinant DNA encoding for the expression of the one or more antigen(s) of interest. The antigen(s) are preferably under the control of bacterial expression sequences and are stably integrated into the L. monocytogenes genome.

The invention also contemplates a Listeria attenuated in at least one regulatory factor, e.g., a promoter or a transcription factor. The following concerns promoters. ActA expression is regulated by two different promoters (Vazwuez-Boland, et al. (1992) Infect. Immun. 60:219-230). Together, InlA and InlB expression is regulated by five promoters (Lingnau, et al. (1995) Infect. Immun. 63:3896-3903). The transcription factor prfA is required for transcription of a number of L. monocytogenes genes, e.g., hly, plcA, ActA, mpl, prfA, and iap. PrfA's regulatory properties are mediated by, e.g., the PrfA-dependent promoter (PinlC) and the PrfA-box. The present invention, in certain embodiments, provides a nucleic acid encoding inactivated, mutated, or deleted in at least one of ActA promoter, inlB promoter, PrfA, PinlC, PrfA box, and the like (see, e.g., Lalic Mullthaler, et al. (2001) Mol. Microbiol. 42:111-120; Shetron-Rama, et al. (2003) Mol. Microbiol. 48:1537-1551; Luo, et al. (2004) Mol. Microbiol. 52:39-52). PrfA can be made constitutively active by a Gly145Ser mutation, Gly155Ser mutation, or Glu77Lys mutation (see, e.g., Mueller and Freitag (2005) Infect. Immun. 73:1917-1926; Wong and Freitag (2004) J. Bacteriol. 186:6265-6276; Ripio, et al. (1997) J. Bacteriol. 179:1533-1540).

Examples of target antigens that may find use in the invention are listed in the following table. The target antigen may also be a fragment or fusion polypeptide comprising an immunologically active portion of the antigens listed in the table. This list is not meant to be limiting.

TABLE 1

| Antigens | |
|---|---|
| Antigen | Reference |
| Tumor antigens | |
| Mesothelin | GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |
| Wilms' tumor-1 associated protein (Wt-1), including isoform A; isoform B; isoform C; isoform D. | WT-1 isoform A (GenBank Acc. Nos. NM_000378; NP_000369). WT-1 isoform B (GenBank Acc. Nos. NM_024424; NP_077742). WT-1 isoform C (GenBank Acc. Nos. NM_024425; NP_077743). WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein A (MICB). | See, e.g., Groh, et al. (2005) Proc. Natl. Acad. Sci. USA 102: 6461-6466; GenBank Acc. Nos. NM_000247; BC_016929; AY750850; NM_005931. |

TABLE 1-continued

Antigens

| Antigen | Reference |
| --- | --- |
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular carcinoma and melanoma). | GenBank Acc. No. NM_004484. Nakatsura, et al. (2003) Biochem. Biophys. Res. Commun. 306: 16-25; Capurro, et al. (2003) Gasteroenterol. 125: 89-97; Nakatsura, et al. (2004) Clin. Cancer Res. 10: 6612-6621). |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank Acc. No. L78132. |
| Prostate tumor-inducing gene-1 (PTI-1). | See, e.g., Machlenkin, et al. (2005) Cancer Res. 65: 6435-6442). |
| Prostate-specific gene with homology to G protein-coupled receptor. | See, e.g., Machlenkin, et al. (2005) Cancer Res. 65: 6435-6442). |
| Prostase (an antrogen regulated serine protease). | See, e.g., Machlenkin, et al. (2005) Cancer Res. 65: 6435-6442; GenBank Acc. No. BC096178; BC096176; BC096175. |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. | GenBank Acc. No. NM_001327 (NY-ESO-1) (see also, e.g., Li, et al. (2005) Clin. Cancer Res. 11: 1809-1814; Chen, et al. (2004) Proc. Natl. Acad. Sci. USA. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer Lett. 150: 155-164; Dalerba, et al. (2001) Int. J. Cancer 93: 85-90; Ries, et al. (2005) Int. J. Oncol. 26: 817-824. |
| MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125. | Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443-449; Lin, et al. (2004) Clin. Cancer Res. 10: 5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res. 59: 3157-3165; Scarcella, et al. (1999) Clin. Cancer Res. 5: 335-341. |
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |

TABLE 1-continued

Antigens

| Antigen | Reference |
|---|---|
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |
| N-Acetylglucosaminyl-tranferase V (GnT-V). | Dosaka-Akita, et al. (2004) Clin. Cancer Res. 10: 1773-1779. |
| Elongation factor 2 mutated (ELF2M). | Renkvist, et al. (2001) Cancer Immunol Immunother. 50: 3-15. |
| HOM-MEL-40/SSX2 | Neumann, et al. (2004) Int. J. Cancer 112: 661-668; Scanlan, et al. (2000) Cancer Lett. 150: 155-164. |
| BRDT. | Scanlan, et al. (2000) Cancer Lett. 150: 155-164. |
| SAGE; HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |
| LDLR/FUT fusion protein antigen of melanoma. | Wang, et al. (1999) J. Exp. Med. 189: 1659-1667. |
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | Von Lindern, et al. (1992) Mol. Cell. Biol. 12: 1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GenBank Acc. Nos. P01112; P01116; M54969; M54968; P01111; P01112; K00654. See also, e.g., GenBank Acc. Nos. M26261; M34904; K01519; K01520; BC006499; NM_006270; NM_002890; NM_004985; NM_033360; NM_176795; NM_005343. |
| BRAF (an isoform of RAF). | Tannapfel, et al. (2005) Am. J. Clin. Pathol. 123: 256-2601; Tsao and Sober (2005) Dermatol. Clin. 23: 323-333. |
| Melanoma antigens, including HST-2 melanoma cell antigens. | GenBank Acc. No. NM_206956; NM_206955; NM_206954; NM_206953; NM_006115; NM_005367; NM_004988; AY148486; U10340; U10339; M77481. See, e g., Suzuki, et al. (1999) J. Immunol. 163: 2783-2791. |
| Survivin | GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastroenterol. 10: 3394-3398. |
| NA88-A. | Moreau-Aubry, et al. (2000) J. Exp. Med. 191: 1617-1624. |
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |

TABLE 1-continued

| Antigen | Reference |
|---|---|
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |
| Alpha-fetoprotein (AFP) | Grimm, et al. (2000) Gastroenterol. 119: 1104-1112. |
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Gp100/pmel-17. | GenBank Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infection Immunity 73: 1939-1946. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | U.S. Published Pat. Appl. No. 20020150588 of Allison, et al. |
| CASP-8; FLICE; MACH. | Mandruzzato, et al. (1997) J. Exp. Med. 186: 785-793. |

TABLE 1-continued

Antigens

| Antigen | Reference |
| --- | --- |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| EphA2 | See, e.g., U.S. Patent Publication No. 2005/0281783 A1; Genbank Accession No. NM_004431 (human); Genbank Accession No. NM_010139 (Mouse); Genbank Accession No. AB038986 (Chicken, partial sequence); GenBank Accession Nos. NP_004422, AAH37166, and AAA53375 (human); GenBank Accession Nos. NP_034269 (mouse), AAH06954 (mouse), XP_345597 (rat), and BAB63910 (chicken). |
| EGFRvIII | See, e.g., WO/2012/068360 |

Francisella tularensis antigens

| | |
| --- | --- |
| *Francisella tularensis* A and B. | Complete genome of subspecies Schu S4 (GenBank Acc. No. AJ749949); of subspecies Schu 4 (GenBank Acc. No. NC_006570). Outer membrane protein (43 kDa) Bevanger, et al. (1988) J. Clin. Microbiol. 27: 922-926; Porsch-Ozcurumez, et al. (2004) Clin. Diagnostic. Lab. Immunol. 11: 1008-1015). Antigenic components of *F. tularensis* include, e.g., 80 antigens, including 10 kDa and 60 kDa chaperonins (Havlasova, et al. (2002) Proteomics 2: 857-86), nucleoside diphosphate kinase, isocitrate dehydrogenase, RNA-binding protein Hfq, the chaperone ClpB (Havlasova, et al. (2005) Proteomics 5: 2090-2103). See also, e.g., Oyston and Quarry (2005) Antonie Van Leeuwenhoek 87: 277-281; Isherwood, et al. (2005) Adv. Drug Deliv. Rev. 57: 1403-1414; Biagini, et al. (2005) Anal. Bioanal. Chem. 382: 1027-1034. |

Malarial antigens

| | |
| --- | --- |
| Circumsporozoite protein (CSP); SSP2; HEP17; Exp-1 orthologs found in *P. falciparum*; and LSA-1. | See, e.g., Haddad, et al. (2004) Infection Immunity 72: 1594-1602; Hoffman, et al. (1997) Vaccine 15: 842-845; Oliveira-Ferreira and Daniel-Ribeiro (2001) Mem. Inst. Oswaldo Cruz, Rio de Janeiro 96: 221-227. CSP (see, e.g., GenBank Acc. No. AB121024). SSP2 (see, e.g., GenBank Acc. No. AF249739). LSA-1 (see, e.g., GenBank Acc. No. Z30319). |
| Ring-infected erythrocyte survace protein (RESA); merozoite surface protein 2 (MSP2); Spf66; merozoite surface protein 1(MSP1); 195A; BVp42. | See, e.g., Stirnadel, et al. (2000) Int. J. Epidemiol. 29: 579-586; Krzych, et al. (1995) J. Immunol. 155: 4072-4077. See also, Good, et al. (2004) Immunol. Rev. 201: 254-267; Good, et al. (2004) Ann. Rev. Immunol. 23: 69-99. MSP2 (see, e.g., GenBank Acc. No. X96399; X96397). MSP1 (see, e.g., GenBank Acc. No. X03371). RESA (see, e.g., GenBank Acc. No. X05181; X05182). |
| Apical membrane antigen 1 (AMA1). | See, e.g., Gupta, et al. (2005) Protein Expr. Purif. 41: 186-198. AMA1 (see, e.g., GenBank Acc. No. A'13; AJ494905; AJ490565). |

Viruses and viral antigens

| | |
| --- | --- |
| Hepatitis A | GenBank Acc. Nos., e.g., NC_001489; AY644670; X83302; K02990; M14707. |
| Hepatitis B | Complete genome (see, e.g., GenBank Acc. Nos. AB214516; NC_003977; AB205192; AB205191; AB205190; AJ748098; AB198079; AB198078; AB198076; AB074756). |
| Hepatitis C | Complete genome (see, e.g., GenBank Acc. Nos. NC_004102; AJ238800; AJ238799; AJ132997; AJ132996; AJ000009; D84263). |

TABLE 1-continued

Antigens

| Antigen | Reference |
|---|---|
| Hepatitis D | GenBank Acc. Nos, e.g. NC_001653; AB118847; AY261457. |
| Human papillomavirus, including all 200+ subtypes (classed in 16 groups), such as the high risk subtypes 16, 18, 30, 31, 33, 45. | See, e.g., Trimble, et al. (2003) Vaccine 21: 4036-4042; Kim, et al. (2004) Gene Ther. 11: 1011-1018; Simon, et al. (2003) Eur. J. Obstet. Gynecol. Reprod. Biol. 109: 219-223; Jung, et al. (2004) J. Microbiol. 42: 255-266; Damasus-Awatai and Freeman-Wang (2003) Curr. Opin. Obstet. Gynecol. 15: 473-477; Jansen and Shaw (2004) Annu. Rev. Med. 55: 319-331; Roden and Wu (2003) Expert Rev. Vaccines 2: 495-516; de Villiers, et al. (2004) Virology 324: 17-24; Hussain and Paterson (2005) Cancer Immunol. Immunother. 54: 577-586; Molijn, et al. (2005) J. Clin. Virol. 32 (Suppl. 1) S43-S51. GenBank Acc. Nos. AY686584; AY686583; AY686582; NC_006169; NC_006168; NC_006164; NC_001355; NC_001349; NC_005351; NC_001596). |
| *Human T-cell lymphotropic virus* (HTLV) types I and II, including the HTLV type I subtypes *Cosmopolitan*, *Central African*, and *Austro-Melanesian*, and the HTLV type II subtypes Iia, Iib, Iic, and Iid. | See, e.g., Capdepont, et al. (2005) AIDS Res. Hum. Retrovirus 21: 28-42; Bhigjee, et al. (1999) AIDS Res. Hum. Restrovirus 15: 1229-1233; Vandamme, et al. (1998) J. Virol. 72: 4327-4340; Vallejo, et al. (1996) J. Acquir. Immune Defic. Syndr. Hum. Retrovirol. 13: 384-391. HTLV type I (see, e.g., GenBank Acc. Nos. AY563954; AY563953. HTLV type II (see, e.g., GenBank Acc. Nos. L03561; Y13051; AF139382). |
| Coronaviridae, including *Coronaviruses*, such as *SARS-coronavirus* (SARS-CoV), and *Toroviruses*. | See, e.g., Brian and Baric (2005) Curr. Top. Microbiol. Immunol. 287: 1-30; Gonzalez, et al. (2003) Arch. Virol. 148: 2207-2235; Smits, et al. (2003) J. Virol. 77: 9567-9577; Jamieson, et al. (1998) J. Infect. Dis. 178: 1263-1269 (GenBank Acc. Nos. AY348314; NC_004718; AY394850). |
| *Rubella virus*. | GenBank Acc. Nos. NC_001545; AF435866. |
| *Mumps virus*, including the genotypes A, C, D, G, H, and I. | See, e.g., Orvell, eta l. (2002) J. Gen. Virol. 83: 2489-2496. See, e.g., GenBank Acc. Nos. AY681495; NC_002200; AY685921; AF201473. |
| *Coxsackie virus A* including the serotypes 1, 11, 13, 15, 17, 18, 19, 20, 21, 22, and 24 (also known as *Human enterovirus C*; HEV-C). | See, e.g., Brown, et al. (2003) J. Virol. 77: 8973-8984. GenBank Acc. Nos. AY421768; AY790926: X67706. |
| *Coxsackie virus B*, including subtypes 1-6. | See, e.g., Ahn, et al. (2005) J. Med. Virol. 75: 290-294; Patel, et al. (2004) J. Virol. Methods 120: 167-172; Rezig, et al. (2004) J. Med. Virol. 72: 268-274. GenBank Acc. No. X05690. |
| *Human enteroviruses* including, e.g., *human enterovirus A* (HEV-A, CAV2 to CAV8, CAV10, CAV12, CAV14, CAV16, and EV71) and also including HEV-B (CAV9, CBV1 to CBV6, E1 to E7, E9, E11 to E21, E24 to E27, E29 to E33, and EV69 and E73), as well as HEV. | See, e.g., Oberste, et al. (2004) J. Virol. 78: 855-867. *Human enterovirus A* (GenBank Acc. Nos. NC_001612); *human enterovirus B* (NC_001472); *human enterovirus C* (NC_001428); *human enterovirus D* (NC_001430). *Simian enterovirus A* (GenBank Acc. No. NC_003988). |
| *Polioviruses* including PV1, PV2, and PV3. | See, e.g., He, et al. (2003) J. Virol. 77: 4827-4835; Hahsido, et al. (1999) Microbiol. Immunol. 43: 73-77. GenBank Acc. No. AJ132961 (type 1); AY278550 (type 2); X04468 (type 3). |

TABLE 1-continued

Antigens

| Antigen | Reference |
|---|---|
| Viral encephalitides viruses, including *equine encephalitis*, *Venezuelan equine encephalitis* (VEE) (including subtypes IA, IB, IC, ID, IIIC, IIID), *Eastern equine encephalitis* (EEE), *Western equine encephalitis* (WEE), *St. Louis encephalitis*, *Murray Valley* (*Australian*) *encephalitis*, *Japanese encephalitis*, and *tick-born encephalitis*. | See, e.g., Hoke (2005) Mil. Med. 170: 92-105; Estrada-Franco, et al. (2004) Emerg. Infect. Dis. 10: 2113-2121; Das, et al. (2004) Antiviral Res. 64: 85-92; Aguilar, et al. (2004) Emerg. Infect. Dis. 10: 880-888; Weaver, et al. (2004) Arch. Virol. Suppl. 18: 43-64; Weaver, et al. (2004) Annu. Rev. Entomol. 49: 141-174. *Eastern equine encephalitis* (GenBank Acc. No. NC_003899; AY722102); *Western equine encephalitis* (NC_003908). |
| Human herpesviruses, including *cytomegalovirus* (CMV), *Epstein-Barr virus* (EBV), *human herpesvirus-1* (HHV-1), HHV-2, HHV-3, HHV-4, HHV-5, HHV-6, HHV-7, HHV-8, herpes B virus, *herpes simplex virus* types 1 and 2 (HSV-1, HSV-2), and *varicella zoster virus* (VZV). | See, e.g., Studahl, et al. (2000) Scand. J. Infect. Dis. 32: 237-248; Padilla, et al. (2003) J. Med. Virol. 70 (Suppl. 1) S103-S110; Jainkittivong and Langlais (1998) Oral Surg. Oral Med. 85: 399-403. GenBank Nos. NC_001806 (*herpesvirus* 1); NC_001798 (*herpesvirus* 2); X04370 and NC_001348 (*herpesvirus* 3); NC_001345 (*herpesvirus* 4); NC_001347 (*herpesvirus* 5); X83413 and NC_000898 (*herpesvirus* 6); NC_001716 (*herpesvirus* 7). *Human herpesviruses* types 6 and 7 (HHV-6; HHV-7) are disclosed by, e.g., Padilla, et al. (2003) J. Med. Virol. 70 (Suppl. 1)S103-S110. *Human herpesvirus 8* (HHV-8), including subtypes A-E, are disclosed in, e.g., Treurnicht, et al. (2002) J. Med. Virol. 66: 235-240. |
| HIV-1 including group M (including subtypes A to J) and group O (including any distinguishable subtypes) (HIV-2, including subtypes A-E. | See, e.g., Smith, et al. (1998) J. Med. Virol. 56: 264-268. See also, e.g., GenBank Acc. Nos. DQ054367; NC_001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| *Epstein-Barr virus* (EBV), including subtypes A and B. | See, e.g., Peh, et al. (2002) Pathology 34: 446-450. *Epstein-Barr virus* strain B95-8 (GenBank Acc. No. V01555). |
| Reovirus, including serotypes and strains 1, 2, and 3, type 1 Lang, type 2 Jones, and type 3 Dearing. | See, e.g., Barthold, et al. (1993) Lab. Anim. Sci. 43: 425-430; Roner, et al. (1995) Proc. Natl. Acad. Sci. USA 92: 12362-12366; Kedl, et al. (1995) J. Virol. 69: 552-559. GenBank Acc. No. K02739 (sigma-3 gene surface protein). |
| *Cytomegalovirus* (CMV) subtypes include CMV subtypes I-VII. | See, e.g., Chern, et al. (1998) J. Infect. Dis. 178: 1149-1153; Vilas Boas, et al. (2003) J. Med. Virol. 71: 404-407; Trincado, et al. (2000) J. Med. Virol. 61: 481-487. GenBank Acc. No. X17403. |
| *Rhinovirus*, including all serotypes. | Human *rhinovirus* 2 (GenBank Acc. No. X02316); Human *rhinovirus* B (GenBank Acc. No. NC_001490); Human *rhinovirus* 89 (GenBank Acc. No. NC_001617); Human *rhinovirus* 39 (GenBank Acc. No. AY751783). |
| Adenovirus, including all serotypes. | AY803294; NC_004001; AC_000019; AC_000018; AC_000017; AC_000015; AC_000008; AC_000007; AC_000006; AC_000005; AY737798; AY737797; NC_003266; NC_002067; AY594256; AY594254; AY875648; AJ854486; AY163756; AY594255; AY594253; NC_001460; NC_001405; AY598970; AY458656; AY487947; NC_001454; AF534906; AY45969; AY128640; L19443; AY339865; AF532578. |
| Filoviruses, including *Marburg virus* and *Ebola virus*, and strains such as Ebola-Sudan (EBO-S), Ebola-Zaire (EBO-Z), and Ebola-Reston (EBO-R). | See, e.g., Geisbert and Jahrling (1995) Virus Res. 39: 129-150; Hutchinson, et al. (2001) J. Med. Virol. 65: 561-566. *Marburg virus* (see, e.g., GenBank Acc. No. NC_001608). *Ebola virus* (see, e.g., GenBank Acc. Nos. NC_006432; AY769362; NC_002549; AF272001; AF086833). |

TABLE 1-continued

| Antigens | |
|---|---|
| Antigen | Reference |
| Arenaviruses, including *lymphocytic choriomeningitis* (LCM) *virus*, *Lassa virus*, *Junin virus*, and *Machupo virus*. | *Junin virus*, segment S (GenBank Acc. No. NC_005081); *Junin virus*, segment L (GenBank Acc. No. NC_005080). |
| Rabies virus. | See, e.g., GenBank Acc. Nos. NC_001542; AY956319; AY705373; AF499686; AB128149; AB085828; AB009663. |
| Arboviruses, including *West Nile virus*, *Dengue viruses* 1 to 4, *Colorado tick fever virus*, *Sindbis virus*, Togaviraidae, Flaviviridae, Bunyaviridae, Reoviridae, Rhabdoviridae, Orthomyxoviridae, and the like. | *Dengue virus* type 1 (see, e.g., GenBank Acc. Nos. AB195673; AY762084). *Dengue virus* type 2 (see, e.g., GenBank Acc. Nos. NC_001474; AY702040; AY702039; AY702037). *Dengue virus* type 3 (see, e.g., GenBank Acc. Nos. AY923865; AT858043). *Dengue virus* type 4 (see, e.g., GenBank Acc. Nos. AY947539; AY947539; AF326573). *Sindbis virus* (see, e.g., GenBank Acc. Nos. NC_001547; AF429428; J02363; AF103728). *West Nile virus* (see, e.g., GenBank Acc. Nos. NC_001563; AY603654). |
| Poxvirus including *orthopoxvirus* (*variola virus*, *monkeypox virus*, *vaccinia virus*, *cowpox virus*), *yatapoxvirus* (*tanapox virus*, *Yaba monkey tumor virus*), *parapoxvirus*, and *molluscipoxvirus*. | *Viriola virus* (see, e.g., GenBank Acc. Nos. NC_001611; Y16780; X72086; X69198). |
| Yellow fever. | See, e.g., GenBank Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) J. Clin. Microbiol. 35: 1122-1130; Sjolander, et al. (2002) Epidemiol. Infect. 128: 99-103; Zeier, et al. (2005) Virus Genes 30: 157-180. GenBank Acc. No. NC_005222 and NC_005219 (Hantavirus). See also, e.g., GenBank Acc. Nos. NC_005218; NC_005222; NC_005219. |
| *Flaviviruses*, including *Dengue virus*, *Japanese encephalitis virus*, *West Nile virus*, and *yellow fever virus*. | See, e.g., Mukhopadhyay, et al. (2005) Nature Rev. Microbiol. 3: 13-22. GenBank Acc. Nos NC_001474 and AY702040 (*Dengue*). GenBank Acc. Nos. NC_001563 and AY603654. |
| Measles virus. | See, e.g., GenBank Acc. Nos. AB040874 and AY486084. |
| Human parainfluenzaviruses (HPV), including HPV types 1-56. | Human parainfluenza virus 2 (see, e.g., GenBank Acc. Nos. AB176531; NC003443). Human parainfluenza virus 3 (see, e.g., GenBank Acc. No. NC_001796). |
| *Influenza virus*, including *influenza virus* types *A*, *B*, and *C*. | *Influenza* nucleocapsid (see, e.g., GenBank Acc. No. AY626145). *Influenza* hemagglutinin (see, e.g., GenBank Acc. Nos. AY627885; AY555153). *Influenza* neuraminidase (see, e.g., GenBank Acc. Nos. AY555151; AY577316). *Influenza* matrix protein 2 (see, e.g., GenBank Acc. Nos. AY626144(. *Influenza* basic protein 1 (see, e.g., GenBank Acc. No. AY627897). *Influenza* polymerase acid protein (see, e.g., GenBank Acc. No. AY627896). *Influenza* nucleoprotein (see, e.g., GenBank Acc. Nno. AY627895). |
| *Influenza A virus* subtypes, e.g., swine viruses (SIV): H1N1 *influenzaA* and swine *influenza* virus. | Hemagglutinin of H1N1 (GenBank Acc. No. S67220). *Influenza A virus* matrix protein (GenBank Acc. No. AY700216). *Influenza virus A* H5H1 nucleoprotein (GenBank Acc. No. AY646426). H1N1 haemagglutinin (GenBank Acc. No. D00837). See also, GenBank Acc. Nos. BD006058; BD006055; BD006052. See also, e.g., Wentworth, et al. (1994) J. Virol. 68: 2051-2058; Wells, et al. (1991) J.A.M.A. 265: 478-481. |
| Respiratory syncytial virus (RSV), including subgroup A and subgroup B. | Respiratory syncytial virus (RSV) (see, e.g., GenBank Acc. Nos. AY353550; NC_001803; NC001781). |

TABLE 1-continued

Antigens

| Antigen | Reference |
|---|---|
| Rotaviruses, including human rotaviruses A to E, bovine rotavirus, rhesus monkey rotavirus, and human-RVV reassortments. | Human rotavirus C segment 8 (GenBank Acc. No. AJ549087); Human rotavirus G9 strain outer capsid protein (see, e.g., GenBank Acc. No. DQ056300); Human rotavirus B strain nonstructural protein 4 (see, e.g., GenBank Acc. No. AY548957); human rotavirus A strain major inner capsid protein (see, e.g., GenBank Acc. No. AY601554). |
| Polyomavirus, including simian virus 40 (SV40), JC virus (JCV) and BK virus (BKV). | See, e.g., Engels, et al. (2004) J. Infect. Dis. 190: 2065-2069; Vilchez and Butel (2004) Clin. Microbiol. Rev. 17: 495-508; Shivapurkar, et al. (2004) Cancer Res. 64: 3757-3760; Carbone, et al. (2003) Oncogene 2: 5173-5180; Barbanti-Brodano, et al. (2004) Virology 318: 1-9) (SV40 complete genome in, e.g., GenBank Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79: 2481-2489. Segments of Eyach virus (see, e.g., GenBank Acc. Nos. AF282475; AF282472; AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Calciviruses, including the genogroups Norwalk, Snow Mountain group (SMA), and Saaporo. | Snow Mountain virus (see, e.g., GenBank Acc. No. AY134748). |
| Parvoviridae, including dependovirus, parvovirus (including parvovirus B19), and erythrovirus. | See, e.g., Brown (2004) Dev. Biol. (Basel) 118: 71-77; Alvarez-Lafuente, et al. (2005) Ann. Rheum. Dis. 64: 780-782; Ziyaeyan, et al. (2005) Jpn. J. Infect. Dis. 58: 95-97; Kaufman, et al. (2005) Virology 332: 189-198. |

Other organisms for which suitable antigens are known in the art include, but are not limited to, Chlamydia trachomatis, Streptococcus pyogenes (Group A Strep), Streptococcus agalactia (Group B Strep), Streptococcus pneumonia, Staphylococcus aureus, Escherichia coli, Haemophilus influenzae, Neisseria meningitidis, Neisseria gonorrheae, Vibrio cholerae, Salmonella species (including typhi, typhimurium), enterica (including Helicobactor pylori Shigella flexneri and other Group D shigella species), Burkholderia mallei, Burkholderia pseudomallei, Klebsiella pneumonia, Clostridium species (including C. difficile), Vibrio parahaemolyticus and V. vulnificus. This list is not meant to be limiting.

In certain embodiments, antigen sequence(s) may be expressed as a single polypeptide fused to an amino-terminal portion of the L. monocytogenes ActA protein which permits expression and secretion of a fusion protein from the bacterium within the vaccinated host. In these embodiments, the antigenic construct may be a polynucleotide comprising a promoter operably linked to a nucleic acid sequence encoding a fusion protein, wherein the fusion protein comprises (a) modified ActA and (b) one or more antigenic epitopes to be expressed as a fusion protein following the modified ActA sequence.

By "modified ActA" is meant a contiguous portion of the *L. monocytogenes* ActA protein which comprises at least the ActA signal sequence, but does not comprise the entirety of the ActA sequence, or that has at least about 80% sequence identity, at least about 85% sequence identity, at least about 90% sequence identity, at least about 95% sequence identity, or at least about 98% sequence identity to such an ActA sequence. In some embodiments, the promoter is ActA promoter from WO07/103225; and WO07/117371, each of which is incorporated by reference in its entirety herein.

By way of example, the modified ActA may comprise at least the first 59 amino acids of ActA, or a sequence having at least about 80% sequence identity, at least about 85% sequence identity, at least about 90% sequence identity, at least about 95% sequence identity, or at least about 98% sequence identity to at least the first 59 amino acids of ActA. In some embodiments, the modified ActA comprises at least the first 100 amino acids of ActA, or a sequence having at least about 80% sequence identity, at least about 85% sequence identity, at least about 90% sequence identity, at least about 95% sequence identity, or at least about 98% sequence identity to the first 100 amino acids of ActA. In other words, in some embodiments, the modified ActA sequence corresponds to an N-terminal fragment of ActA (including the ActA signal sequence) that is truncated at residue 100 or thereafter. ActA-N100 has the following sequence (SEQ ID NO: 3):

```
VGLNRFMRAM MVVFITANCI TINPDIIFAA TDSEDSSLNT DEWEEEKTEE     50

QPSEVNTGPR YETAREVSSR DIEELEKSNK VKNTNKADLI AMLKAKAEKG    100
```

In this sequence, the first residue is depicted as a valine; the polypeptide is synthesized by *Listeria* with a methionine in this position. Thus, ActA-N100 may also have the following sequence (SEQ ID NO:4):

```
MGLNRFMRAM MVVFITANCI TINPDIIFAA TDSEDSSLNT DEWEEEKTEE    50

QPSEVNTGPR YETAREVSSR DIEELEKSNK VKNTNKADLI AMLKAKAEKG   100
```

ActA-N100 may also comprise one or more additional residues lying between the C-terminal residue of the modified ActA and the antigen sequence. In the following sequences, ActA-N100 is extended by two residues added by inclusion of a BamH1 site (SEQ ID NO: 5):

```
VGLNRFMRAM MVVFITANCI TINPDIIFAA TDSEDSSLNT DEWEEEKTEE    50

QPSEVNTGPR YETAREVSSR DIEELEKSNK VKNTNKADLI AMLKAKAEKG   100

GS
``` which when synthesized with a first residue methionine has the sequence (SEQ ID NO: 6):

```
MGLNRFMRAM MVVFITANCI TINPDIIFAA TDSEDSSLNT DEWEEEKTEE
     50

QPSEVNTGPR YETAREVSSR DIEELEKSNK VKNTNKADLI AMLKAKAEKG
    100

GS.
```

Alternatively, antigen sequence(s) are preferably expressed as a single polypeptide fused to a modified amino-terminal portion of the *L. monocytogenes* LLO protein which permits expression and secretion of a fusion protein from the bacterium within the vaccinated host. In these embodiments, the antigenic construct may be a polynucleotide comprising a promoter operably linked to a nucleic acid sequence encoding a fusion protein, wherein the fusion protein comprises (a) modified LLO and (b) one or more antigenic epitopes to be expressed as a fusion protein following the modified LLO sequence. The LLO signal sequence is MKKIMLVFIT LILVSLPIAQ QTEAK (SEQ ID NO: 1). In some embodiments, the promoter is hly promoter.

In some embodiments, the modified LLO comprises a modified form of about the first 441 amino acids of LLO, referred to herein as LLO-N441. LLO-N441 has the following sequence

```
(SEQ ID NO: 2):
            10         20         30         40         50         60
    MKKIMLVFIT LILVSLPIAQ QTEAKDASAF NKENSISSMA PPASPPASPK TPIEKKHADE 70         80         90        100        110        120
    IDKYIQGLDY NKNNVLVYHG DAVTNVPPRK GYKDGNEYIV VEKKKKSINQ NNADIQVVNA 130        140        150        160        170        180
    ISSLTYPGAL VKANSELVEN QPDVLPVKRD SLTLSIDLPG MTNQDNKIVV KNATKSNVNN 190        200        210        220        230        240
    AVNTLVERWN EKYAQAYPNV SAKIDYDDEM AYSESQLIAK FGTAFKAVNN SLNVNFGAIS 250        260        270        280        290        300
    EGKMQEEVIS FKQIYYNVNV NEPTRPSRFF GKAVTKEQLQ ALGVNAENPP AYISSVAYGR 310        320        330        340        350        360
    QVYLKLSTNS HSTKVKAAFD AAVSGKSVSG DVELTNIIKN SSFKAVIYGG SAKDEVQIID 370        380        390        400        410        420
    GNLGDLRDIL KKGATFNRET PGVPIAYTTN FLKDNELAVI KNNSEYIETT SKAYTDGKIN 430        440
    IDHSGGYVAQ FNISWDEVNY D
```

As sequences encoded by one organism are not necessarily codon optimized for optimal expression in a chosen vaccine platform bacterial strain, the present invention also provides nucleic acids that are altered by codon optimized for expressing by a bacterium such as *L. monocytogenes*.

In various embodiments, at least one percent of any non-optimal codons are changed to provide optimal codons, more normally at least five percent are changed, most normally at least ten percent are changed, often at least 20% are changed, more often at least 30% are changed, most often at least 40%, usually at least 50% are changed, more usually at least 60% are changed, most usually at least 70% are changed, optimally at least 80% are changed, more optimally at least 90% are changed, most optimally at least 95% are changed, and conventionally 100% of any non-optimal codons are codon-optimized for *Listeria* expression (Table 2).

TABLE 2

Optimal codons for expression in *Listeria*.

| | Amino Acid | | | | | | | | |
|---|---|---|---|---|---|---|---|---|---|
| | A | R | N | D | C | Q | E | G | H | I |
| Optimal *Listeria* codon | GCA | CGU | AAU | GAU | UGU | CAA | GAA | GGU | CAU | AUU |

| | Amino Acid | | | | | | | | |
|---|---|---|---|---|---|---|---|---|---|
| | L | K | M | F | P | S | T | W | Y | V |
| Optimal *Listeria* codon | UUA | AAA | AUG | UUU | CCA | AGU | ACA | UGG | UAU | GUU |

The invention supplies a number of *Listeria* species and strains for making or engineering an attenuated bacterium of the present invention. The *Listeria* of the present invention is not to be limited by the species and strains disclosed in Table 3.

TABLE 3

Strains of *Listeria* suitable for use in the present invention, e.g., as a vaccine or as a source of nucleic acids.

| | |
|---|---|
| *L. monocytogenes* 10403S wild type. | Bishop and Hinrichs (1987) J. Immunol. 139: 2005-2009; Lauer, et al. (2002) J. Bact. 184: 4177-4186. |
| *L. monocytogenes* DP-L4056 (phage cured). The prophage-cured 10403S strain is designated DP-L4056. | Lauer, et al. (2002) J. Bact. 184: 4177-4186. |
| *L. monocytogenes* DP-L4027, which is DP-L2161, phage cured, deleted in hly gene. | Lauer, et al. (2002) J. Bact. 184: 4177-4186; Jones and Portnoy (1994) Infect. Immunity 65: 5608-5613. |
| *L. monocytogenes* DP-L4029, which is DP-L3078, phage cured, deleted in ActA. | Lauer, et al. (2002) J. Bact. 184: 4177-4186; Skoble, et al. (2000) J. Cell Biol. 150: 527-538. |
| *L. monocytogenes* DP-L4042 (delta PEST) | Brockstedt, et al. (2004) Proc. Natl. Acad. Sci. USA 101: 13832-13837; supporting information. |
| *L. monocytogenes* DP-L4097 (LLO-S44A). | Brockstedt, et al. (2004) Proc. Natl. Acad. Sci. USA 101: 13832-13837; supporting information. |
| *L. monocytogenes* DP-L4364 (delta lplA; lipoate protein ligase). | Brockstedt, et al. (2004) Proc. Natl. Acad. Sci. USA 101: 13832-13837; supporting information. |
| *L. monocytogenes* DP-L4405 (delta inlA). | Brockstedt, et al. (2004) Proc. Natl. Acad. Sci. USA 101: 13832-13837; supporting information. |
| *L. monocytogenes* DP-L4406 (delta in1B). | Brockstedt, et al. (2004) Proc. Natl. Acad. Sci. USA 101: 13832-13837; supporting information. |
| *L. monocytogenes* CS-L0001 (delta ActA-delta inlB ). | Brockstedt, et al. (2004) Proc. Natl. Acad. Sci. USA 101: 13832-13837; supporting information. |
| *L. monocytogenes* CS-L0002 (delta ActA-delta lplA). | Brockstedt, et al. (2004) Proc. Natl. Acad. Sci. USA 101: 13832-13837; supporting information. |
| *L. monocytogenes* CS-L0003 (L461T-delta lplA). | Brockstedt, et al. (2004) Proc. Natl. Acad. Sci. USA 101: 13832-13837; supporting information. |

TABLE 3-continued

Strains of *Listeria* suitable for use in the present invention, e.g., as a vaccine or as a source of nucleic acids.

| Strain | Reference |
|---|---|
| *L. monocytogenes* DP-L4038 (delta ActA-LLO L461T). | Brockstedt, et al. (2004) Proc. Natl. Acad. Sci. USA 101: 13832-13837; supporting information. |
| *L. monocytogenes* DP-L4384 (S44A-LLO L461T). | Brockstedt, et al. (2004) Proc. Natl. Acad. Sci. USA 101: 13832-13837; supporting information. |
| *L. monocytogenes*. Mutation in lipoate protein ligase (LplA1). | O'Riordan, et al. (2003) Science 302: 462-464. |
| *L. monocytogenes* DP-L4017 (10403S hly (L461T) point mutation in hemolysin gene. | U.S. Provisional Pat. Appl. Ser. No. 60/490,089 filed Jul. 24, 2003. |
| *L. monocytogenes* EGD. | GenBank Acc. No. AL591824. |
| *L. monocytogenes* EGD-e. | GenBank Acc. No. NC_003210. ATCC Acc. No. BAA-679. |
| *L. monocytogenes* strain EGD, complete genome, segment 3/12 | GenBank Acc. No. AL591975 |
| *L. monocytogenes*. | ATCC Nos. 13932; 15313; 19111-19120; 43248-43251; 51772-51782. |
| *L. monocytogenes* DP-L4029 deleted in uvrAB. | U.S. Provisional Pat. Appl. Ser. No. 60/541,515 filed Feb. 2, 2004; U.S. Provisional Pat. Appl. Ser. No. 60/490,080 filed Jul. 24, 2003. |
| *L. monocytogenes* DP-L4029 deleted in uvrAB treated with a psoralen. | U.S. Provisional Pat. Appl. Ser. No. 60/541,515 filed Feb. 2, 2004. |
| *L. monocytogenes* delta actA delta inlB delta uvrAB | Brockstedt (2005) Nature Medicine and KBMA patent |
| *L. monocytogenes* delta actA delta inlB delta uvrAB treated with psoralen | Brockstedt (2005) Nature Medicine and KBMA patent |
| *L. monocytogenes* delta actA delta inlB delta uvrAB prfA(G155S) | Lauer et al, (2008) Infect. Immun. And WO 2009/143085 |
| *L. monocytogenes* delta actA delta inlB delta uvrAB prfA(G155S) treated with psoralen | Lauer et al, (2008) Infect. Immun. And WO 2009/143085 |
| *L. monocytogenes* ActA-/inlB-double mutant. | Deposited with ATCC on Oct. 3, 2003. Acc. No. PTA-5562. |
| *L. monocytogenes* lplA mutant or hly mutant. | U.S. Pat. Applic. No. 20040013690 of Portnoy, et al. |
| *L. monocytogenes* DAL/DAT double mutant. | U.S. Pat. Applic. No. 20050048081 of Frankel and Portnoy. |
| *L. monocytogenes* str. 4b F2365. | GenBank Acc. No. NC_002973. |
| *Listeria ivanovii* | ATCC No. 49954 |
| *Listeria innocua* Clip11262. | GenBank Acc. No. NC_003212; AL592022. |
| *Listeria innocua*, a naturally occurring hemolytic strain containing the PrfA-regulated virulence gene cluster. | Johnson, et al. (2004) Appl. Environ. Microbiol. 70: 4256-4266. |
| *Listeria seeligeri*. | Howard, et al. (1992) Appl. Eviron. Microbiol. 58: 709-712. |
| *Listeria innocua* with *L. monocytogenes* pathogenicity island genes. | Johnson, et al. (2004) Appl. Environ. Microbiol. 70: 4256-4266. |
| *Listeria innocua* with *L. monocytogenes* internalin A gene, e.g., as a plasmid or as a genomic nucleic acid. | See, e.g., Lingnau, et al. (1995) Infection Immunity 63: 3896-3903; Gaillard, et al. (1991) Cell 65: 1127-1141). |

The present invention encompasses reagents and methods that comprise the above *Listerial* strains, as well as these strains that are modified, e.g., by a plasmid and/or by genomic integration, to contain a nucleic acid encoding one of, or any combination of, the following genes: hly (LLO; listeriolysin); iap (p60); inlA; inlB; inlC; dal (alanine racemase); daaA (dat; D-amino acid aminotransferase); plcA; plcB; ActA; or any nucleic acid that mediates growth, spread, breakdown of a single walled vesicle, breakdown of a double walled vesicle, binding to a host cell, uptake by a host cell. The present invention is not to be limited by the particular strains disclosed above.

4. Therapeutic Compositions

The vaccine compositions described herein can be administered to a host, either alone or in combination with a pharmaceutically acceptable excipient, in an amount sufficient to induce an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression. The vaccines of the present invention can be stored, e.g., frozen, lyophilized, as a suspension, as a cell paste, or complexed with a solid matrix or gel matrix.

In certain embodiments, after the subject has been administered an effective dose of a first vaccine to prime the immune response, a second vaccine is administered. This is referred to in the art as a "prime-boost" regimen. In such a regimen, the compositions and methods of the present invention may be used as the "prime" delivery, as the "boost" delivery, or as both a "prime" and a "boost." Any number of "boost" immunizations can be delivered in order to maintain the magnitude or effectiveness of a vaccine-induced immune response.

In certain embodiments it may be desirable to induce both $\alpha\beta$ and $\gamma\delta$ T cell populations in a subject. A prime-boost strategy can be taken to accomplish this objective. According to this immunization regimen, a subject is administered a first vaccine as a prime to induce $\alpha\beta$ T cell populations, but not $\gamma\delta$ T cell populations. The subject can then be administered a series of doses to induce both $\alpha\beta$ T cell populations and γδ T cell populations. It should be recognized that the vaccines used in the prime-boost immunization regimen can each be administered more than one time. As a non-limiting example, priming of αβ T cell populations can be accomplished with two prime vaccinations, followed by boosting with a vaccine to induce both αβ T cell populations and γδ T cells.

It should be understood, however, that each of the prime and boost need not utilize the methods and compositions of the present invention. Rather, the present invention contemplates the use of other vaccine modalities together with the bacterial vaccine methods and compositions of the present invention. The following are examples of suitable mixed prime-boost regimens: a DNA (e.g., plasmid) vaccine prime/bacterial vaccine boost; a viral vaccine prime/bacterial vaccine boost; a protein vaccine prime/bacterial vaccine boost; a DNA prime/bacterial vaccine boost plus protein vaccine boost; a bacterial vaccine prime/DNA vaccine boost; a bacterial vaccine prime/viral vaccine boost; a bacterial vaccine prime/protein vaccine boost; a bacterial vaccine prime/bacterial vaccine boost plus protein vaccine boost; etc. This list is not meant to be limiting The prime vaccine and boost vaccine may be administered by the same route or by different routes. The term "different routes" encompasses, but is not limited to, different sites on the body, for example, a site that is oral, non-oral, enteral, parenteral, rectal, intranode (lymph node), intravenous, arterial, subcutaneous, intradermal, intramuscular, intratumor, peritumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine or vaccines in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

In certain embodiments, administration of the boost vaccination can be initiated at about 5 days after the prime vaccination is initiated; about 10 days after the prime vaccination is initiated; about 15 days; about 20 days; about 25 days; about 30 days; about 35 days; about 40 days; about 45 days; about 50 days; about 55 days; about 60 days; about 65 days; about 70 days; about 75 days; about 80 days; about 6 months, and about 1 year after administration of the prime vaccination is initiated. Preferably one or both of the prime and boost vaccination comprises delivery of a composition of the present invention.

A "pharmaceutically acceptable excipient" or "diagnostically acceptable excipient" includes but is not limited to, sterile distilled water, saline, phosphate buffered solutions, amino acid based buffers, or bicarbonate buffered solutions. An excipient selected and the amount of excipient used will depend upon the mode of administration. Administration may be oral, intravenous, subcutaneous, dermal, intradermal, intramuscular, mucosal, parenteral, intraorgan, intralesional, intranasal, inhalation, intraocular, intramuscular, intravascular, intranodal, by scarification, rectal, intraperitoneal, or any one or combination of a variety of well-known routes of administration. The administration can comprise an injection, infusion, or a combination thereof.

Administration of the vaccine of the present invention by a non-oral route can avoid tolerance. Methods are known in the art for administration intravenously, subcutaneously, intradermally, intramuscularly, intraperitoneally, orally, mucosally, by way of the urinary tract, by way of a genital tract, by way of the gastrointestinal tract, or by inhalation.

An effective amount for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

The vaccines of the present invention can be administered in a dose, or dosages, where each dose comprises at least 100 bacterial cells/kg body weight or more; in certain embodiments 1000 bacterial cells/kg body weight or more; normally at least 10,000 cells; more normally at least 100,000 cells; most normally at least 1 million cells; often at least 10 million cells; more often at least 100 million cells; typically at least 1 billion cells; usually at least 10 billion cells; conventionally at least 100 billion cells; and sometimes at least 1 trillion cells/kg body weight. The present invention provides the above doses where the units of bacterial administration is colony forming units (CFU), the equivalent of CFU prior to psoralen treatment, or where the units are number of bacterial cells.

The vaccines of the present invention can be administered in a dose, or dosages, where each dose comprises between $10^7$ and $10^8$ bacteria per 70 kg body weight (or per 1.7 square meters surface area; or per 1.5 kg liver weight); $2\times10^7$ and $2\times10^8$ bacteria per 70 kg body weight (or per 1.7 square meters surface area; or per 1.5 kg liver weight); $5\times10^7$ and $5\times10^8$ bacteria per 70 kg body weight (or per 1.7 square meters surface area; or per 1.5 kg liver weight); $10^8$ and $10^9$ bacteria per 70 kg body weight (or per 1.7 square meters surface area; or per 1.5 kg liver weight); between $2.0\times10^8$ and $2.0\times10^9$ bacteria per 70 kg (or per 1.7 square meters surface area, or per 1.5 kg liver weight); between $5.0\times10^8$ to $5.0\times10^9$ bacteria per 70 kg (or per 1.7 square meters surface area, or per 1.5 kg liver weight); between $10^9$ and $10^{10}$ bacteria per 70 kg (or per 1.7 square meters surface area, or per 1.5 kg liver weight); between $2\times10^9$ and $2\times10^{10}$ bacteria per 70 kg (or per 1.7 square meters surface area, or per 1.5 kg liver weight); between $5\times10^9$ and $5\times10^{10}$ bacteria per 70 kg (or per 1.7 square meters surface area, or per 1.5 kg liver weight); between $10^{11}$ and $10^{12}$ bacteria per 70 kg (or per 1.7 square meters surface area, or per 1.5 kg liver weight); between $2\times10^{11}$ and $2\times10^{12}$ bacteria per 70 kg (or per 1.7 square meters surface area, or per 1.5 kg liver weight); between $5\times10^{11}$ and $5\times10^{12}$ bacteria per 70 kg (or per 1.7 square meters surface area, or per 1.5 kg liver weight);

between $10^{12}$ and $10^{13}$ bacteria per 70 kg (or per 1.7 square meters surface area); between $2\times10^{12}$ and $2\times10^{13}$ bacteria per 70 kg (or per 1.7 square meters surface area, or per 1.5 kg liver weight); between $5\times10^{12}$ and $5\times10^{13}$ bacteria per 70 kg (or per 1.7 square meters surface area, or per 1.5 kg liver weight); between $10^{13}$ and $10^{14}$ bacteria per 70 kg (or per 1.7 square meters surface area, or per 1.5 kg liver weight); between $2\times10^{13}$ and $2\times10^{14}$ bacteria per 70 kg (or per 1.7 square meters surface area, or per 1.5 kg liver weight); $5\times10^{13}$ and $5\times10^{14}$ bacteria per 70 kg (or per 1.7 square meters surface area, or per 1.5 kg liver weight); between $10^{14}$ and $10^{15}$ bacteria per 70 kg (or per 1.7 square meters surface area, or per 1.5 kg liver weight); between $2\times10^{14}$ and $2\times10^{15}$ bacteria per 70 kg (or per 1.7 square meters surface area, or per 1.5 kg liver weight); and so on, wet weight.

Also provided is one or more of the above doses, where the dose is administered by way of one injection every day, one injection every two days, one injection every three days, one injection every four days, one injection every five days, one injection every six days, or one injection every seven days, where the injection schedule is maintained for, e.g., one day only, two days, three days, four days, five days, six days, seven days, two weeks, three weeks, four weeks, five weeks, or longer. The invention also embraces combinations of the above doses and schedules, e.g., a relatively large initial bacterial dose, followed by relatively small subsequent doses, or a relatively small initial dose followed by a large dose.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

The present invention encompasses a method of administering a bacterial vaccine that is oral. Also provided is a method of administering a bacterial vaccine that is intravenous. Moreover, what is provided is a method of administering a bacterial vaccine that is oral, intramuscular, intravenous, intradermal and/or subcutaneous.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., PA; Chabner and Longo (eds.) (2001) Cancer Chemotherapy and Biotherapy, Lippincott, Williams & Wilkins, Phila., PA).

Additional agents which are beneficial to raising a cytolytic T cell response may be used as well. Such agents are termed herein carriers. These include, without limitation, B7 costimulatory molecule, interleukin-2, interferon-γ, GM-CSF, CTLA-4 antagonists, PD-1 antagonists, LAG-3 antagonists, VISTA antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The carrier can be a bacterial cell that is transformed to express the polypeptide or to deliver a polynucleoteide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, and other like immune modulators such as cyclic dinucleotide STING agonists including c-di-GMP, c-di-AMP, c-di-IMP, and c-AMP-GMP, used separately or in combination with the described compositions are also potential adjuvants. Other representative examples of adjuvants include the synthetic adjuvant QS-21 comprising a homogeneous saponin purified from the bark of *Quillaja saponaria* and *Corynebacterium parvum* (McCune et al., Cancer, 1979; 43:1619). It will be understood that the adjuvant is subject to optimization. In other words, the skilled artisan can engage in routine experimentation to determine the best adjuvant to use.

An effective amount of a therapeutic agent is one that will decrease or ameliorate the symptoms normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%.

The reagents and methods of the present invention provide a vaccine comprising only one vaccination; or comprising a first vaccination; or comprising at least one booster vaccination; at least two booster vaccinations; or at least three booster vaccinations. Guidance in parameters for booster vaccinations is available. See, e.g., Marth (1997) Biologicals 25:199-203; Ramsay, et al. (1997) Immunol. Cell Biol. 75:382-388; Gherardi, et al. (2001) Histol. Histopathol. 16:655-667; Leroux-Roels, et al. (2001) Acta Clin.

Belg. 56:209-219; Greiner, et al. (2002) Cancer Res. 62:6944-6951; Smith, et al. (2003) J. Med. Virol. 70:Supp1.1:S38-541; Sepulveda-Amor, et al. (2002) Vaccine 20:2790-2795).

Formulations of therapeutic agents may be prepared for storage by mixing with physiologically acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

EXAMPLES

The following examples serve to illustrate the present invention. These examples are in no way intended to limit the scope of the invention.

Example 1. Construction of Lm Deletion Mutant Strains

To construct the deletion mutant for the dxs gene coding for the 1-deoxy-D-xylulose 5-phosphate synthase, both the upstream and downstream region of the coding sequence were amplified by using primers DXS1-DXS3 and DXS4-DXS2 (Table 4) respectively using as template chromosomal DNA from *L. monocytogenes* (Lm) DP-L4056.

After both fragments were purified using QIAquick PCR purification kit we performed splicing by overlap extension (SOE)-PCR using both fragments as template and primers DXS1 and DXS2 in the reaction. The amplified fragment was cloned into the pCR-Blunt vector (Invitrogen) and transformed into *Escherichia coli* TOP 10 competent cells (Invitrogen). Kanamycin resistant colonies were screened by colony-PCR and plasmid preparations from the positive clones were sequenced to confirm the identity of the amplified fragment.

A plasmid harboring the 1.2 Kbp fragment containing the up- and downstream region of the dxs gene was digested with SalI and BamHI enzymes (NEB) and the fragment subcloned into the pKSV107oriT vector previously digested with the same enzymes. A colony of *E. coli* SM10 harboring the desired construct was conjugated with the ΔactA Lm strain (DP-L4029). For this, cultures of the ΔactA Lm and the *E. coli* strain harboring the corresponding plasmid were grown overnight in brain-heart infusion (BHI) supplemented with 200 µg/ml Streptomycin and Luria-Bertani (LB) 100 µg/ml Ampicillin respectively. After this, cultures were diluted 1/100 in the same fresh media and incubated until an $OD_{600nm}$ of ~0.8. Three milliliters of the *E. coli* culture and 1.5 ml of Lm were centrifuged for 5 min at 12,000 rpm, washed with media without antibiotic and centrifuged again. Both strains were placed together in the same tube and centrifuged again. The pellet containing both strains was resuspended in ~30 µl of BHI, spotted onto a BHI agar plate and incubated 4 hs at 37 C. The mixture was resuspended in BHI and plated on BHI agar 10 µg/ml Chloramphenicol (Cm). Plates were incubated at 30° C. for 2 days. Colonies obtained were inoculated in BHI 10 µg/ml Cm and grown overnight at 42° C. with shaking (200 rpm). A dilution 1/100 of these cultures was performed in the same media and incubated overnight at 42 C. A new dilution (1/100) was made in BHI and tubes incubated at 30° C. for another 16 hrs.

Each culture was streaked for individual colonies on BHI agar media and isolated colonies obtained after 24 hrs of incubation at 30° C. were replica plated on BHI and BHI containing 10 µg/ml Cm. Colonies that showed Cm sensitivity were further analyzed by colony-PCR using primers DXS1 and DXS2. To confirm the deletion of the dxs gene, two new colony-PCR reactions were performed: one using primers DXS1 and DXS-int Rev and the second using primers DXS2 and DXS-int For. Colonies that showed a deletion of the dxs gene were grown in BHI Streptomycin for 16 hrs and stocks with glycerol (30%) prepared and keep at −80° C.

To construct a Δdxr mutant strain (a mutation in the gene encoding the 1-deoxy-D-xylulose 5-phosphate reductoisomerase), we followed the same allelic exchange protocol described above with the following modifications: the upstream and downstream regions of the coding sequence were amplified with primers DXR1-DXR3 and DXR2-DXR4 (Table 4) and the SOE-PCR was performed with primers DXR1 and DXR2. After obtaining putative Δdxr candidates, the colonies were analyzed by PCR using primers DXR1 and DXR2 as well as the following primers combinations DXR1-DXRint Rev and DXR2-DXRint For. Colonies that showed a deletion of the dxr gene were grown in BHI Streptomycin for 16 hrs and stocks with glycerol (30%) prepared and stored at −80° C.

To construct the mutant strain for the ygbP gene encoding the 4-diphosphocytidyl-2-C-methyl-D-erythritol synthase the upstream and downstream regions of the coding sequence are amplified with primers YGBP1-YGBP3 and YGBP4-YGBP2 respectively (Table 4). The SOE-PCR is performed with primers YGBP1 and YGBP2 and the same primers are used to confirm the mutation in the ΔactA Lm colonies obtained after the conjugation and the following steps described above. Primers YGBP1-YGBPint Rev and YGBP2-YGBPint For. Colonies that showed a deletion of the ygbP gene are grown in BHI Streptomycin for 16 hrs and stocks with glycerol (30%) prepared and stored at −80° C.

For the construction of the ΔychB mutant strain (a mutation in the gene encoding the 4-diphosphocytidyl-2-C-methyl-D-erythritol kinase), the protocol described above is followed with the following modifications: the upstream and downstream regions of the coding sequence are amplified with primers YCHB1-YCHB3 and YCHB2-YCHB4 (Table 4) and the SOE-PCR is performed with primers YCHB1 and YCHB2. After obtaining putative ΔychB candidates, the colonies are analyzed by PCR using primers YCHB1 and YCHB 2 as well as the following primers combinations YCHB1-YCHBint Rev and YCHB2-YCHBint For. Colonies that showed a deletion of the ychB gene were grown in BHI Streptomycin for 16 hrs and stocks with glycerol (30%) prepared and stored at −80° C.

To construct the mutant strain for the ygbB gene encoding the 2-C-methyl-D-erythritol 2,4-cyclopyrophosphate synthase, the upstream and downstream regions of the coding sequence are amplified with primers YGBB1-YGBB3 and YGBB4-YGBB2 respectively (Table 4). The SOE-PCR is performed with primers YGBB1 and YGBB2 and the same primers were used to confirm the mutation in the ΔactA Lm colonies obtained after the conjugation and the following steps described above. Primers YGBB1-YGBBint Rev and YGBB2-YGBBint For. Colonies that showed a deletion of the ygbB gene were grown in BHI Streptomycin for 16 hrs and stocks with glycerol (30%) prepared and stored at −80° C.

TABLE 4

| Primer | Sequence (5' to 3') |
| --- | --- |
| DXS1 | GGTCGACGATTACTCACGCTTGATGGGGC (SEQ ID NO: 7) |
| DXS2 | GGATCCTTCCTTCTCCACCTGTAATAGGTG (SEQ ID NO: 8) |
| DXS3 | TCATAGTCTCTTCGCCCTTAACTTAAGATCCAAATAAAAA CAACTCAC (SEQ ID NO: 9) |
| DXS4 | GTGAGTTGTTTTTATTTGGATCTTAAGTTAAGGGCGAAGA GACTATGA (SEQ ID NO: 10) |
| DXSINT-FOR | GCGAGTGTGTTAGAATTTATAGAAG (SEQ ID NO: 11) |
| DXSINT-REV | CCCAAATAAATTTATCTTTTGGAC (SEQ ID NO: 12) |
| DXR1 | GGTCGACTTGCAACTATTGCATTATATGAAG (SEQ ID NO: 13) |
| DXR2 | GGATCCCATTGATGGAAAGAACTTCATCCC (SEQ ID NO: 14) |
| DXR3 | CTATAAAAGTGTCTTTACATACGCACCTAGCAAAATAATT TTTTTCAT (SEQ ID NO: 15) |
| DXR4 | ATGAAAAAAATTATTTTGCTAGGTGCGTATGTAAAGACAC TTTTATAG (SEQ ID NO: 16) |
| DXRINT-FOR | AAATAGGTGGAACAATGCCGACAG (SEQ ID NO: 17) |
| DXRINT-REV | GCTTCTAAGGTAACACGATCTCTC (SEQ ID NO: 18) |
| YGBP1 | GGTCGACGTATCGGAATTAGTCGTCGTAACG (SEQ ID NO: 19) |
| YGBP2 | GGATCCACATCCACGCCTTCATCCCAGTCC (SEQ ID NO: 20) |
| YGBP3 | CTAATCATTTGCTATCCCTCCAAGAACCAACTCATAATTC ATGCTCAT (SEQ ID NO: 21) |
| YGBP4 | ATGAGCATGAATTATGAGTTGGTTCTTGGAGGGATAGCAA ATGATTAG (SEQ ID NO: 22) |
| YGBPINT-FOR | CTGCCTATTTTACGAAAAGCGCATC (SEQ ID NO: 23) |
| YGBPINT-REV | ATTCTTTTACATGCTTTCTTTCC (SEQ ID NO: 24) |
| YGBB1 | GGTCGACATGAGCATGAATTATGAGTTGG (SEQ ID NO: 25) |
| YGBB2 | GGATCCCATATCGTTGAAAGTAATCGTTTC (SEQ ID NO: 26) |
| YGBB3 | CAAGTAAGACAACGGCTAGACTTGATAACCTTGGCCAATT CTAATCAT (SEQ ID NO: 27) |
| YGBB4 | ATGATTAGAATTGGCCAAGGTTATCAAGTCTAGCCGTTGT CTTACTTG (SEQ ID NO: 28) |
| YGBBINT-FOR | GCTGAAAAGCCAAAAATGGCGCC (SEQ ID NO: 29) |
| YGBBINT-REV | TGACCAATATCACCAGCACCAATTG (SEQ ID NO: 30) |

TABLE 4-continued

| Primer | Sequence (5' to 3') |
| --- | --- |
| YCHB1 | GGTCGACGCTCAAAGAAGAAAAACGCTTTGG (SEQ ID NO: 31) |
| YCHB2 | GGATCCGGCCTAAATATGCTTGTAGTTCTC (SEQ ID NO: 32) |
| YCHB3 | GTATCGTTCTCGCCTTCACTCCATTGGTGCTGTAATGCTT ATTTTCAT (SEQ ID NO: 33) |
| YCHB4 | ATGAAAATAAGCATTACAGCACCAATGGAGTGAAGGCGAG AACGATAC (SEQ ID NO: 34) |
| YCHBINT-FOR | GTTAGCGTTTGGTGCTGAGGCGG (SEQ ID NO: 35) |
| YCHB INT-REV | ACGATCTTCTGGAATAAAGTGCGC (SEQ ID NO: 36) |

To construct the deletion mutant for the gcpE gene coding for the (E)-4-hydroxy-3-methyl-but-2-enyl pyrophosphate (HMB-PP) synthase, we amplified both the upstream and downstream region of the coding sequence by using primers GcpE1-E3 and GcpE4-E2 (Table 5) respectively using as template chromosomal DNA from *L. monocytogenes* (Lm) DP-L4056.

After both fragments were purified using QIAquick PCR purification kit we performed splicing by overlap extension (SOE)-PCR using both fragments as template and primers GcpE1 and GcpE2 in the reaction. The amplified fragment was cloned into the pCR-Blunt vector (Invitrogen) and transformed into *Escherichia coli* TOP 10 competent cells (Invitrogen). Kanamycin resistant colonies were screened by colony-PCR and plasmid preparations from the positive clones were sequenced to confirm the identity of the amplified fragment.

A plasmid harboring the 1.2 Kbp fragment containing the up- and downstream region of the gcpE gene was digested with SalI and BamHI enzymes (NEB) and the fragment subcloned into the pKSV107oriT vector previously digested with the same enzymes. A colony of *E. coli* SM10 harboring the desire construct was conjugated with the ΔactA Lm strain (DP-L4029). For this, cultures of the ΔactA Lm and the *E. coli* strain harboring the corresponding plasmid were grown overnight in brain-heart infusion (BHI) supplemented with 200 m/ml Streptomycin and Luria-Bertani (LB) 100 m/ml Ampicillin respectively. After this, cultures were diluted 1/100 in the same fresh media and incubated until an $OD_{600nm}$ of ~0.8. Three milliliters of the *E. coli* culture and 1.5 ml of Lm were centrifuged for 5 min at 12,000 rpm, washed with media without antibiotic and centrifuged again. Both strains were placed together in the same tube and centrifuged again. The pellet containing both strains was resuspended in ~30 μl of BHI, spotted onto a BHI agar plate and incubated 4 hs at 37° C. The mixture was resuspended in BHI and plated on BHI agar 10 m/ml Chloramphenicol (Cm). Plates were incubated at 30° C. for 2 days. Colonies obtained were inoculated in BHI 10 m/ml Cm and grew overnight at 42° C. with shaking (200 rpm). A dilution 1/100 of these cultures was performed in the same media and incubated for another overnight at 42° C. A new dilution (1/100) was made in BHI and tubes incubated at 30° C. for another 16 hrs.

TABLE 5

Primers used

| Name | 5' to 3' Sequence |
|---|---|
| GcpE 1 | GGTCGACCCTATCTCGATTGATCAAGATGAAC (SEQ ID NO: 37) |
| GcpE 2 | GGATCCGCTAGTTCAGGTGTCATAACTCGC (SEQ ID NO: 38) |
| GcpE 3 | CGATTATCTAAGGCTTTCCAAATCTTGGACTGGGCGAGTG TTTTCGCG (SEQ ID NO: 39) |
| GcpE 4 | CGCGAAAACACTCGCCCAGTCCAAGATTTGGAAAGCCTTA GATAATCG (SEQ ID NO: 40) |
| GcpE-int-Rev | GCAAGTAGGGCAGGAGATAAGCAT (SEQ ID NO: 41) |
| GcpE-int-For | ATTCACCGATTAGAAGAAGCTGG (SEQ ID NO: 42) |

Each culture was streaked on BHI agar plates and isolated colonies obtained after 24 hrs of incubation at 30° C. were replica plated on BHI and BHI containing 10 µg/ml Cm. Colonies that showed Cm sensitivity were further analyzed by colony-PCR using primers GcpE1 and GcpE2. To confirm the deletion of the gcpE gene, two new colony-PCR reactions were performed: one using primers GcpE1 and GcpE-int Rev and the second using primers GcpE2 and GcpE-int For. Those colonies that showed a deletion of the gcpE gene were grown in BHI Streptomycin for 16 hrs and stocks with glycerol (30%) prepared and stored at −80° C.

Example 2. Analysis of T-Cell Populations Resulting from Human Administration of a Listerial Cancer Vaccine A live-attenuated, strain of *Listeria monocytogenes* (Lm) encoding a mutant form of the tumor-associated antigens, epidermal growth factor receptor (EGFRvIII) and the cancer/testis antigen NY-ESO-1 (referred to as ADU-623) was used for immunization in human subjects with glioblastoma malignancy. Upon intravenous administration, live-attenuated *Listeria monocytogenes* encoding EGFRvIII-NY-ESO-1 vaccine is preferentially taken up by dendritic cells and expresses EGFRvIII and NY-ESO-1 in the cytosol of infected APCs. This promotes both a potent innate immune response and an adaptive immune response involving the recruitment and activation of T lymphocytes against EGFRvIII and NY-ESO-1-expressing tumor cells, which results in tumor cell lysis. Attenuation was achieved by deletion of the actA and inlB genes of the bacterial genome.

Inclusion Criteria:

Patients with a pathologic diagnosis of WHO Grade III or Grade IV astrocytic tumors that have completed standard of care or with radiographic evidence of progression following standard of care.

Tumor tissue blocks available to perform both EGFRvIII and NY-ESO-1 testing.

Eastern Cooperative Oncology Group (ECOG) performance status 0 or 1 or Karnofsky Performance Status (KPS) 70-100.

Age 18 years or above.

Have a life expectancy of more than 12 weeks

Laboratory values (performed within 5 days) within designated range.

For women and men of childbearing potential, an acceptable method of highly effective contraception Ability to give informed consent and comply with the protocol.

Exclusion Criteria:

Have a known allergy to both penicillin and sulfa

Have artificial (prosthetic) joint(s), orthopedic screw(s), metal plate(s) or other exogenous implant(s) or device(s) that cannot be easily removed (i.e., prosthetic heart valves).

Have any evidence of hepatic cirrhosis or clinical or radiographic ascites.

Have radiographic or clinically significant pleural effusion.

Receipt of prophylactic vaccine within 28 days of study treatment.

Unable to avoid close contact with another individual known to be at high risk of listeriosis (e.g., newborn infant, pregnant woman, HIV-positive individual).

History of allergy to yeast or any other component of the ADU-623 vaccine (e.g., glycerol).

Have an immunodeficiency disease or immunocompromised state (e.g., use of immunosuppressive agents; chemotherapy or radiation therapy within 14 days of study treatment).

Have had major surgery or significant traumatic injury occurring within 28 days before treatment administration or anticipated surgery or procedure requiring general anesthesia during study participation (including 28 days after last dose of ADU-623).

Use of more than 4 grams per day of acetaminophen.

Have received an investigational product within 28 days of study treatment or planned to receive within 28 days after vaccine administration.

Have an unhealed surgical wound.

Have clinically significant heart disease (such as uncontrolled angina, myocardial infarction with the last 3 months, congestive heart failure of New York Heart Association III or IV).

Have valvular heart disease that requires antibiotic prophylaxis for prevention of endocarditis.

Have an intercurrent illness that is either life-threatening or of clinical significance such that it might limit compliance with study requirements including, but not limited to, ongoing or active infection, metabolic or neurological disease, peripheral vascular disease or psychiatric illness.

Have insufficient peripheral venous access to permit completion of the study dosing and compliance with study phlebotomy regimen.

Have received a diagnosis of HIV, HCV, or HBV (patients with hepatitis C antibody positive may be enrolled if they are confirmed with negative viral load at screening).

Have an active autoimmune disease or history of autoimmune disease requiring systemic steroids or other immunosuppressive treatment.

Other medical or psychiatric conditions that in the opinion of the Principal Investigator would preclude safe participation in protocol.

Pregnant or lactating women, as treatment has unknown effect on the embryo or child.

Patients requiring chronic corticosteroid use will be excluded as this may mask toxic effects related to the vaccine and may prevent the development of effective immune responses following vaccination.

Patients were treated intravenously with $3\times10^7$ CFU of ADU-623 as indicated in FIG. 1. At the indicated time points, peripheral blood was collected via venipuncture into a sodium heparin blood collection tube and delivered to the laboratory. Whole blood was stained with antibodies targeting the indicated antigens for 15 minutes at room temperature. Red blood cells were lysed using FACSLyse (BD Biosciences) and the samples washed ×2 using HBSS w/o Ca++Mg+++1% BSA, 0.1% NaN3 and 10 U/mL sodium heparin. Cells were resuspended in wash buffer and analyzed by flow cytometry (LSRFortessa, BD Biosciences).

For identification of various T-cell subpopulations, the following antibodies were used for staining prior to flow cytometry:

| Target antigen | Fluorochrome | Vendor | Cat# | Clone |
| --- | --- | --- | --- | --- |
| CD45 | FITC | BD | 347463 | 2D1 |
| CD3 | Alexa 700 | eBio | 56-0038-42 | UCHT1 |
| CD4 | PerCP-Cy5.5 | BD | 341654 | SK3 |
| CD8 | APC-H7 | BD | 641409 | SK1 |
| CXCR3 | PE-Cy7 | BD | 560831 | 1C6/CXCR3 |
| TCR αβ | BV510 | BD | 563625 | T10B9.1A-31 |
| TCR γδ | BV421 | BD | 562560 | B1 |
| TCR Vγ9 | PE | BD | 555733 | B3 |
| TCR Vδ2 | APC | Milteny | 130-099-664 | 123R3 |
| CD69 | BV421 | BD | 562884 | FN50 |
| CD25 | BV605 | BD | 562660 | 2A3 |
| IFN-γ | APC | BD | 554702 | B27 |
| TNF-α | PE-Cy7 | BD | 557647 | MAb11 |
| rIL-2 | PE | BD | 559334 | MQ1-17H12 |

For HMB-PP or *Listeria* lysate stimulation of T-cells, 0.5×10$^6$ PBLs were incubated with 50 ng/ml HMBPP in 100 μl final volume for 1 h at 37° C., 5% $CO_2$ followed by an additional 5-h incubation in the presence of brefeldin A.

Figure 7:
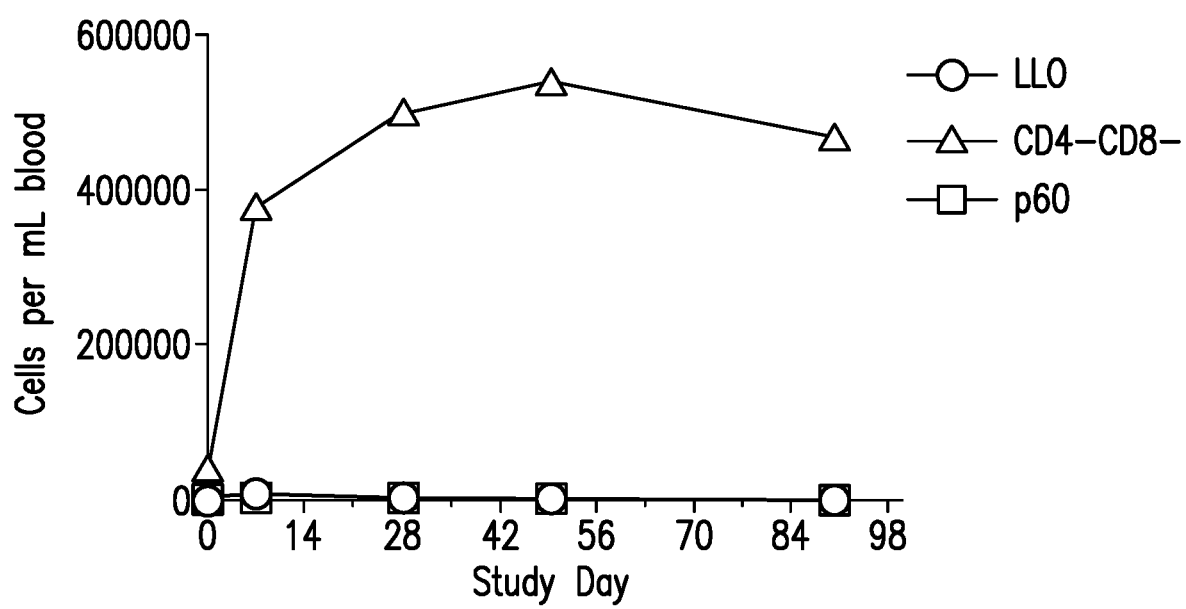
FIG. 7 depicts the absolute numbers of various T-cell populations following administration of ADU-623.

As depicted in FIG. 7, Peripheral blood was collected on the indicated day and stained with fluorochrome-conjugated monoclonal antibodies to CD45, CD3, CD4, CD8, gd TCR, Vg9 TCR, and Vd2 TCR. The absolute frequency of each population was determined using the SSC versus CD45 lymphocyte gate combined with the absolute lymphocyte count from the CBC. Additional blood at the same time point was used to isolate PBMC. 300,000 PBMC were used in an IFN-g ELISpot assay to quantify antigen-specific T cells. A 15x11 overlapping peptide library of LLO and p60 were used to identify LLO and p60-specific T cells, with the absolute frequency of those cells in the starting material determined using the absolute lymphocyte and monocyte counts from the CBC.

These data demonstrate that HMB-PP specific Vg9Vd2 T cells vastly outnumber LLO- and p60-specific ab T cells. Therefore, the clearance of the vaccine by these anti-bacterial cytolytic effector cells (Vg9Vd2 T cells) may limit the duration of infection, the magnitude of the inflammatory response, and the duration of antigen presentation to ab T cells.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of inducing an αβ T-cell response to at least one polypeptide antigen in a primate, said method comprising:
expressing the at least one polypeptide antigen from a Listeria cell administered to the primate, wherein the at least one polypeptide antigen is heterologous to the Listeria cell, and wherein the Listeria cell comprises a functionally deleted 2-C-methyl-D-erythritol-4-phosphate (MEP) pathway resulting in substantially blocked (E)-4-Hydroxy-3-methyl-but-2-enyl pyrophosphate (HMBPP) production by the Listeria cell,
wherein the Listeria cell is a Listeria monocytogenes cell.

2. The method of claim 1 wherein the Listeria cell comprises a functional mevalonate pathway whereby the Listeria cell produces isopentenyl diphosphate (IPP) in an amount sufficient for growth.

3. The method of claim 2 wherein the Listeria cell comprises a disruption in one or more genes which encode a protein selected from the group consisting of 1-deoxy-D-xylulose-5-phosphate (DOXP) synthase, DOXP reductoisomerase, 4-diphosphocytidyl-2C-methyl-D-erythritol (CDP-ME) synthase, 4-diphosphocytidyl-2C-methyl-D-erythritol (CDP-ME) kinase, 2-C-Methyl-D-erythritol-2,4-cyclopyrophosphate (MEcPP) synthase, and HMBPP synthase.

4. The method of claim 1, wherein the Listeria cell comprises a disruption in HMBPP synthase.

5. The method of claim 1, wherein the Listeria cell comprises a nucleic acid sequence encoding said at least one polypeptide antigen integrated into the genome of said Listeria cell operably linked to control sequences which cause the expression of the at least one polypeptide antigen by the Listeria cell.

6. The method of claim 5, wherein the Listeria cell is a Listeria monocytogenes which is an actA deletion mutant or an actA insertion mutant, an inlB deletion mutant or an inlB insertion mutant or a ΔactA/ΔinlB mutant comprising both an actA deletion or an actA insertion and an inlB deletion or an inlB insertion.

7. The method of claim 1, wherein the Listeria cell is a Listeria monocytogenes deleted of prfA on the bacterial chromosome and harbors an extra-chromosomal plasmid encoding PrfA.

8. The method of claim 5, wherein said nucleic acid sequence has been integrated into a virulence gene of said Listeria cell, and the integration of said nucleic acid sequence disrupts expression of the virulence gene or disrupts a coding sequence of the virulence gene.

9. The method of claim 8, wherein the virulence gene is actA or inlB.

10. The method of claim 1, wherein the Listeria cell is an attenuated Listeria monocytogenes cell.

11. The method of claim 10, wherein the Listeria cell is Listeria monocytogenes ΔactA/ΔinlB.

12. The method of claim 11, wherein the Listeria cell further comprises a genetic mutation that attenuates the ability of the Listeria cell to repair nucleic acid.

13. The method of claim 12, wherein the genetic mutation is in one or more genes selected from phrB, uvrA, uvrB, uvrC, uvrD and recA.

14. The method of claim 10, wherein the Listeria cell is a Listeria monocytogenes prfA mutant, the genome of which encodes a prfA protein which is constitutively active.

15. The method of claim 10, wherein the Listeria cell is a killed but metabolically active Listeria monocytogenes cell.

16. The method of claim 15, wherein the Listeria cell is a Listeria monocytogenes prfA mutant, the genome of which encodes a prfA protein which is constitutively active.

17. The method of claim 5, wherein the nucleic acid sequence is codon optimized for expression by the Listeria cell according to the Listeria cell's preferred codon usage.

18. The method of claim 5, wherein said Listeria cell is administered by one or more routes of administration selected from the group consisting of orally, intramuscularly, intravenously, intradermally, and subcutaneously to said subject.

19. The method of claim 18, wherein said at least one polypeptide antigen is expressed as a fusion protein comprising a secretory signal sequence.

20. The method of claim 19, wherein the secretory signal sequence is a Listeria monocytogenes ActA signal sequence.

21. The method of claim 18, wherein the at least one polypeptide antigens is a (are) cancer antigen(s).

22. The method of claim 18, wherein said composition, when delivered to said subject, induces an increase in the serum concentration of one or more proteins selected from the group consisting of Interleukin (IL)-12p70, Interferon (IFN)-γ, IL-6, Tumor necrosis factor (TNF) α, and monocyte chemoattractant protein (MCP)-1 at 24 hours following said delivery; and induces a CD4+ and/or CD8+antigen-specific T cell response against the at least one polypeptide antigens.

23. The method of claim 1, wherein the Listeria cell is administered according to an administration protocol which induces both αβ and γδ T cell populations in a subject.

24. The method of claim 23, wherein the Listeria cell is administered as a boost vaccine following administration of a prime vaccine which induces αβ cell populations but not γδ T cell populations.

* * * * *